United States Patent
Chumakov et al.

(10) Patent No.: US 6,955,902 B2
(45) Date of Patent: Oct. 18, 2005

(54) HIGH THROUGHPUT DNA SEQUENCING VECTOR

(75) Inventors: Ilya Chumakov, Vaulx-le-Penil (FR); Hiroaki Tanaka, Antony (FR)

(73) Assignee: Serono Genetics Institute, Inc. (FR)

( * ) Notice: Subject to any disclaimer, the term of this patent is extended or adjusted under 35 U.S.C. 154(b) by 402 days.

(21) Appl. No.: 09/849,866

(22) Filed: May 4, 2001

(65) Prior Publication Data

US 2002/0068333 A1 Jun. 6, 2002

Related U.S. Application Data

(62) Division of application No. 09/438,142, filed on Nov. 10, 1999, now Pat. No. 6,258,571, which is a continuation of application No. 09/058,746, filed on Apr. 10, 1998, now Pat. No. 6,022,716.

(51) Int. Cl.$^7$ ............ C12N 15/11; C12N 9/38; C12N 15/64; C12Q 1/00; C12Q 1/04
(52) U.S. Cl. ............ 435/91.4; 435/91.42; 435/91.5; 435/320.1; 435/476; 536/23.2; 536/23.7; 536/24.1
(58) Field of Search ............ 435/6, 7.6, 91.42, 435/91.5, 320.1, 455, 476, 91.4; 536/23.1, 23.2, 23.7, 24.1, 24.32, 24.33

(56) References Cited

U.S. PATENT DOCUMENTS

| | | | |
|---|---|---|---|
| 4,567,141 A | * | 1/1986 | Olsen ............ 435/91 |
| 5,227,288 A | | 7/1993 | Blattner |
| 5,356,773 A | | 10/1994 | Shen et al. |
| 5,851,808 A | | 12/1998 | Elledge et al. |
| 5,910,438 A | | 6/1999 | Bernard et al. |
| 5,948,622 A | | 9/1999 | Reznikoff et al. |
| 6,022,716 A | * | 2/2000 | Chumakov et al. ...... 435/91.42 |

FOREIGN PATENT DOCUMENTS

| | | |
|---|---|---|
| WO | WO 94/03616 | 2/1994 |
| WO | WO 97/10343 | 3/1997 |

OTHER PUBLICATIONS

Ahmed, A., "Use of transposon–promoted deletions in DNA sequence analysis", J. Mol. Biol. 174(4): 941–948 (1984).
Chen, E., et al., J. Genomics 17: 651–656 (1993).
Crane, Denis, et al., The Pichia pastoris HIS4 gene: nucleotide sequence, creation of a non–reverting his4 deletion mutant, and development of HIS4–based replicating and integrating plasmids, Curr. Genet 26:443–450 (1994).
Guo, L.H., Nucleic Acids Research 11(6): 5521–5540 (1983).
Christyakov, D. A., et al., "New cosmid vector pDEL–BAC: cloning of large fragments of genomic DNA for subsequent introduction of deletions and sequencing of the DNA of the deletion mutants which are formed", Molecular Biology 30(3): 1–20 (1996).
Henikoff, S., "An improved strategy for rapid direct sequencing of both strands of long DNA molecules cloned in a plasmid", Gene 28: 351–359 (1984).
Roach, J.C., et al., :Pairwise end sequencing: a unified approach to genomic mapping and sequencing, Genomics 26: 345–353 (1995).
Soubrier, F., et al., "pCOR: A New Design of Plasmid Vectors for Nonviral Gene Therapy", Gene Therapy, 6:1482–1488 (1999).
Staden, R.A., "A new computer method for the storage and manipulation of DNA gel reading data", Nucleic Acids Research 8: 3673–3694 (1980).
Tsai, et al., J. of Bacteriology 169(12): 5556–5562 (1987).
Wang, G., et al., "pDUAL: a transposon–based cosmid cloning vector for generating nested deletions and DNA sequencing templates in vivo", Proc. Natl. Acad. Sci. USA 90(16): 7874–7878 (1993).
GenBank Accession No. M77789, date Oct. 23, 1991.
GenBank Accession No. J01688, date Oct. 28, 1994.
GenBank Accession No. X06404, date Nov. 8, 1995.
GenBank Accession No. U46017, date Feb. 12, 1996.
GenBank Accession No. U51113, date Feb. 6, 1997.
Specification of related U.S. Appl. No. 09/438,142, filed Nov. 10, 1999.

* cited by examiner

*Primary Examiner*—Sean McGarry
*Assistant Examiner*—Jane Zara
(74) *Attorney, Agent, or Firm*—Saliwanchik, Lloyd & Saliwanchik

(57) ABSTRACT

High throughput DNA sequencing vectors for generating nested deletions using enzymatic techniques and/or transposition-based techniques are disclosed. Methods of constructing contigs of long DNA sequences and methods of generating nested deletions are also disclosed. A truncated lacZ derivative useful in measuring the copy number of the lacZ derivative in a host cell is also disclosed.

17 Claims, 23 Drawing Sheets

FIG. 3

| FIG. 3A |
|---|
| FIG. 3B |
| FIG. 3C |

Generation of nested deletions with exoIII pGenDel Tn1000 single copy left end BAC

Features labeled on plasmid map:
- oriLRr PCR primer
- OR1 seq. primer
- PmlI
- kan ~1.3 kb
- Tn1000 right end (39pb)
- f1ori' ~0.6kb
- Xba I
- RepELR primer
- ori S
- repE
- LRT3RA PCR primer
- parA inc C
- parB
- parC
- T3 seq. primer
- BstE II
- Kpn I'/Hpa I'
- rpsL R PCR primer
- sacB+ (Sucs) ~1.5kb
- Tn1000 left end (39pb)
- slrA + resistant (Str s) ~0.7kb
- SP6 seq. primer
- SLR PCR primer
- MluJ
- lacZα ~0.35 kb
- ScaI
- Avr II
- insert
- OS1 seq. primer
- oriLRd PCR primer kanamycine resistant, streptomycine resistant if introduced into streptomycine resistant cells, sucrose sensitive, faint blue on IPTG/Xgal plates → generation of linear substrates by LR PCR with SLR3 and LRT3RA primers from cells lacZ ori— PmlI        PmlI ori— f1 ori    repE
(pUC19) ScaI INSERT ScaI (pUC19) kan   ori S

```
SLR 3 primer
5/TpTpTpCpGpCpG --------                                              CpGpGpCpTpTpT3/
3/ApApApGpCpGpC --------                                              GpCpCpGpApApApA5/
                                                                      LRT3RA primer
```

| FIG. 4A |
|---|
| FIG. 4B |
| FIG. 4C |

FIG. 4A

Generation of nested deletions with Mung bean nuclease

[Plasmid map: pGenDel Tn1000 single copy recombinant, showing features: kan ~1.3 kb, flori ~0.6kb, ori S, repE, inc C, parA, parB, parC, strA+ resistant (Str³) ~0.7kb, Tn1000 left end (39pb), sacB+ (Suc³) ~1.5kb, lacZ'α ~0.35 kb, insert, Tn1000 right end (39pb); restriction sites: Xba I, PmlI, Scal, Avr II, MluI, Kpn I'/Hpa I', BstE II; primers: oriLRr PCR primer, OR1 seq.primer, oriLRd PCR primer, OS1 seq.primer, SLR PCR primer, SP6 seq. primer, rpsLR PCR primer, repELR primer, T3 seq. primer, LRT3RA PCR primer]

kanamycine resistant, streptomycine resistant, streptomycine resistant if introduced into streptomycine resistant cells, sucrose sensitive, faint blue on IPTG/Xgal plates ⇒  generation of linear substrates by LR PCR with SLR3 and LRT3RA primers from cells lacZ   ori–       PmlI          PmlI   ori–      f1 ori     repE
       (pUC19)  Scal INSERT Scal (pUC19) kan     ori S 5/TpTpTpCpGpCpG ─────────────────────────────────── CpGpGpCpTpTpT3/
3/ApApApGpCpGpC ─────────────────────────────────── GpCpCpGpApApApA5/

SLR 3 primer →                                    ← LRT3RA primer

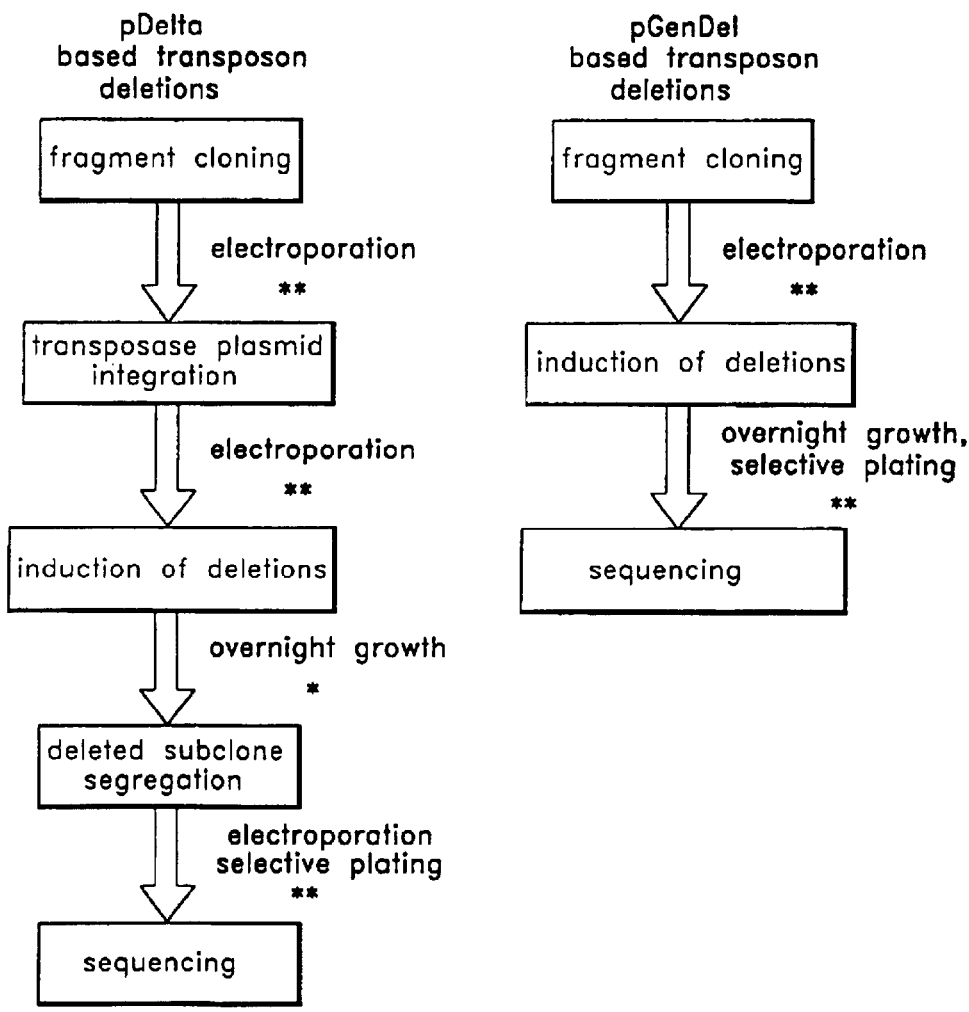

B. ORDERED SHOTGUN SEQUENCING—OSS

1. SIMULTANEOUS SEQUENCING OF BOTH ENDS OF LIMITED NUMBER OF SUBCLONES (1.5–2 FOLD SEQUENCE COVERAGE).
2. ASSEMBLY OF MINIMAL TILING PATH OF SUBCLONES BY PAIRWISE SEQUENCE OVERLAP.
3. PRIMER WALKING FOR EXTENSIVE SEQUENCING OF MINIMAL TILING PATH SUBCLONES

C. MULTIPLE NUCLEATION POINT WALKING STRATEGY

1. SIMULTANEOUS COMPLETE SEQUENCING OF LIMITED NUMBER OF LARGE INSERT SIZE SUBCLONES WITH PAIRWISE END SEQUENCING FOR THE REST OF THEM RESULTS IN MINIMAL TILING PATH CONTAINING NUCLEATION POINTS OF HIGH QUALITY SEQUENCE.
2. TRANSPOSON MEDIATED SEQUENCING OF MINIMAL TILING PATH.

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 10317 base pairs
      (B) TYPE: NUCLEIC ACID
      (C) STRANDEDNESS: DOUBLE
      (D) TOPOLOGY: CIRCULAR (ii) MOLECULE TYPE: synthetic DNA (vi) ORIGINAL SOURCE:
      (A) ORGANISM: Cloning vector pGenDEL -continued

```
(ix) FEATURE:
      (A) NAME/KEY: pGendel
      (B) LOCATION: 1..10317

(ix) FEATURE:
      (A) NAME/KEY: Homology with X06404 compl (411..1668)
      (B) LOCATION: 9..1266
      (C) IDENTIFICATION METHOD: blastn against X06404

(ix) FEATURE:
      (A) NAME/KEY: Kanamycin resistance gene CDS
      (B) LOCATION: 142..957
      (C) IDENTIFICATION METHOD: By homology to X06404

(ix) FEATURE:
      (A) NAME/KEY: Tn1000'sright end
      (B) LOCATION: complement 1332..1371
      (C) IDENTIFICATION METHOD: blastn against X60200)

(ix) FEATURE:
      (A) NAME/KEY: Homology with U46017 (1-472)
      (B) LOCATION: 1423..1894
      (C) IDENTIFICATION METHOD: blastn against U46017

(ix) FEATURE:
      (A) NAME/KEY: single stranded DNA replication origin
      (B) LOCATION: 1423..1894
      (C) IDENTIFICATION METHOD: By homology to U46017
      (D) OTHER INFORMATION: mutation T -> C 1658

(ix) FEATURE:
      (A) NAME/KEY: Homology with U51113 (2382..6997)
      (B) LOCATION: 1896..6544
      (C) IDENTIFICATION METHOD: blastn against U51113

(ix) FEATURE:
      (A) NAME/KEY: OriS
      (B) LOCATION: 1972..2188
      (C) IDENTIFICATION METHOD: By homology to U51113

(ix) FEATURE:
      (A) NAME/KEY: repELR
      (B) LOCATION: 2897..2918
      (D) OTHER INFORMATION: Described in seqID 16

(ix) FEATURE:
      (A) NAME/KEY: RepE
      (B) LOCATION: 2903..3034
      (C) IDENTIFICATION METHOD: By homology to U51113

(ix) FEATURE:
      (A) NAME/KEY: T3
      (B) LOCATION: 3043..3059
      (D) OTHER INFORMATION: Described in seqID 17

(ix) FEATURE:
      (A) NAME/KEY: LRT3RA
      (B) LOCATION: complement 3045..3069
      (D) OTHER INFORMATION: Described in seqID 15

(ix) FEATURE:
      (A) NAME/KEY: IncC
      (B) LOCATION: 3070..3320
      (C) IDENTIFICATION METHOD: By homology to U51113
      (D) OTHER INFORMATION: insertion 33 bases 3038..3071

(ix) FEATURE:
      (A) NAME/KEY: ParA
      (B) LOCATION: 3655..4821
      (C) IDENTIFICATION METHOD: By homology to U51113
      (D) OTHER INFORMATION: mutation G -> A 3878

(ix) FEATURE:
      (A) NAME/KEY: ParB
      (B) LOCATION: 4821..5792
      (C) IDENTIFICATION METHOD: By homology to U51113

(ix) FEATURE:
```

-continued

```
         (A) NAME/KEY: ParC
         (B) LOCATION: 5865..6382
         (C) IDENTIFICATION METHOD: By homology to U51113

(ix) FEATURE:
         (A) NAME/KEY: Homology with J01688 (complement 175..819)
         (B) LOCATION: 6574..7218
         (C) IDENTIFICATION METHOD: blastn against J01688
         (D) OTHER INFORMATION: mutation A -> G 7096

(ix) FEATURE:
         (A) NAME/KEY: CDS streptomycin sensitivity gene
         (B) LOCATION: complement 6716..7090
         (C) IDENTIFICATION METHOD: By homology to J01688
         (D) OTHER INFORMATION:  mutation A -> G 6728
             mutation G -> C 6821
             mutation C -> T 6866
             mutation T -> C 7013
             mutation T -> A 7058

(ix) FEATURE:
         (A) NAME/KEY: rpsLR
         (B) LOCATION: 7155..7174
         (D) OTHER INFORMATION: Described in seqID 12

(ix) FEATURE:
         (A) NAME/KEY: SP6
         (B) LOCATION: 7230..7248
         (D) OTHER INFORMATION: Described in seqID 13

(ix) FEATURE:
         (A) NAME/KEY: Tn1000's left end
         (B) LOCATION: 7252..7291
         (C) IDENTIFICATION METHOD: blast (X60200)

(ix) FEATURE:
         (A) NAME/KEY: Homology with X02730 (complement 37..1959)
         (B) LOCATION: 7305..9227
         (C) IDENTIFICATION METHOD: blastn against X02730

(ix) FEATURE:
         (A) NAME/KEY: CDS levansucrase gene
         (B) LOCATION: complement 7379..8800
         (C) IDENTIFICATION METHOD: By homology to X02730
         (D) OTHER INFORMATION:  mutation T -> C 7466
             mutation A -> G 7739
             mutation T -> C (Asn -> Asp) 8347
             mutation T -> C 8600
             mutation G -> A (Ala -> Val) 8772

(ix) FEATURE:
         (A) NAME/KEY: SLR3
         (B) LOCATION: 8711..8731
         (D) OTHER INFORMATION: Described in seqID 14

(ix) FEATURE:
         (A) NAME/KEY: Homology with J01636 (complement 1158..1465)
         (B) LOCATION: 9298..9623
         (C) IDENTIFICATION METHOD: blastn against J01636

(ix) FEATURE:
         (A) NAME/KEY: CDS alpha peptide beta-galactosidase
         (B) LOCATION: complement 9276..9497
         (C) IDENTIFICATION METHOD: By homology to J01636

(ix) FEATURE:
         (A) NAME/KEY: primer HE1
         (B) LOCATION: complement 9465..9479

(ix) FEATURE:
         (A) NAME/KEY: primer HE2
         (B) LOCATION: 9461..9475

(ix) FEATURE:
         (A) NAME/KEY: primer LacLRS2Avr
         (B) LOCATION: complement 9603..9630

(ix) FEATURE:
         (A) NAME/KEY: primer LacE2Mlu
```

```
GGTATGAGTC AGCAACACCT TCTTCACGAG GCAGACCTCA GCGCCCCCCC CCCCCTGCAG    1260

GTCGACTATA CAACGATCCC GCCATCACCA GGCCATCTGG CTGGGGTGCT TAACCGTAAG    1320

TCTGACGAAT TGGGGTTTGA GGGCCAATGG AACGAAAACG TACGTTAAGG ATCAGTTCCC    1380

TATAGTGAGT CGTATTAGCG GCCAGATCGA TCTAAGTGCC ACCTAAATTG TAAGCGTTAA    1440

TATTTTGTTA AAATTCGCGT TAAATTTTTG TTAAATCAGC TCATTTTTTA ACCAATAGGC    1500

CGAAATCGGC AAAATCCCTT ATAAATCAAA AGAATAGACC GAGATAGGGT TGAGTGTTGT    1560

TCCAGTTTGG AACAAGAGTC CACTATTAAA GAACGTGGAC TCCAACGTCA AAGGGCGAAA    1620

AACCGTCTAT CAGGGCGATG GCCCACTACG TGAACCACCA CCCTAATCAA GTTTTTTGGG    1680

GTCGAGGTGC CGTAAAGCAC TAAATCGGAA CCCTAAAGGG AGCCCCCGAT TTAGAGCTTG    1740

ACGGGGAAAG CCGGCGAACG TGGCGAGAAA GGAAGGGAAG AAAGCGAAAG GAGCGGGCGC    1800

TAGGGCGCTG GCAAGTGTAG CGGTCACGCT GCGCGTAACC ACCACACCCG CCGCGCTTAA    1860

TGCGCCGCTA CAGGGCGCGT CCCATTCGCC ATTCGTCGAG TGAGCGAGGA AGCACCAGGG    1920

AACAGCACTT ATATATTCTG CTTACACACG ATGCCTGAAA AAACTTCCCT TGGGGTTATC    1980

CACTTATCCA CGGGGATATT TTTATAATTA TTTTTTTTAT AGTTTTTAGA TCTTCTTTTT    2040

TAGAGCGCCT TGTAGGCCTT TATCCATGCT GGTTCTAGAG AAGGTGTTGT GACAAATTGC    2100

CCTTTCAGTG TGACAAATCA CCCTCAAATG ACAGTCCTGT CTGTGACAAA TTGCCCTTAA    2160

CCCTGTGACA AATTGCCCTC AGAAGAAGCT GTTTTTTCAC AAAGTTATCC CTGCTTATTG    2220

ACTCTTTTTT ATTTAGTGTG ACAATCTAAA AACTTGTCAC ACTTCACATG GATCTGTCAT    2280

GGCGGAAACA GCGGTTATCA ATCACAAGAA ACGTAAAAAT AGCCCGCGAA TCGTCCAGTC    2340

AAACGACCTC ACTGAGGCGG CATATAGTCT CTCCCGGGAT CAAAAACGTA TGCTGTATCT    2400

GTTCGTTGAC CAGATCAGAA AATCTGATGG CACCCTACAG GAACATGACG GTATCTGCGA    2460

GATCCATGTT GCTAAATATG CTGAAATATT CGGATTGACC TCTGCGGAAG CCAGTAAGGA    2520

TATACGGCAG GCATTGAAGA GTTTCGCGGG GAAGGAAGTG GTTTTTTATC GCCCTGAAGA    2580

GGATGCCGGC GATGAAAAAG CTATGAATC TTTTCCTTGG TTTATCAAAC GTGCGCACAG    2640

TCCATCCAGA GGGCTTTACA GTGTACATAT CAACCCATAT CTCATTCCCT TCTTTATCGG    2700

GTTACAGAAC CGGTTTACGC AGTTTCGGCT TAGTGAAACA AAAGAAATCA CCAATCCGTA    2760

TGCCATGCGT TTATACGAAT CCCTGTGTCA GTATCGTAAG CCGGATGGCT CAGGCATCGT    2820

CTCTCTGAAA ATCGACTGGA TCATAGAGCG TTACCAGCTG CCTCAAAGTT ACCAGCGTAT    2880

GCCTGACTTC CGCCGCCGCT TCCTGCAGGT CTGTGTTAAT GAGATCAACA GCAGAACTCC    2940

AATGCGCCTC TCATACATTG AGAAAAAGAA AGGCCGCCAG ACGACTCATA TCGTATTTTC    3000

CTTCCGCGAT ATCACTTCCA TGACGACAGG ATAGTCTGGT GGATTAACCC TCACTAAAGG    3060

GACGGCTTTT GAGGGTTATC TGTCACAGAT TTGAGGGTGG TTCGTCACAT TTGTTCTGAC    3120

CTACTGAGGG TAATTTGTCA CAGTTTTGCT GTTTCCTTCA GCCTGCATGG ATTTTCTCAT    3180

ACTTTTTGAA CTGTAATTTT TAAGGAAGCC AAATTTGAGG GCAGTTTGTC ACAGTTGATT    3240

TCCTTCTCTT TCCCTTCGTC ATGTGACCTG ATATCGGGGG TTAGTTCGTC ATCATTGATG    3300

AGGGTTGATT ATCACAGTTT ATTACTCTGA ATTGGCTATC CGCGTGTGTA CCTCTACCTG    3360

GAGTTTTTCC CACGGTGGAT ATTTCTTCTT GCGCTGAGCG TAAGAGCTAT CTGACAGAAC    3420

AGTTCTTCTT TGCTTCCTCG CCAGTTCGCT CGCTATGCTC GGTTACACGG CTGCGGCGAG    3480

CGCTAGTGAT AATAAGTGAC TGAGGTATGT GCTCTTCTTA TCTCCTTTTG TAGTGTTGCT    3540

CTTATTTTAA ACAACTTTGC GGTTTTTTGA TGACTTTGCG ATTTTGTTGT TGCTTTGCAG    3600
```

```
TAAATTGCAA GATTTAATAA AAAAACGCAA AGCAATGATT AAAGGATGTT CAGAATGAAA    3660

CTCATGGAAA CACTTAACCA GTGCATAAAC GCTGGTCATG AAATGACGAA GGCTATCGCC    3720

ATTGCACAGT TTAATGATGA CAGCCCGGAA GCGAGGAAAA TAACCCGGCG CTGGAGAATA    3780

GGTGAAGCAG CGGATTTAGT TGGGGTTTCT TCTCAGGCTA TCAGAGATGC CGAGAAAGCA    3840

GGGCGACTAC CGCACCCGGA TATGGAAATT CGAGGACAGG TTGAGCAACG TGTTGGTTAT    3900

ACAATTGAAC AAAATTAATCA TATGCGTGAT GTGTTTGGTA CGCGATTGCG ACGTGCTGAA    3960

GACGTATTTC CACCGGTGAT CGGGGTTGCT GCCCATAAAG GTGGCGTTTA CAAAACCTCA    4020

GTTTCTGTTC ATCTTGCTCA GGATCTGGCT CTGAAGGGGC TACGTGTTTT GCTCGTGGAA    4080

GGTAACGACC CCCAGGGAAC AGCCTCAATG TATCACGGAT GGGTACCAGA TCTTCATATT    4140

CATGCAGAAG ACACTCTCCT GCCTTTCTAT CTTGGGAAA AGGACGATGT CACTTATGCA    4200

ATAAAGCCCA CTTGCTGGCC GGGGCTTGAC ATTATTCCTT CCTGTCTGGC TCTGCACCGT    4260

ATTGAAACTG AGTTAATGGG CAAATTTGAT GAAGGTAAAC TGCCCACCGA TCCACACCTG    4320

ATGCTCCGAC TGGCCATTGA AACTGTTGCT CATGACTATG ATGTCATAGT TATTGACAGC    4380

GCGCCTAACC TGGGTATCGG CACGATTAAT GTCGTATGTG CTGCTGATGT GCTGATTGTT    4440

CCCACGCCTG CTGAGTTGTT TGACTACACC TCCGCACTGC AGTTTTTCGA TATGCTTCGT    4500

GATCTGCTCA AGAACGTTGA TCTTAAAGGG TTCGAGCCTG ATGTACGTAT TTTGCTTACC    4560

AAATACAGCA ATAGTAATGG CTCTCAGTCC CCGTGGATGG AGGAGCAAAT TCGGGATGCC    4620

TGGGGAAGCA TGGTTCTAAA AAATGTTGTA CGTGAAACGG ATGAAGTTGG TAAAGGTCAG    4680

ATCCGGATGA GAACTGTTTT TGAACAGGCC ATTGATCAAC GCTCTTCAAC TGGTGCCTGG    4740

AGAAATGCTC TTTCTATTTG GGAACCTGTC TGCAATGAAA TTTTCGATCG TCTGATTAAA    4800

CCACGCTGGG AGATTAGATA ATGAAGCGTG CGCCTGTTAT TCCAAAACAT ACGCTCAATA    4860

CTCAACCGGT TGAAGATACT TCGTTATCGA CACCAGCTGC CCCGATGGTG GATTCGTTAA    4920

TTGCGCGCGT AGGAGTAATG GCTCGCGGTA ATGCCATTAC TTTGCCTGTA TGTGGTCGGG    4980

ATGTGAAGTT TACTCTTGAA GTGCTCCGGG GTGATAGTGT TGAGAAGACC TCTCGGGTAT    5040

GGTCAGGTAA TGAACGTGAC CAGGAGCTGC TTACTGAGGA CGCACTGGAT GATCTCATCC    5100

CTTCTTTTCT ACTGACTGGT CAACAGACAC CGGCGTTCGG TCGAAGAGTA TCTGGTGTCA    5160

TAGAAATTGC CGATGGGAGT CGCCGTCGTA AAGCTGCTGC ACTTACCGAA AGTGATTATC    5220

GTGTTCTGGT TGGCGAGCTG GATGATGAGC AGATGGCTGC ATTATCCAGA TTGGGTAACG    5280

ATTATCGCCC AACAAGTGCT TATGAACGTG GTCAGCGTTA TGCAAGCCGA TTGCAGAATG    5340

AATTTGCTGG AAATATTTCT GCGCTGGCTG ATGCGGAAAA TATTTCACGT AAGATTATTA    5400

CCCGCTGTAT CAACACCGCC AAATTGCCTA AATCAGTTGT TGCTCTTTTT TCTCACCCCG    5460

GTGAACTATC TGCCCGGTCA GGTGATGCAC TTCAAAAAGC CTTTACAGAT AAAGAGGAAT    5520

TACTTAAGCA GCAGGCATCT AACCTTCATG AGCAGAAAAA AGCTGGGGTG ATATTTGAAG    5580

CTGAAGAAGT TATCACTCTT TTAACTTCTG TGCTTAAAAC GTCATCTGCA TCAAGAACTA    5640

GTTTAAGCTC ACGACATCAG TTTGCTCCTG GAGCGACAGT ATTGTATAAG GGCGATAAAA    5700

TGGTGCTTAA CCTGGACAGG TCTCGTGTTC CAACTGAGTG TATAGAGAAA ATTGAGGCCA    5760

TTCTTAAGGA ACTTGAAAAG CCAGCACCCT GATGCGACCA CGTTTTAGTC TACGTTTATC    5820

TGTCTTTACT TAATGTCCTT TGTTACAGGC CAGAAAGCAT AACTGGCCTG AATATTCTCT    5880

CTGGGCCCAC TGTTCCACTT GTATCGTCGG TCTGATAATC AGACTGGGAC CACGGTCCCA    5940
```

```
CTCGTATCGT CGGTCTGATT ATTAGTCTGG GACCACGGTC CCACTCGTAT CGTCGGTCTG   6000

ATTATTAGTC TGGGACCACG GTCCCACTCG TATCGTCGGT CTGATAATCA GACTGGGACC   6060

ACGGTCCCAC TCGTATCGTC GGTCTGATTA TTAGTCTGGG ACCATGGTCC CACTCGTATC   6120

GTCGGTCTGA TTATTAGTCT GGGACCACGG TCCCACTCGT ATCGTCGGTC TGATTATTAG   6180

TCTGGAACCA CGGTCCCACT CGTATCGTCG GTCTGATTAT TAGTCTGGGA CCACGGTCCC   6240

ACTCGTATCG TCGGTCTGAT TATTAGTCTG GGACCACGAT CCCACTCGTG TTGTCGGTCT   6300

GATTATCGGT CTGGGACCAC GGTCCCACTT GTATTGTCGA TCAGACTATC AGCGTGAGAC   6360

TACGATTCCA TCAATGCCTG TCAAGGGCAA GTATTGACAT GTCGTCGTAA CCTGTAGAAC   6420

GGAGTAACCT CGGTGTGCGG TTGTATGCCT GCTGTGGATT GCTGCTGTGT CCTGCTTATC   6480

CACAACATTT TGCGCACGGT TATGTGGACA AAATACCTGG TTACCCAGGC CGTGCCGGCA   6540

CGTTCGAAAG GAAACGACAG GTGCTGAAAG CGAGATCCGG CAGAATTTTA CGCTGACCAA   6600

TGACGCGACG ACGTGGCATG GAAATACTCC GTTGTTAATT CAGGATTGTC CAAAACTCTA   6660

CGAGTTTAGT TTGACATTTA AGTTAAAACG TTTGGCCTTA CTTAACGGAG AACCATTAAG   6720

CCTTAGGGCG CTTCACGCCA TACTTGGAAC GAGCCTGCTT ACGGTCTTTA CGCCGGAGC    6780

AGTCAAGCGC ACCACGTACG GTGTGGTAAC GAACACCCGG CAGGTCTTTA ACACGACCGC   6840

CACGGATCAG GATCACGGAG TGCTCTTGCA GGTTGTGACC TTCACCACCG ATGTAGGAAG   6900

TCACTTCGAA ACCGTTAGTC AGACGAACAC GGCATACTTT ACGCAGCGCG GAGTTCGGTT   6960

TTTTAGGAGT GGTAGTATAT ACACGAGTAC ATACGCCACG TTTTTGCGGG CACGCTTCCA   7020

GCGCAGGCAC GTTGCTTTTC GCAACTTTGC GAGCACGAGG TTTGCGTACC AGCTGGTTAA   7080

CTGTTGCCAT TAAATGGCTC CTGGTTTTAG CTTTTGCTTC GTAAACACGT AATAAAACGT   7140

CCTCACACAA TATGAGGACG CCGAATTTTA GGGCGATGCC GAAAAGGTGT CAAGAAATAT   7200

ACAACGATCC CGCCATCACG CGCGCGTCCG ATTTAGGTGA CACTATAGAG ATCCTTAACG   7260

TACGTTTTCG TTCCATTGGC CCTCAAACCC CGATCCGGGG AATTTATGGG ATTCACCTTT   7320

ATGTTGATAA GAAATAAAAG AAAATGCCAA TAGGATATCG GCATTTTCTT TTGCGTTTTT   7380

ATTTGTTAAC TGTTAATTGT CCTTGTTCAA GGATGCTGTC TTTGACAACA GATGTTTTCT   7440

TGCCTTTGAT GTTCAGCAGG AAGCTCGGCG CAAACGTTGA TTGTTTGTCT GCGTAGAATC   7500

CTCTGTTTGT CATATAGCTT GTAATCACGA CATTGTTTCC TTTCGCTTGA GGTACAGCGA   7560

AGTGTGAGTA AGTAAAGGTT ACATCGTTAG GATCAAGATC CATTTTTAAC ACAAGGCCAG   7620

TTTTGTTCAG CGGCTTGTAT GGGCCAGTTA AAGAATTAGA AACATAACCA AGCATGTAAA   7680

TATCGTTAGA CGTAATGCCG TCAATCGTCA TTTTTGATCC GCGGGAGTCA GTGAACAGAT   7740

ACCATTTGCC GTTCATTTTA AAGACGTTCG CGCGTTCAAT TCATCTGTT ACTGTGTTAG    7800

ATGCAATCAG CGGTTTCATC ACTTTTTTCA GTGTGTAATC ATCGTTTAGC TCAATCATAC   7860

CGAGAGCGCC GTTTGCTAAC TCAGCCGTGC GTTTTTTATC GCTTTGCAGA AGTTTTTGAC   7920

TTTCTTGACG GAAGAATGAT GTGCTTTTGC CATAGTATGC TTTGTTAAAT AAAGATTCTT   7980

CGCCTTGGTA GCCATCTTCA GTTCCAGTGT TTGCTTCAAA TACTAAGTAT TTGTGGCCTT   8040

TATCTTCTAC GTAGTGAGGA TCTCTCAGCG TATGGTTGTC GCCTGAGCTG TAGTTGCCTT   8100

CATCGATGAA CTGCTGTACA TTTTGATACG TTTTTCCGTC ACCGTCAAAG ATTGATTAT    8160

AATCCTCTAC ACCGTTGATG TTCAAAGAGC TGTCTGATGC TGATACGTTA ACTTGTGCAG   8220

TTGTCAGTGT TTGTTTGCCG TAATGTTTAC CGGAGAAATC AGTGTAGAAT AAACGGATTT   8280

TTCCGTCAGA TGTAAATGTG GCTGAACCTG ACCATTCTTG TGTTTGGTCT TTTAGGATAG   8340
```

```
AATCATCTGC ATCGAATTTG TCGCTGTCTT TAAAGACGCG GCCAGCGTTT TTCCAGCTGT      8400

CAATAGAAGT TTCGCCGACT TTTTGATAGA ACATGTAAAT CGATGTGTCA TCCGCATTTT      8460

TAGGATCTCC GGCTAATGCA AAGACGATGT GGTAGCCGTG ATAGTTTGCG ACAGTGCCGT      8520

CAGCGTTTTG TAATGGCCAG CTGTCCCAAA CGTCCAGGCC TTTTGCAGAA GAGATATTTT      8580

TAATTGTGGA CGAATCGAAC TCAGGAACTT GATATTTTTC ATTTTTTTGC TGTTCAGGGA      8640

TTTGCAGCAT ATCATGGCGT GTAATATGGG AAATGCCGTA TGTTTCCTTA TATGGCTTTT      8700

GGTTCGTTTC TTTCGCAAAC GCTTGAGTTG CGCCTCCTGC CAGCAGTGCG GTAGTAAAGG      8760

TTAATACTGT TACTTGTTTT GCAAACTTTT TGATGTTCAT CGTTCATGTC TCCTTTTCTA      8820

TGTACTGTGT TAGCGGTCTG CTTCTTCCAG CCCTCCTGTT TGAAGATGGC AAGTTAGTTA      8880

CGCACAATAA AAAAGACCT AAAATATGTA AGGGGTGACG CCAAAGTATA CACTTTGCCC       8940

TTTACACATT TTAGGTCTTG CCTGCTTTAT CAGTAACAAA CCCGCGCGAT TTACTTTTTG      9000

ACCTCATTCT ATTAGACTCT CGTTTGGATT GCAACTGGTC TATTTTCCTC TTTTGTTTGA      9060

TAGAAAATCA TAAAGGATT TGCAGACTAC GGGCCTAAAG AACTAAAAAA TCTATCTGTT       9120

TCTTTTCATT CTCTGTATTT TTTATAGTTT CTGTTGCATG GCATAAAGT TGCCTTTTTA       9180

ATCACAATTC AGAAAATATC ATAATATCTC ATTTCACTAA ATAATAGAGC TTGGCCGGCG      9240

CCGTCCCGTC AAGTCAGCGT AATGCTCTGC CAGTGTTACA ACCAATTAAC CACGCGTAGG     9300

CGCCATTCGC CATTCAGGCT GCGCAACTGT TGGGAAGGGC GATCGGTGCG GGCCTCTTCG     9360

CTATTACGCC AGCTGGCGAA AGGGGATGT GCTGCAAGGC GATTAAGTTG GGTAACGCCA       9420

GGGTTTTCCC AGTCACGACG TTGTAAAACG ACGGCCAGTG AATTGGCTTT CCCGTAGCTT     9480

GGCGTAATCA TGGTCATAGC TGTTTCCTGT GTGAAATTGT TATCCGCTCA CAATTCCACA     9540

CAACATACGA GCCGGAAGCA TAAAGTGTAA AGCCTGGGGT GCCTAATGAG TGAGCTAACT     9600

CACATTAATT GCGTTGCGCT CACCTAGGCC CCGTAGAAAA GATCAAAGGA TCTTCTTGAG    9660

ATCCTTTTTT TCTGCGCGTA ATCTGCTGCT TGCAAACAAA AAAACCACCG CTACCAGCGG    9720

TGGTTTGTTT GCCGGATCAA GAGCTACCAA CTCTTTTTCC GAAGGTAACT GGCTTCAGCA    9780

GAGCGCAGAT ACCAAATACT GTTCTTCTAG TGTAGCCGTA GTTAGGCCAC CACTTCAAGA    9840

ACTCTGTAGC ACCGCCTACA TACCTCGCTC TGCTAATCCT GTTACCAGTG GCTGCTGCCA    9900

GTGGCGATAA GTCGTGTCTT ACCGGGTTGG ACTCAAGACG ATAGTTACCG GATAAGGCGC     9960

AGCGGTCGGG CTGAACGGGG GGTTCGTGCA CACAGCCCAG CTTGGAGCGA ACGACCTACA    10020

CCGAACTGAG TACTCTACAC GTGAGCTATG AGAAAGCGCC ACGCTTCCCG AAGGGAGAAA    10080

GGCGGACAGG TATCCGGTAA GCGGCAGGGT CGGAACAGGA GAGCGCACGA GGGAGCTTCC    10140

AGGGGGAAAC GCCTGGTATC TTTATAGTCC TGTCGGGTTT CGCCACCTCT GACTTGAGCG    10200

TCGATTTTTG TGATGCTCGT CAGGGGGGCG GAGCCTATGG AAAAACGCCA GCAACGCGGC    10260

CTTTTTACGG TTCCTGGCCT TTTGCTGGCC TTTTGCTCAC ATGTTCTTTC CTGCGCG       10317
```

(2) INFORMATION FOR SEQ ID NO: 2:

(i) SEQUENCE CHARACTERISTICS:
        (A) LENGTH: 9 base pairs
        (B) TYPE: NUCLEIC ACID
        (C) STRANDEDNESS: DOUBLE
        (D) TOPOLOGY: LINEAR (ii) MOLECULE TYPE: synthetic DNA (ix) FEATURE:

```
              (A) NAME/KEY: ID NO:2
              (B) LOCATION: 1..9
              (D) OTHER INFORMATION: Extracted from seq ID1 (10031..10039)

(xi) SEQUENCE DESCRIPTION: SEQ ID NO: 2:

TACTCTACA                                                              9

(2) INFORMATION FOR SEQ ID NO: 3:

(i) SEQUENCE CHARACTERISTICS:
              (A) LENGTH: 32 base pairs
              (B) TYPE: NUCLEIC ACID
              (C) STRANDEDNESS: DOUBLE
              (D) TOPOLOGY: LINEAR (ii) MOLECULE TYPE: synthetic DNA (ix) FEATURE:
              (A) NAME/KEY: ID NO:3
              (B) LOCATION: 1..32
              (D) OTHER INFORMATION: Extracted from seq ID1  (3038..3071)

(xi) SEQUENCE DESCRIPTION: SEQ ID NO: 3:

TGGGGATTAA CCCTCACTAA AGGGACGGCT TT                                   32

(2) INFORMATION FOR SEQ ID NO: 4:

(i) SEQUENCE CHARACTERISTICS:
              (A) LENGTH: 15 base pairs
              (B) TYPE: NUCLEIC ACID
              (C) STRANDEDNESS: DOUBLE
              (D) TOPOLOGY: LINEAR (ii) MOLECULE TYPE: synthetic DNA (ix) FEATURE:
              (A) NAME/KEY: HE1
              (B) LOCATION: 1..15
              (D) OTHER INFORMATION: Extracted from seq ID1
                  compl(9465..9479)

(xi) SEQUENCE DESCRIPTION: SEQ ID NO: 4:

AGCTACGGGA AAGCC                                                      15

(2) INFORMATION FOR SEQ ID NO: 5:

(i) SEQUENCE CHARACTERISTICS:
              (A) LENGTH: 31 base pairs
              (B) TYPE: NUCLEIC ACID
              (C) STRANDEDNESS: DOUBLE
              (D) TOPOLOGY: LINEAR (ii) MOLECULE TYPE: synthetic DNA (ix) FEATURE:
              (A) NAME/KEY: lacLRS2Avr
              (B) LOCATION: 1..31
              (D) OTHER INFORMATION: Extracted from seq ID1
                  compl(9603..9630)

(xi) SEQUENCE DESCRIPTION: SEQ ID NO: 5:

AGTCCTAGGT GAGCGCGCAA CGCAATTAAT G                                    31

(2) INFORMATION FOR SEQ ID NO: 6:

(i) SEQUENCE CHARACTERISTICS:
              (A) LENGTH: 26 base pairs
              (B) TYPE: NUCLEIC ACID
              (C) STRANDEDNESS: DOUBLE
              (D) TOPOLOGY: LINEAR
```

(ii) MOLECULE TYPE: synthetic DNA (ix) FEATURE:
            (A) NAME/KEY: lacE2Mlu
            (B) LOCATION: 1..26
            (D) OTHER INFORMATION: Extracted from seq ID1  (9289..9314)

(xi) SEQUENCE DESCRIPTION: SEQ ID NO: 6:

```
AACACGCGTA GGCGCCATTC GCCATT                                          26
```

(2) INFORMATION FOR SEQ ID NO: 7:

(i) SEQUENCE CHARACTERISTICS:
            (A) LENGTH: 326 base pairs
            (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: ID NO:7
            (B) LOCATION: 1..326
            (D) OTHER INFORMATION: Extracted from seq ID1
                compl(9298..9623)

(xi) SEQUENCE DESCRIPTION: SEQ ID NO: 7:

```
GTGAGCGCAA CGCAATTAAT GTGAGTTAGC TCACTCATTA GGCACCCCAG GCTTTACACT      60

TTATGCTTCC GGCTCGTATG TTGTGTGGAA TTGTGAGCGG ATAACAATTT CACACAGGAA     120

ACAGCT ATG ACC ATG ATT ACG CCA AGC TAC GGG AAA GCC AAT TCA CTG       168
       Met Thr Met Ile Thr Pro Ser Tyr Gly Lys Ala Asn Ser Leu
         1               5                  10

GCC GTC GTT TTA CAA CGT CGT GAC TGG GAA AAC CCT GGC GTT ACC CAA       216
Ala Val Val Leu Gln Arg Arg Asp Trp Glu Asn Pro Gly Val Thr Gln
 15              20                  25                  30

CTT AAT CGC CTT GCA GCA CAT CCC CCT TTC GCC AGC TGG CGT AAT AGC       264
Leu Asn Arg Leu Ala Ala His Pro Pro Phe Ala Ser Trp Arg Asn Ser
                 35                  40                  45

GAA GAG GCC CGC ACC GAT CGC CCT TCC CAA CAG TTG CGC AGC CTG AAT       312
Glu Glu Ala Arg Thr Asp Arg Pro Ser Gln Gln Leu Arg Ser Leu Asn
             50                  55                  60

GGC GAA TGG CGC CT                                                    326
Gly Glu Trp Arg
         65
```

(2) INFORMATION FOR SEQ ID NO: 8:

(i) SEQUENCE CHARACTERISTICS:
            (A) LENGTH: 26 base pairs
            (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: oriLRd
            (B) LOCATION: 1..26
            (D) OTHER INFORMATION: Extracted from seq ID1  (9856..9881)

(xi) SEQUENCE DESCRIPTION: SEQ ID NO: 8:

```
CTACATACCT CGCTCTGCTA ATCCTG                                          26
```

(2) INFORMATION FOR SEQ ID NO: 9:

(i) SEQUENCE CHARACTERISTICS:
            (A) LENGTH: 21 base pairs (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: oriLRr
            (B) LOCATION: 1..21
            (D) OTHER INFORMATION: Extracted from seq ID1 compl (10182..10202)

(xi) SEQUENCE DESCRIPTION: SEQ ID NO: 9:

GACGCTCAAG TCAGAGGTGG C                                                 21

(2) INFORMATION FOR SEQ ID NO: 10:

(i) SEQUENCE CHARACTERISTICS:
            (A) LENGTH: 18 base pairs
            (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: OS1
            (B) LOCATION: 1..18
            (D) OTHER INFORMATION: Extracted from seq ID1  (10009..10026)

(xi) SEQUENCE DESCRIPTION: SEQ ID NO: 10:

GAACGACCTA CACCGAAC                                                     18

(2) INFORMATION FOR SEQ ID NO: 11:

(i) SEQUENCE CHARACTERISTICS:
            (A) LENGTH: 17 base pairs
            (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: OR1
            (B) LOCATION: 1..17
            (D) OTHER INFORMATION: complementary strand (xi) SEQUENCE DESCRIPTION: SEQ ID NO: 11:

GTGGCGCTTT CTCATAG                                                      17

(2) INFORMATION FOR SEQ ID NO: 12:

(i) SEQUENCE CHARACTERISTICS:
            (A) LENGTH: 20 base pairs
            (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: rpsLR
            (B) LOCATION: 1..20
            (D) OTHER INFORMATION: Extracted from seq ID1  (7155..7174)

(xi) SEQUENCE DESCRIPTION: SEQ ID NO: 12:

AGGACGCCGA ATTTTAGGGC                                                   20

(2) INFORMATION FOR SEQ ID NO: 13:

(i) SEQUENCE CHARACTERISTICS:

```
        (A) LENGTH: 19 base pairs
        (B) TYPE: NUCLEIC ACID
        (C) STRANDEDNESS: DOUBLE
        (D) TOPOLOGY: LINEAR (ii) MOLECULE TYPE: synthetic DNA (ix) FEATURE:
        (A) NAME/KEY: SP6
        (B) LOCATION: 1..19
        (D) OTHER INFORMATION: Extracted from seq ID1  (7230..7248)

(xi) SEQUENCE DESCRIPTION: SEQ ID NO: 13:

GATTTAGGTG ACACTATAG                                                  19

(2) INFORMATION FOR SEQ ID NO: 14:

(i) SEQUENCE CHARACTERISTICS:
        (A) LENGTH: 20 base pairs
        (B) TYPE: NUCLEIC ACID
        (C) STRANDEDNESS: DOUBLE
        (D) TOPOLOGY: LINEAR (ii) MOLECULE TYPE: synthetic DNA (ix) FEATURE:
        (A) NAME/KEY: SLR3
        (B) LOCATION: 1..20
        (D) OTHER INFORMATION: Extracted from seq ID1  (8711..8731)

(xi) SEQUENCE DESCRIPTION: SEQ ID NO: 14:

TTTCGCGAAG GCTTGAGTCG                                                 20

(2) INFORMATION FOR SEQ ID NO: 15:

(i) SEQUENCE CHARACTERISTICS:
        (A) LENGTH: 25 base pairs
        (B) TYPE: NUCLEIC ACID
        (C) STRANDEDNESS: DOUBLE
        (D) TOPOLOGY: LINEAR (ii) MOLECULE TYPE: synthetic DNA (ix) FEATURE:
        (A) NAME/KEY: LRT3RA
        (B) LOCATION: 1..25
        (D) OTHER INFORMATION: Extracted from seq ID1
            compl(3045..3069)

(xi) SEQUENCE DESCRIPTION: SEQ ID NO: 15:

AAAGCCGTCC CTTTAGTGAG GGTTA                                           25

(2) INFORMATION FOR SEQ ID NO: 16:

(i) SEQUENCE CHARACTERISTICS:
        (A) LENGTH: 22 base pairs
        (B) TYPE: NUCLEIC ACID
        (C) STRANDEDNESS: DOUBLE
        (D) TOPOLOGY: LINEAR (ii) MOLECULE TYPE: synthetic DNA (ix) FEATURE:
        (A) NAME/KEY: RepELR
        (B) LOCATION: 1..22
        (D) OTHER INFORMATION: Extracted from seq ID1  (2897..2918)

(xi) SEQUENCE DESCRIPTION: SEQ ID NO: 16:

CGCTTCCTGC AGGTCTGTGT TA                                              22

(2) INFORMATION FOR SEQ ID NO: 17:
```

(i) SEQUENCE CHARACTERISTICS:
            (A) LENGTH: 17 base pairs
            (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: T3
            (B) LOCATION: 1..17
            (D) OTHER INFORMATION: Extracted from seq ID1  (3043..3059)

(xi) SEQUENCE DESCRIPTION: SEQ ID NO: 17:

ATTAACCCTC ACTAAAG                                                    17

(2) INFORMATION FOR SEQ ID NO: 18:

(i) SEQUENCE CHARACTERISTICS:
            (A) LENGTH: 688 base pairs
            (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: modified replication origin for pGenbacEcoRI
            (B) LOCATION: 1..688

(ix) FEATURE:
            (A) NAME/KEY: EcoRI site
            (B) LOCATION: 408..413

(xi) SEQUENCE DESCRIPTION: SEQ ID NO: 18:

CCCCGTAGAA AAGATCAAAG GATCTTCTTG AGATCCTTTT TTTCTGCGCG TAATCTGCTG       60

CTTGCAAACA AAAAAACCAC CGCTACCAGC GGTGGTTTGT TTGCCGGATC AAGAGCTACC      120

AACTCTTTTT CCGAAGGTAA CTGGCTTCAG CAGAGCGCAG ATACCAAATA CTGTCCTTCT      180

AGTGTAGCCG TAGTTAGGCC ACCACTTCAA GAACTCTGTA GCACCGCCTA CATACCTCGC      240

TCTGCTAATC CTGTTACCAG TGGCTGCTGC CAGTGGCGAT AAGTCGTGTC TTACCGGGTT      300

GGACTCAAGA CGATAGTTAC CGGATAAGGC GCAGCGGTCG GGCTGAACGG GGGGTTCGTG      360

CACACAGCCC AGCTTGGAGC GAACGACCTA CACCGAACTG AGATACCGAA TTCGTGAGCT      420

ATGAGAAAGC GCCACGCTTC CCGAAGGGAG AAAGGCGGAC AGGTATCCGG TAAGCGGCAG      480

GGTCGGAACA GGAGAGCGCA CGAGGGAGCT TCCAGGGGGA AACGCCTGGT ATCTTTATAG      540

TCCTGTCGGG TTTCGCCACC TCTGACTTGA GCGTCGATTT TTGTGATGCT CGTCAGGGGG      600

GCGGAGCCTA TGGAAAAACG CCAGCAACGC GGCCTTTTTA CGGTTCCTGG CCTTTTGCTG      660

GCCTTTTGCT CACATGTTCT TTCCTGCG                                        688

(2) INFORMATION FOR SEQ ID NO: 19:

(i) SEQUENCE CHARACTERISTICS:
            (A) LENGTH: 688 base pairs
            (B) TYPE: NUCLEIC ACID
            (C) STRANDEDNESS: DOUBLE
            (D) TOPOLOGY: LINEAR (ii) MOLECULE TYPE: synthetic DNA (ix) FEATURE:
            (A) NAME/KEY: modified replication origin for pGenBacBamHI
            (B) LOCATION: 1..688

(ix) FEATURE:

(A) NAME/KEY: BamHI site
            (B) LOCATION: 408..413

(xi) SEQUENCE DESCRIPTION: SEQ ID NO: 19:

CCCCGTAGAA AAGATCAAAG GATCTTCTTG AGATCCTTTT TTTCTGCGCG TAATCTGCTG      60

CTTGCAAACA AAAAAACCAC CGCTACCAGC GGTGGTTTGT TTGCCGGATC AAGAGCTACC     120

AACTCTTTTT CCGAAGGTAA CTGGCTTCAG CAGAGCGCAG ATACCAAATA CTGTCCTTCT     180

AGTGTAGCCG TAGTTAGGCC ACCACTTCAA GAACTCTGTA GCACCGCCTA CATACCTCGC     240

TCTGCTAATC CTGTTACCAG TGGCTGCTGC CAGTGGCGAT AAGTCGTGTC TTACCGGGTT     300

GGACTCAAGA CGATAGTTAC CGGATAAGGC GCAGCGGTCG GGCTGAACGG GGGGTTCGTG     360

CACACAGCCC AGCTTGGAGC GAACGACCTA CACCGAACTG AGATACCGGA TCCGTGAGCT     420

ATGAGAAAGC GCCACGCTTC CCGAAGGGAG AAAGGCGGAC AGGTATCCGG TAAGCGGCAG     480

GGTCGGAACA GGAGAGCGCA CGAGGGAGCT TCCAGGGGGA AACGCCTGGT ATCTTTATAG     540

TCCTGTCGGG TTTCGCCACC TCTGACTTGA GCGTCGATTT TTGTGATGCT CGTCAGGGGG     600

GCGGAGCCTA TGGAAAAACG CCAGCAACGC GGCCTTTTTA CGGTTCCTGG CCTTTTGCTG     660

GCCTTTTGCT CACATGTTCT TTCCTGCG                                        688

(2) INFORMATION FOR SEQ ID NO: 20:

(i) SEQUENCE CHARACTERISTICS:
        (A) LENGTH: 15 base pairs
        (B) TYPE: NUCLEIC ACID
        (C) STRANDEDNESS: DOUBLE
        (D) TOPOLOGY: LINEAR (ii) MOLECULE TYPE: synthetic DNA (ix) FEATURE:
        (A) NAME/KEY: HE2
        (B) LOCATION: 1..15
        (D) OTHER INFORMATION: Extracted from seq ID1  (9461..9475)

(xi) SEQUENCE DESCRIPTION: SEQ ID NO: 20:

AATTGGCTTT CCCGT                                                       15

(2) INFORMATION FOR SEQ ID NO: 21:

(i) SEQUENCE CHARACTERISTICS:
        (A) LENGTH: 20 base pairs
        (B) TYPE: NUCLEIC ACID
        (C) STRANDEDNESS: DOUBLE
        (D) TOPOLOGY: LINEAR (ii) MOLECULE TYPE: synthetic DNA (ix) FEATURE:
        (A) NAME/KEY: g621d
        (B) LOCATION: 1..20

(xi) SEQUENCE DESCRIPTION: SEQ ID NO: 21:

GCAGAGAAGT AAGCCTTCAA                                                  20

(2) INFORMATION FOR SEQ ID NO: 22:

(i) SEQUENCE CHARACTERISTICS:
        (A) LENGTH: 21 base pairs
        (B) TYPE: NUCLEIC ACID
        (C) STRANDEDNESS: DOUBLE
        (D) TOPOLOGY: LINEAR (ii) MOLECULE TYPE: synthetic DNA -continued

```
    (ix) FEATURE:
         (A) NAME/KEY: g621r
         (B) LOCATION: 1..21

(xi) SEQUENCE DESCRIPTION: SEQ ID NO: 22:

AGAGGTCTCA GTAACCAGAC C                                              21
```

HIGH THROUGHPUT DNA SEQUENCING VECTOR

RELATED APPLICATIONS

The present application is divisional of U.S. patent application Ser. No. 09/438,142, filed Nov. 10, 1999, now U.S. Pat. No. 6,258,571, which was a continuation of U.S. patent application Ser. No. 09/058,746, now U.S. Pat. No. 6,022,716, filed Apr. 10, 1998, the disclosures of which are incorporated herein by reference in their entireties.

BACKGROUND OF THE INVENTION

The science of molecular biology has progressed rapidly to the point where characterization and sequencing of the entire genome of an organism is feasible. However, at the present time, the characterization and sequencing of large genomes is labor intensive and requires the sequencing of each region of the genome multiple times in order to obtain a complete, contiguous sequence.

Currently, several strategies are available for sequencing large genomes. In the shotgun sequencing method, the genome is randomly fragmented and cloned into sequencing vectors. The resulting clones are sequenced and overlapping sequences are identified and ordered to generate a contiguous sequence. Using this approach, high quality sequence can only be assembled after very large amounts of sequence data, ranging from five to seven times the amount of raw data to be sequenced, are accumulated. Even after such extensive over-sequencing, primer walking is required for final gap closure.

As an alternative to both shotgun and primer walking, nested deletion strategies provide an economic means of determining the primary structure of DNA. Nested deletion strategies produce an array of clones with overlapping deletions which are anchored at one end (i.e. all the deletions share one undeleted end in common). Contig assembly through nested deletion methodology is much simpler than in the case of a shotgun approach, and two to three times less raw sequence information is needed.

Enzymatic methods represent one approach to generating nested deletions. Enzymatic methods used to generate nested deletions include exonuclease treatment of double stranded DNA, using enzymes such as double stranded exonuclease Bal31 [Guo, L. H., Yang R. C., and Wu R., Nucleic Acids Research 11 (16): 5521–5540 (1983)], or the more widely used exonuclease III [Henikoff, S. An improved strategy for rapid direct sequencing of both strands of long DNA molecules cloned in a plasmid, Gene 28, 351–359 (1984)]. These methods provide good templates for sequencing but require large quantities of high quality, i.e. pure, non-nicked, DNA since exonuclease extension of gaps from potential pre-existing nicks would give rise to aberrant sub-clones. In addition, the current enzymatic methods for producing nested deletions require numerous bacterial transformation steps in order to produce a set of minimally overlapping clones. The number of bacterial transformations necessary to conduct the exonuclease methods is directly proportional to the size of the insert to be sequenced, with one transformation required per 300–400 basepairs to be sequenced.

Alternatively, transposition based methods may also be used to generate nested deletions. The methods based on transposition employ the in vivo capacity of clones to undergo either intermolecular [J Mol Biol 178 (4): 941–948 (1984) Use of transposon-promoted deletions in DNA sequence analysis. Ahmed A] or intramolecular [Proc Natl Acad Sci USA 90 (16): 7874–7878 (1993) pDUAL: a transposon-based cosmid cloning vector for generating nested deletions and DNA sequencing templates in vivo. Wang G, Blakesley R W, Berg D E, Berg C M] transpositions, achieving a deletion joining one end of the transposon to a random site within the target DNA sequence. These methods greatly reduce the number of manipulations necessary to produce high quality data. Still, the existing transposon-based vectors designed for sequencing require significant efforts both for initial cloning and for generating subsequent sub-clones. Almost all of such existing vectors are high copy number, relatively unstable plasmids, which do not permit the sequence determination of numerous regions of eucaryotic genomes, which are unclonable when present in multiple copies. After the initial cloning step, the resulting recombinant cells have to be transformed with a transposase-containing plasmid. Furthermore, after transposase action, another cycle of retransformation is obligatory in order to obtain pure subclones, harboring one single transposon-mediated deletion. These factors restrict the number of regions that can be processed simultaneously.

The present invention concerns a new vector for sequencing and mapping large regions of eucaryotic DNA using enzymatic and/or transposition based methods for generating nested deletions. New techniques for sequencing large regions of DNA and mapping the locations of markers within large regions of DNA are also provided.

SUMMARY OF THE INVENTION

The present invention relates to vectors for maintaining inserts at low copy number and vectors for constructing deletions in DNA inserts. One embodiment of the present invention is a vector comprising a high copy number origin of replication having at least one cloning site therein, a low copy number origin of replication, at least one copy number indicator for indicating the copy number of the vector in cells, and a vector maintenance marker for selecting cells containing the vector, wherein the at least one cloning site is positioned in the high copy number origin of replication such that the ability of the high copy number origin of replication to direct replication is not disrupted when no insert has been cloned into the at least one cloning site and is disrupted when an insert is cloned into the at least one cloning site.

In one aspect of the above embodiment, the vector further comprises a single stranded origin of replication which permits the isolation of the vector in a single stranded form.

In another aspect of the above embodiment, the high copy number origin of replication and the low copy number origin of replication comprise separate origins of replication.

In yet another aspect of the above embodiment, the high copy number origin of replication and the low copy number origin of replication comprise a single origin of replication and cloning of an insert into the at least one restriction site converts the single origin of replication from a high copy number origin of replication to a low copy number origin of replication.

In still another aspect of the above embodiment, the at least one copy number indicator comprises a selectable marker which permits the selection of cells in which the vector is present at a low copy number as a result of the cloning of an insert into the cloning site in the high copy number origin of replication.

In still another aspect of this embodiment, the vector further comprises at least one deletion indicator for indicating whether a deletion has been generated in an insert which has been cloned into the at least one cloning site in the high copy number origin of replication.

In some aspects of the above embodiment, the vector is a transposition-based deletion vector. In this aspect of the above embodiment, the transposition-based deletion vectors may further comprise transposition elements positioned on each side of the at least one cloning site in the high copy number origin of replication. The transposition elements are adapted for generating deletions in the insert.

The high copy number origin of replication in the transposition-based deletion vectors may comprise a ColE1-derived origin of replication.

For example, the ColE-1 derived origin of replication in the transposition-based deletion vectors may comprise the pUC19 origin of replication.

In some aspects of the transposition-based deletion vectors, the low copy number origin of replication comprises oriS.

In other aspects of the transposition-based deletion vectors, the at least one copy number indicator comprises a selectable marker which permits the selection of cells in which the vector is present at a low copy number as a result of the cloning of an insert into the cloning site in the high copy number origin of replication.

For example, the at least one copy number indicator in the transposition-based deletion vectors may comprise a truncated LacZ gene for distinguishing cells carrying the truncated form of the LacZ gene at a high copy number from cells carrying the truncated form of the LacZ gene at a low copy number. In this aspect of the present invention, cells containing the truncated lacZ gene at high copy number are dark blue when grown on medium containing Xgal and IPTG and cells containing the truncated LacZ gene at low copy number are light blue when grown on medium containing Xgal and IPTG.

In other aspects of the present invention, the at least one copy number indicator in the transposition-based deletion vectors comprises the strA+ gene.

In still other aspects of the transposition-based deletion vectors, the at least one copy number indicator comprises both the strA+ gene and a truncated LacZ gene for distinguishing cells carrying the truncated form of the LacZ gene at a high copy number from cells carrying the truncated form of the LacZ gene at a low copy number. In this aspect, cells containing the truncated lacZ gene at high copy number are dark blue when grown on medium containing Xgal and IPTG and cells containing the truncated LacZ gene at low copy number are light blue when grown on medium containing Xgal and IPTG.

In some aspects of the transposition-based deletion vectors, the vector maintenance marker comprises a gene encoding drug resistance.

In other aspects of the transposition-based deletion vectors, the truncated lacZ gene also functions as a deletion indicator.

In still further aspects of the transposition-based deletion vectors, the at least one deletion indicator comprises the sacB gene.

In other aspects of the transposition-based deletion vectors, the at least one deletion indicator comprises both the sacB gene and a truncated LacZ gene for distinguishing cells carrying the truncated form of the LacZ gene at a high copy number from cells carrying the truncated form of the LacZ gene at a low copy number. In this aspect, cells containing the truncated lacZ gene at high copy number are dark blue when grown on medium containing Xgal and IPTG and cells containing the truncated LacZ gene at low copy number are light blue when grown on medium containing Xgal and IPTG.

In other aspects of the transposition-based deletion vectors, the vectors further comprise hybridization sites for insert sequencing primers. The hybridization sites for insert sequencing primers are positioned on each side of the cloning sites in the high copy number origin of replication so as to allow the sequencing of inserts cloned into the at least one cloning site of the vector.

In other aspects of the transposition-based deletion vectors, the vector further comprises hybridization sites for insert amplification primers. The hybridization sites for insert amplification primers are located on each side of the cloning sites in the high copy number origin of replication such that an amplification reaction conducted with the insert amplification primers will produce an amplification product containing the insert.

In other aspects of the transposition-based deletion vectors, the hybridization sites for insert sequencing primers are located internally to the hybridization sites for insert amplification primers such that the insert sequencing primers can hybridize to the amplification product.

In other aspects of the transposition-based deletion vectors, the vectors further comprise hybridization sites for deletion amplification primers. The hybridization sites for deletion amplification primers are positioned such that an amplification reaction with the deletion amplification primers will produce an amplification product containing deleted inserts resulting from a transposition event.

In still other aspect of the transposition-based deletion vectors, the vectors further comprise hybridization sites for primers for sequencing the end of the deleted insert in which the deletion was made.

In still other aspects of the transposition-based deletion vectors, the hybridization sites for primers for sequencing the end of the deleted insert in which the deletion was made are positioned internally to the hybridization sites for deletion amplification products such that the primers for sequencing the end of the deleted insert in which the deletion was made can hybridize to the amplification product produced with the deletion amplification primers.

In still further aspects of the transposition-based deletion vectors, the transposition elements comprise the leftmost 39 base pairs of Tn1000 and the inverted rightmost 39 base pairs of Tn1000.

Enzymatic deletions vectors are another aspect of the present invention. The enzymatic deletion vectors comprise a high copy number origin of replication having at least one cloning site therein, a low copy number origin of replication, at least one copy number indicator for indicating the copy number of the vector in cells, and a vector maintenance marker for selecting cells containing the vector, wherein the at least one cloning site is positioned in the high copy number origin of replication such that the ability of the high copy number origin of replication to direct replication is not disrupted when no insert has been cloned into the at least one cloning site and is disrupted when an insert is cloned into the at least one cloning site. In addition, the enzymatic deletion vectors further comprise hybridization sites for primers for generating enzymatic deletions. The hybridization sites for primers for generating enzymatic deletions are positioned such that the product of an amplification reaction with the primers for generating enzymatic deletions contains the low copy number origin of replication, the vector maintenance marker, the insert, and the deletion indicator.

In one aspect of the enzymatic deletion vectors, one of the hybridization sites for a primer for generating enzymatic deletions is adapted to facilitate unidirectional deletion of the amplification product when the amplification product is treated with Exonuclease III.

In another aspect, the enzymatic deletion vectors further comprise hybridization sites for amplification primers for generating sequencing templates from enzymatic deletions. The hybridization sites for amplification primers for generating sequencing templates from enzymatic deletions are positioned such that an amplification reaction with the amplification primers for generating sequencing templates from enzymatic deletions will produce an amplification product containing deleted inserts produced by enzymatic deletion of the amplification product from the primers for generating enzymatic deletions.

In still another aspect of the invention, the enzymatic deletion vectors further comprise hybridization sites for primers for sequencing the end of the deleted insert in which the deletion was made.

In another aspect of the enzymatic deletion vectors, the hybridization sites for primers for sequencing the end of the deleted insert in which the deletion was made are positioned internally to the hybridization sites for the amplification primers for generating sequencing templates from enzymatic deletions such that the primers for sequencing the end of the deleted insert in which the deletion was made can hybridize to the amplification product produced with the amplification primers for generating sequencing templates from enzymatic deletions.

The enzymatic deletion vectors may further comprise hybridization sites for insert sequencing primers. The hybridization sites are positioned on each side of the cloning sites in the high copy number origin of replication so as to allow the sequencing of inserts cloned into the at least one cloning site of the vector.

In still another aspect of the enzymatic deletion vectors, the vectors further comprise hybridization sites for insert amplification primers. The hybridization sites for insert amplification primers are located on each side of the cloning sites in the high copy number origin of replication such that an amplification reaction conducted with the insert amplification primers will produce an amplification product containing the insert.

In one aspect of the enzymatic deletion vectors, the hybridization sites for insert sequencing primers are located internally to the hybridization sites for insert amplification primers such that the insert sequencing primers can hybridize to the amplification product.

In another aspect of the enzymatic deletion vectors, the high copy number origin of replication comprises a ColE1-derived origin of replication.

For example, the ColE-1 derived origin of replication may comprise the pUC19 origin of replication.

In a further aspect of the enzymatic deletion vectors, the low copy number origin of replication comprises oriS.

In another aspect of the enzymatic deletion vectors, the at least one copy number indicator comprises a truncated LacZ gene for distinguishing cells carrying the truncated form of the LacZ gene at a high copy number from cells carrying the truncated form of the LacZ gene at a low copy number. In this aspect, cells containing the truncated lacZ gene at high copy number are dark blue when grown on medium containing Xgal and IPTG and cells containing the truncated LacZ gene at low copy number are light blue when grown on medium containing Xgal and IPTG.

In a further aspect of the enzymatic deletion vectors, the at least one copy number indicator comprises the strA+ gene.

In another aspect of the enzymatic deletion vectors, the at least one copy number indicator comprises both the strA+ gene and a truncated LacZ gene for distinguishing cells carrying the truncated form of the LacZ gene at a high copy number from cells carrying the truncated form of the LacZ gene at a low copy number. In this aspect, cells containing the truncated lacZ gene at high copy number are dark blue when grown on medium containing Xgal and IPTG and cells containing the truncated LacZ gene at low copy number are light blue when grown on medium containing Xgal and IPTG.

In still another aspect of the enzymatic deletion vectors, the vector maintenance marker comprises a gene encoding drug resistance.

In a further aspect of the enzymatic deletion vectors, the deletion indicator comprises a truncated LacZ gene for distinguishing cells carrying the truncated form of the LacZ gene at a high copy number from cells carrying the truncated form of the LacZ gene at a low copy number. In this aspect, cells containing the truncated lacZ gene at high copy number are dark blue when grown on medium containing Xgal and IPTG and cells containing the truncated LacZ gene at low copy number are light blue when grown on medium containing Xgal and IPTG.

In another aspect of the enzymatic deletion vectors, a hybridization site for one of the primers for generating enzymatic deletions is adapted to hybridize to a primer having the sequence of SEQ ID NO:14.

In a further aspect of the enzymatic deletion vectors, a hybridization site for one of the primers for generating enzymatic deletions is adapted to hybridize to a primer having the sequence of SEQ ID NO:15.

Another aspect of the present invention relates to enzymatic/transposition-based deletion vectors. These vectors comprise a high copy number origin of replication having at least one cloning site therein, a low copy number origin of replication, at least one copy number indicator for indicating the copy number of the vector in cells, and a vector maintenance marker for selecting cells containing the vector, wherein the at least one cloning site is positioned in the high copy number origin of replication such that the ability of the high copy number origin of replication to direct replication is not disrupted when no insert has been cloned into the at least one cloning site and is disrupted when an insert is cloned into the at least one cloning site. The enzymatic/transposition-based deletion vectors also comprise hybridization sites for primers for generating enzymatic deletions. The hybridization sites for primers for generating enzymatic deletions are positioned such that the product of an amplification reaction with the primers for generating enzymatic deletions contains the low copy number origin of replication, the vector maintenance marker, the insert, and the deletion indicator. In addition, the enzymatic/transposition-based deletion vectors further comprise transposition elements. The transposition elements are positioned on each side of the at least one cloning site in the high copy number origin of replication. The transposition elements are adapted for generating deletions in the insert.

In one aspect of the enzymatic/transposition-based deletion vectors, one of the hybridization sites for a primer for generating enzymatic deletions is adapted to facilitate unidirectional deletion of the amplification product when the amplification product is treated with Exonuclease III.

In another aspect of the enzymatic/transposition-based deletion vectors, the high copy number origin of replication comprises a ColE1-derived origin of replication.

For example, the ColE1-derived origin of replication may comprise the pUC19 origin of replication.

In still another aspect of the enzymatic/transposition-based deletion vectors, the low copy number origin of replication comprises oriS.

In another aspect of the enzymatic/transposition-based deletion vectors, the at least one copy number indicator comprises a truncated LacZ gene for distinguishing cells carrying the truncated form of the LacZ gene at a high copy number from cells carrying the truncated form of the LacZ gene at a low copy number. In this aspect, cells containing the truncated lacZ gene at high copy number are dark blue when grown on medium containing Xgal and IPTG and cells containing the truncated LacZ gene at low copy number are light blue when grown on medium containing Xgal and IPTG.

In a further aspect of the enzymatic/transposition-based deletion vectors, the at least one copy number indicator comprises the strA+ gene.

In still another aspect of the enzymatic/transposition-based deletion vectors, the at least one copy number indicator comprises both the strA+ gene and a truncated LacZ gene for distinguishing cells carrying the truncated form of the LacZ gene at a high copy number from cells carrying the truncated form of the LacZ gene at a low copy number. In this aspect, wherein cells containing the truncated lacZ gene at high copy number are dark blue when grown on medium containing Xgal and IPTG and cells containing the truncated LacZ gene at low copy number are light blue when grown on medium containing Xgal and IPTG.

In still a further aspect of the enzymatic/transposition-based deletion vectors, the maintenance marker comprises a gene encoding drug resistance.

In yet another aspect of the enzymatic/transposition-based deletion vectors, the truncated lacZ gene also functions as a deletion indicator.

In another aspect of the enzymatic/transposition-based deletion vectors, the at least one deletion indicator comprises the sacB gene.

In still another aspect of the enzymatic/transposition-based deletion vectors, the at least one deletion indicator comprises both the sacB gene and a truncated LacZ gene for distinguishing cells carrying the truncated form of the LacZ gene at a high copy number from cells carrying the truncated form of the LacZ gene at a low copy number. In this aspect, wherein cells containing the truncated lacZ gene at high copy number are dark blue when grown on medium containing Xgal and IPTG and cells containing the truncated LacZ gene at low copy number are light blue when grown on medium containing Xgal and IPTG.

In another aspect of the enzymatic/transposition-based deletion vectors, the vector further comprises hybridization sites for insert sequencing primers. The hybridization sites for insert sequencing primers are positioned on each side of the cloning sites in the high copy number origin of replication so as to allow the sequencing of inserts cloned into the at least one cloning site of the vector.

In still another aspect of the enzymatic/transposition-based deletion vectors, the vectors further comprise hybridization sites for insert amplification primers. The hybridization sites for insert amplification primers are located on each side of the cloning sites in the high copy number origin of replication such that an amplification reaction conducted with the insert amplification primers will produce an amplification product containing the insert.

In a further aspect of the enzymatic/transposition-based deletion vectors, the hybridization sites for insert sequencing primers are located internally to the hybridization sites for insert amplification primers such that the insert sequencing primers can hybridize to the amplification product.

In another aspect of the enzymatic/transposition-based deletion vectors, the vectors further comprise hybridization sites for deletion amplification primers. The hybridization sites for deletion amplification primers are positioned such that an amplification reaction with the deletion amplification primers will produce an amplification product containing deleted inserts resulting from a transposition event.

In yet another aspect of the enzymatic/transposition-based deletion vectors, the vectors further comprise hybridization sites for primers for sequencing the end of the deleted insert in which the deletion was made.

In still another aspect of the enzymatic/transposition-based deletion vectors, the hybridization sites for primers for sequencing the end of the deleted insert in which the deletion was made are positioned internally to the hybridization sites for deletion amplification products such that the primers for sequencing the end of the deleted insert in which the deletion was made can hybridize to the amplification product produced with the deletion amplification primers.

In still another aspect of the enzymatic/transposition-based deletion vectors, transposition elements comprise the leftmost 39 base pairs of Tn1000 and the inverted rightmost 39 base pairs of Tn1000.

In another aspect of the enzymatic/transposition-based deletion vectors, a hybridization site for one of the primers for generating enzymatic deletions is adapted to hybridize to a primer having the sequence of SEQ ID NO:14.

In yet another aspect of the enzymatic/transposition-based deletion vectors, a hybridization site for one of the primers for generating enzymatic deletions is adapted to hybridize to a primer having the sequence of SEQ ID NO:15.

Another embodiment of the present invention is a truncated LacZ gene for distinguishing cells carrying the truncated form of the LacZ gene at a high copy number from cells carrying the truncated form of the LacZ gene at a low copy number, wherein cells containing the truncated lacZ gene at high copy number are dark blue when grown on medium containing Xgal and IPTG and cells containing the truncated LacZ gene at low copy number are light blue when grown on medium containing Xgal and IPTG.

In one aspect of the truncated LacZ gene, the truncated lacZ gene encodes a polypeptide consisting essentially of the polypeptide encoded by the sequence of SEQ ID NO:7.

In another aspect, the truncated lacZ gene consists essentially of the sequence of SEQ ID NO:7.

A further embodiment of the present invention is a vector comprising the sequence of SEQ ID NO:1.

Yet another embodiment of the present invention is an oligonucleotide comprising the sequence of SEQ ID NO:14.

Another embodiment of the present invention is an oligonucleotide comprising the sequence of SEQ ID NO:15.

Still another embodiment of the present invention is a method of constructing a contig containing the complete sequence of a piece of DNA comprising the steps of subcloning fragments of the piece of DNA, obtaining the complete sequence of a portion of the subcloned fragments, obtaining the sequence of the ends of the remainder of the subcloned fragments, identifying overlapping subclones to construct one or more scaffolds covering the complete sequence of the piece of DNA, and completely sequencing the overlapping subclones.

In one aspect of this method, the subclones represent about 10 insert equivalents of the piece of DNA.

In another aspect of this method, the step of obtaining the complete sequence of a portion of the subcloned fragments comprises obtaining the complete sequence of about 10 percent of the subcloned fragments.

In still a further aspect of this method, the overlapping set of subclones comprises about 1 to about 5 insert equivalents.

In another aspect of this method, the overlapping set of subclones comprises about 2.5 insert equivalents.

In still another aspect of the method, the step of subcloning fragments of the piece of DNA comprises subcloning fragments of the piece of DNA into a vector comprising a high copy number origin of replication having at least one cloning site therein, a low copy number origin of replication, at least one copy number indicator for indicating the copy number of the vector in cells, and a vector maintenance marker for selecting cells containing the vector, wherein the at least one cloning site is positioned in the high copy number origin of replication such that the ability of the high copy number origin of replication to direct replication is not disrupted when no insert has been cloned into the at least one cloning site and is disrupted when an insert is cloned into the at least one cloning site.

Yet another embodiment of the present invention is a method of determining the position of a marker in an insert in a vector comprising making a set of nested deletions in the insert, the set of nested deletions having a common undeleted end, and determining whether the marker is present in each member of the set of nested deletions.

In one aspect of this method, the step of making a set of nested deletions in the insert comprises making the nested deletions in an insert in a vector comprising a high copy number origin of replication having at least one cloning site therein, a low copy number origin of replication, at least one copy number indicator for indicating the copy number of the vector in cells, and a vector maintenance marker for selecting cells containing the vector, wherein the at least one cloning site is positioned in the high copy number origin of replication such that the ability of the high copy number origin of replication to direct replication is not disrupted when no insert has been cloned into the at least one cloning site and is disrupted when an insert is cloned into the at least one cloning site.

In another aspect of this method, the presence of the marker is determined by conducting an amplification reaction on each member of the set of nested deletions using primers specific for the marker and determining whether an amplification product is produced.

Yet another embodiment of the present invention is a method of generating a deletion in an insert. A linear piece of vector DNA comprising an origin of replication, a deletion indicator, an insert in which it is desired to make deletions, a deletion indicator, and a vector maintenance marker is obtained. Deleted vectors are generated by contacting the linear piece of vector DNA with a solution consisting essentially of mung bean nuclease. The deleted vectors are circularized. The circularized deleted vectors are introduced into cells. Cells carrying deleted vectors in which a portion of the of the insert is deleted and the origin of replication is not deleted are identified.

In one aspect of this method, the origin of replication is at a first end of the linear piece of vector DNA, the deletion indicator is at a second end of the linear piece of vector DNA, the insert is adjacent to the deletion indicator, and the vector maintenance marker is adjacent to the origin of replication.

In another aspect of this method, the origin of replication comprises a low copy number origin of replication.

Another embodiment of the present invention is a method of isolating deletions in an insert. A vector is obtained which comprises a high copy number origin of replication having at least one cloning site therein which is positioned in the high copy number origin of replication such that the ability of the high copy number origin of replication to direct replication is not disrupted when no insert has been cloned into the at least one cloning site and is disrupted when an insert is cloned into the at least one cloning site. The vector also comprises a low copy number origin of replication and transposition elements positioned on each side of the at least one cloning site in the high copy number origin of replication, the transposition elements adapted for generating deletions in the insert. In addition, the vector comprises at least one deletion indicator for indicating whether a deletion has been generated in an insert which has been cloned into the at least one cloning site in the high copy number origin of replication, at least one copy number indicator for indicating the copy number of the vector in cells, and a vector maintenance marker for selecting cells containing the vector. An insert is cloned into the at least one cloning site in the high copy number origin of replication, thereby causing the vector to replicate at low copy number. The vector having the insert therein is introduced into host cells which are permissive for transposition. Host cells in which a transposition event has generated a deletion in the insert are identified.

In another aspect of the method, the identification step comprises selecting cells having a deletion in the insert using a selectable marker.

In still another aspect of the method, the identification step comprises selecting cells which are sucrose resistant.

Another embodiment of the present invention is a method of generating deletions in an insert. A vector is obtained which comprises a high copy number origin of replication having at least one cloning site therein which is positioned in the high copy number origin of replication such that the ability of the high copy number origin of replication to direct replication is not disrupted when no insert has been cloned into the at least one cloning site and is disrupted when an insert is cloned into the at least one cloning site. The vector also comprises a low copy number origin of replication and at least one deletion indicator for indicating whether a deletion has been generated in an insert which has been cloned into the at least one cloning site in the high copy number origin of replication. In addition, the vector comprises at least one copy number indicator for indicating the copy number of the vector in cells, a vector maintenance marker for selecting cells containing the vector, and hybridization sites for primers for generating enzymatic deletions. The hybridization sites for primers for generating enzymatic deletions are positioned such that the product of an amplification reaction with the primers for generating enzymatic deletions contains the low copy number origin of replication, the vector maintenance marker, the insert, and the deletion indicator. An insert is cloned into the at least one cloning site in the high copy number origin of replication, thereby causing the vector to replicate at low copy number. An amplification reaction is performed with the primers for generating enzymatic deletions, thereby generating an amplification product containing the low copy number origin of replication, the vector maintenance marker, the insert, and the deletion indicator. The amplification product is contacted with an exonuclease to generate deletions therein. The amplification products having deletions therein are recircularized. The recircularized amplification product is introduced into host cells, and host cells containing vectors having deletions in the insert are identified.

In one aspect of this method, the contacting step comprises contacting the amplification product with Exonuclease III.

In another aspect of this method, the contacting step comprises contacting the amplification product with mung bean nuclease.

Another embodiment of the present invention is a recombinant high copy number origin of replication having at least one cloning site introduced therein. The cloning site is positioned in the high copy number origin of replication such that the ability of the high copy number origin of replication to direct replication is not disrupted when no insert has been cloned into the at least one cloning site and is disrupted when an insert is cloned into the at least one cloning site.

In one aspect, the recombinant origin of replication comprises a ColE1-derived origin of replication.

In another aspect, the recombinant origin of replication comprises the pUC19 origin of replication.

In still another aspect, the recombinant origin comprises the sequence of SEQ ID NO: 18 or the sequence complementary thereto.

In another aspect, the recombinant origin of replication comprises the sequence of SEQ ID NO: 19 or the sequence complementary thereto.

In still another aspect, the recombinant origin of replication comprises the sequence of nucleotides 9629–10,315 of SEQ ID NO: 1 or the sequence complementary thereto.

Another embodiment of the present invention is a vector comprising a recombinant high copy number origin of replication having at least one cloning site introduced therein. The cloning site is positioned in the high copy number origin of replication such that the ability of the high copy number origin of replication to direct replication is not disrupted when no insert has been cloned into the at least one cloning site and is disrupted when an insert is cloned into the at least one cloning site.

Another embodiment of the present invention is a vector comprising a ColE1-derived origin of replication having at least one cloning site introduced therein. The cloning site is positioned in the high copy number origin of replication such that the ability of the high copy number origin of replication to direct replication is not disrupted when no insert has been cloned into the at least one cloning site and is disrupted when an insert is cloned into the at least one cloning site.

Another aspect of the present invention is a vector comprising the pUC19 origin of replication having at least one cloning site introduced therein. The cloning site is positioned in the high copy number origin of replication such that the ability of the high copy number origin of replication to direct replication is not disrupted when no insert has been cloned into the at least one cloning site and is disrupted when an insert is cloned into the at least one cloning site.

Another aspect of the present invention is a recombinant origin of replication having at least one cloning site introduced therein, the cloning site being positioned in the high copy number origin of replication such that the ability of the high copy number origin of replication to direct replication is not disrupted when no insert has been cloned into the at least one cloning site and is disrupted when an insert is cloned into the at least one cloning site, wherein the recombinant origin of replication comprises the sequence of SEQ ID NO: 18 or the sequence complementary thereto.

Another aspect of the present invention is a recombinant origin of replication having at least one cloning site introduced therein, the cloning site being positioned in the high copy number origin of replication such that the ability of the high copy number origin of replication to direct replication is not disrupted when no insert has been cloned into the at least one cloning site and is disrupted when an insert is cloned into the at least one cloning site, wherein the recombinant origin of replication comprises the sequence of SEQ ID NO: 19 or the sequence complementary thereto.

Another aspect of the present invention is a recombinant origin of replication having at least one cloning site introduced therein, the cloning site being positioned in the high copy number origin of replication such that the ability of the high copy number origin of replication to direct replication is not disrupted when no insert has been cloned into the at least one cloning site and is disrupted when an insert is cloned into the at least one cloning site, wherein the recombinant origin of replication comprises sequence of nucleotides 9629–10,315 of SEQ ID NO: 1 or the sequence complementary thereto.

Another embodiment of the present invention is a method of determining the copy number of a vector in a host cell comprising introducing a vector comprising a truncated lacZ gene into the host cell, the, the truncated lacZ gene conferring dark blue coloration on the host cells when the host cells are grown on medium containing Xgal and IPTG and the truncated lacZ gene is present at high copy number in the host cells, the truncated lacZ gene also conferring light blue coloration on the host cells when the host cells are grown on medium containing Xgal and IPTG and the truncated lacZ gene is present at low copy number in the host cells, and determining the color of the host cells when the host cells are grown on medium containing Xgal and IPTG.

Another embodiment of the present invention is a method of determining the copy number of a vector in a streptomycin resistant host cell. A vector comprising the strA+ gene is introduced into the streptomycin resistant host cell, wherein the host cells are unable to grow in the presence of streptomycin when the strA gene is present at high copy number and the host cells are able to grow in the presence of streptomycin when the strA gene is present at low copy number. The host cells containing the vector are grown on medium containing streptomycin.

Another embodiment of the present invention is a method of reducing the copy number of a vector in a host cell. A vector is obtained which comprises a first origin of replication capable of directing replication at a first copy number and a second origin of replication capable of directing replication at a second copy number, the first copy number being greater than the second copy number. The first origin of replication further comprises at least one cloning site therein which is positioned in the first origin of replication such that the ability of the first origin of replication to direct replication is not disrupted when no insert has been cloned into the cloning site and is disrupted when an insert is cloned into the cloning site. An insert is cloned into the at least one cloning site, thereby disrupting the activity of the first origin of replication and causing the vector to replicate at the second copy number in the host cell.

In one aspect, the method further comprises identifying cells having the vector present at the second copy number using a copy number indicator.

In another aspect, the step of identifying cells having the vector present at the second copy number comprises selecting cells having the vector present at the second copy number using a selectable marker.

In still another aspect, the step of selecting cells having the vector present at the second copy number comprises selecting streptomycin resistant cells using the strA+ gene.

In a further aspect, the step of identifying cells having the vector present at the second copy number comprises identifying light blue cells using a truncated form of the LacZ gene. In this aspect, cells containing the truncated lacZ gene at high copy number are dark blue when grown on medium containing Xgal and IPTG and cells containing the truncated LacZ gene at low copy number are light blue when grown on medium containing Xgal and IPTG.

Another aspect of the present invention is a method for identifying vectors containing a DNA insert, comprising the steps of subjecting a plurality of vectors to insertion conditions under which an insert is placed in at least some of the vectors, wherein the vectors have a first copy number if no insert occurs and a second copy number if the insert occurs, and identifying at least some vectors containing an insert by screening the vectors for the second copy number.

BRIEF DESCRIPTION OF THE DRAWINGS

FIGS. 3A–3C summarize the procedures for using Exonuclease III to generate deletions in the inserts and selecting cells containing vectors with Exonuclease III generated deletions in the inserts.

FIGS. 4A–4C summarize the procedures for using mung bean nuclease to generate deletions in the inserts and selecting cells containing vectors with mung bean nuclease generated deletions in the inserts.

FIGS. 5A and 5B compare different methods for obtaining the sequence of nested deletions.

DETAILED DESCRIPTION OF THE PREFERRED EMBODIMENT

Figure 1:
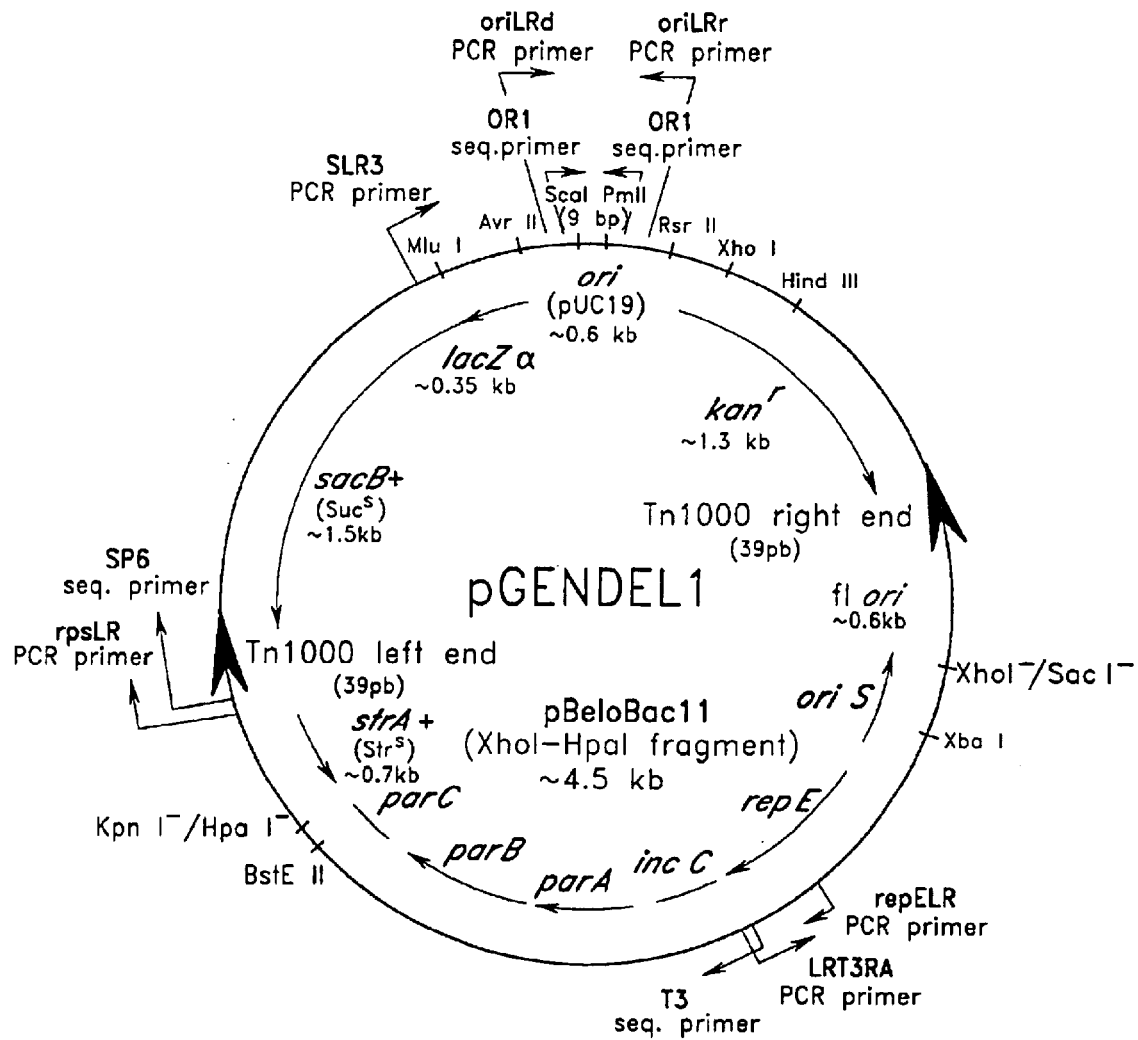
FIG. 1 is a map of pGenDel1.

The present invention relates to high throughput DNA sequencing vectors which facilitate the maintenance, sequencing and mapping of large regions of eucaryotic DNA using enzymatic and/or transposition based methods for generating nested deletions. The present high throughput DNA sequencing vectors are based on a new universal low copy number vector system. As described in more detail below, the present vectors contain a high copy number origin of replication having at least one cloning site therein. The high copy number origin of replication facilitates the isolation and manipulation of the vector DNA without an insert cloned therein. The present vectors also contain a low copy number origin of replication which is capable of maintaining the vectors at a few copies per cell or a single copy per cell. When an insert is cloned into the cloning sites in the high copy number origin of replication, the high copy number origin of replication is inactivated, and the low copy number origin of replication maintains the vector at a few copies per cell or at a single copy per cell. In addition to their applications in DNA sequencing, some embodiments of the present vectors may be used as Bacterial Artificial Chromosomes (BACs) to identify and stably maintain constructs into which inserts, such as genomic DNA inserts, have been cloned.

The present vectors may be designed to facilitate the generation of nested deletions using enzymatic methods, transposition based methods, or both. In addition to the origins of replication discussed above, the present vectors may have additional features, described below, which facilitate their use in generating or sequencing the desired nested deletions.

The plasmids pGenDel1, pGenBac1, and pGenBac2 will be referred to throughout this application as illustrative of the general features of the vectors of the present invention. pGenDel1 is a plasmid designed for generating nested deletions using both enzymatic procedures and transposition based methods. The sequence of pGenDel1 is provided in the appended sequence listing and is denoted as SEQ ID NO:1. A map of pGenDel1 illustrating the features discussed below is provided in FIG. 1.

pGenBac1 and pGenBac2 are vectors designed for maintaining DNA inserts at low copy numbers and are particularly useful for creating Bacterial Artificial Chromosome (BAC) libraries.

Those skilled in the art will appreciate that although pGenDel1, pGenBac1, and pGenBac2 will be referred to as illustrative vectors of the present invention, the present vectors are not limited to vectors having the exact sequence or structure of pGenDel1, pGenBac1 or pGenBac2.

Vectors for Maintaining Inserts at Low Copy Number

One aspect of the present invention is a vector for maintaining inserts at a low copy number or at a single copy per cell. Maintaining the inserts at low copy number after cloning increases their stability, permits the sequencing of eucaryotic sequences which are unclonable in multiple copies due to toxicity, instability, or other characteristics, and ensures that an accurate sequence will be obtained. These vectors contain a high copy number origin of replication having one or more cloning sites therein, a low copy number origin of replication and any controlling genes required for the activity of the low copy number origin of replication, and at least one copy number indicator. In addition, the vectors may have other features, such as a vector maintenance marker, hybridization sites for insert amplification primers, hybridization sites for insert sequencing primers, and a single stranded origin of replication.

Each of the vectors for maintaining inserts at low copy number has the features listed below. While pGenDel1 is used as a representative of this class of vectors, it will be appreciated that this class of vectors need not include all the features of pGenDel. Instead, this class of vectors comprises the features listed below.

In addition, pGenBac1 and pGenBac2 (described in more detail below) may also be used to maintain inserts at low copy number.

A. High Copy Number Origin of Replication

As discussed above, the vectors of the present invention contain a high copy number origin of replication having one or more cloning sites therein which do not disrupt the ability of the origin to direct high copy number replication. As used herein, the term "high copy number origin of replication" includes an origin of replication which directs replication at a copy number higher than that obtained under the direction of the low copy number origins of replication discussed below. In particular, the terminology "high copy number origin of replication" includes origins which direct replication at a copy number at least twice the copy number obtained under the direction of the low copy number origins of replication discussed below.

Preferably, the high copy number origin of replication maintains the vector at a copy number of from about 10 to about 700 copies per host cell. More preferably, the high copy number origin of replication maintains the vector at a copy number of from about 200 to about 700 copies per host cell. In a highly preferred embodiment, the high copy number origin of replication maintains the vector at a copy number of from about 500 to about 700 copies per host cell.

In the vectors of the present invention, the high copy number origin of replication has been modified to contain at least one restriction site therein without disrupting the ability of the origin to direct high copy number replication. Numerous high copy number origins of replication suitable for use in the vectors of the present invention are known to those skilled in the art. These include the ColE1-derived origin of replication from pBR322 and its derivatives as well as other high copy number origins of replication, such as M13 FR ori or p15A ori. Preferably, the high copy number origin of replication comprises the ColE1-derived pUC19 origin of replication.

The restriction site is positioned in the origin of replication such that cloning of an insert into the restriction site will inactivate the origin, rendering it incapable of directing replication of the vector. Alternatively, the at least one restriction site may be positioned within the origin such that cloning of an insert into the restriction site will render it capable of supporting only low or single copy number replication of the vector.

The following method may be used to construct high copy number origins of replication which possess at least one restriction site positioned in the origin of replication such that cloning of an insert into the restriction site will inactivate the origin, rendering it incapable of directing replication of the vector or positioned within the origin such that cloning of an insert into the restriction site will render it capable of supporting only low or single copy number replication of the vector. A high copy number origin of replication is mutagenized to introduce a restriction site in the origin using standard procedures such as oligonucleotide-directed mutagenesis, degenerate oligonucleotide mutagenesis, in vitro synthesis of mutant origins, linker-scanning mutagenesis, or directed mutagenesis using the polymerase chain reaction. These techniques are described in Ausebel et al., Current Protocols in Molecular Biology, John Wiley & Sons, 1997, the disclosure of which is incorporated herein by reference. In some methods, the mutagenized origins are inserted into or created in a vector which also contains a low copy number origin of replication which is capable of directing replication of the vector at a low copy number, any associated genes needed for the operation of the low copy number origin of replication, and at least one copy number indicator indicative of the copy number of the vector in a host cell.

The following procedure may be used to identify mutations which are positioned within the high copy number origin of replication such that cloning of an insert into the restriction site will inactivate the origin, rendering it incapable of directing replication of the vector or mutations which are positioned within the high copy number origin of replication such that cloning of an insert into the restriction site will render it capable of supporting only low or single copy number replication of the vector.

Mutations within the high copy number origin of replication which do not disrupt the ability of the origin to direct high copy number replication are identified as follows. The mutagenized origins are introduced into suitable host cells. The copy number of vectors containing mutagenized origins is compared to that of vectors containing unaltered origins by performing Southern blots, by determining the yield of plasmid DNA extracted from cells containing plasmids with different origins of replication, or by using copy number indicators such as the truncated lacZ gene or strA+ gene described below. Mutations which permit the vector to replicate at approximately the same copy number as the unaltered origin are then screened as described below.

Inserts are cloned into the restriction site and the copy number of vectors containing the inserts is determined by performing Southern blots, by determining the yield of plasmid DNA extracted from cells containing plasmids with different origins of replication, or by using copy number indicators such as the truncated lacZ gene or strA+ gene described below. Those mutations which permit replication at high copy number without an insert and low copy number with an insert cloned into the restriction site in the origin may be utilized as described below.

Preferably, the high copy number origin of replication in which at least one restriction site is constructed comprises the pUC19 origin of replication between bases 1889 through 2576 of pUC19 (GenBank Accession No. M77789, the disclosure of which is incorporated herein by reference). Preferably, the restriction site is constructed between bases 2295 and 2301 of pUC19.

As shown in FIG. 1 and the sequence of SEQ ID NO:1, bases 9629 through 10315 of pGenDel1 contain a fragment derived from bases 1889 through 2576 of pUC19 (GenBank Accession No. M77789), which includes the high copy number pUC 19 origin of replication.

In some embodiments, more than one restriction site may be positioned in the origin at locations wherein the function of the origin is not disrupted or reduced unless an insert is cloned into one or more of the restriction sites. For example, as shown in FIG. 1 and the sequence of SEQ ID NO:1, in pGenDel1 the pUC 19 origin of replication was engineered to include the sequence TACTCTACA (SEQ ID NO:2) at bases 10031 through 10039 of pGenDel1 (corresponding to bases 2291 through 2301 of pUC 19), thereby creating unique ScaI and PmlI sites in pGenDel1. The insertion of the ScaI and PmlI sites at these positions does not disrupt the ability of the origin to direct high copy number replication.

Alternatively, the pUC 19 origin of replication may be modified to create BamHI (SEQ ID NO: 19) or EcoRI (SEQ ID NO: 18) sites in the origin. The introduction of the BamHI or EcoRI sites does not disrupt the ability of the origin to direct replication.

The high copy number origin of replication enables large amounts of the present vectors to be isolated using standard DNA preparation techniques such as large scale alkaline lysis procedures. DNA to be sequenced or mapped may be cloned into the isolated vector DNA using standard cloning procedures such as those described in Ausebel et al., Current Protocols in Molecular Biology, John Wiley & Sons, 1997, the disclosure of which is incorporated herein by reference.

B. Low Copy Number Origin of Replication

The vectors of the present invention also contain a low copy number origin of replication and its controlling genes which are capable of directing the replication of the vector at a low copy number or at a single copy per cell. Preferably, the low copy number origin of replication is capable of directing replication at a copy number of about 1 per cell. However, in some embodiments, the low copy number origin of replication may direct replication at more than one copy number per cell. For example, the low copy number origin of replication may direct replication at a copy number of less than 10 copies per cell.

As shown in FIG. 1 and SEQ ID NO:1, bases 1896 through 6544 of pGenDel1 contain an HpaI-XhoI fragment derived from bases 2382 through 6997 of pBeloBAC11 (GenBank accession number U51113, the disclosure of which is incorporated herein by reference). This HpaI-XhoI fragment contains the oriS low copy number origin of replication, as well as the repE, incC, parA, par B and parC genes which control replication from the origin and partitioning of the replicated plasmids in daughter cells. The HpaI-XhoI fragment from pBeloBAC11 was modified by insertion of an oligonucleotide having the sequence TGGG-GATTAACCCTCACTAAAGGGACGGCTTT (SEQ ID NO:3) at the position corresponding to base 3522 of pBeloBAC11. This modification allows the use of LRT3RA and T3 primers for PCR amplification and sequencing, as described below.

When the high copy number origin of replication is disrupted by the cloning of an insert into a restriction site therein, the low copy number origin of replication permits replication of the vector at a low copy number or at a level of one vector molecule per host cell. As discussed in more detail below, the low copy number of vectors having inserts cloned therein increases the stability of the insert DNA and reduces the number of steps required to obtain the sequence of the insert DNA. In addition, the low copy number of vectors containing an insert therein allows a greater degree of confidence that the insert sequence has not been altered during replication of the vector.

C. Copy Number Indicator

The vectors of the present invention also include at least one marker indicative of the copy number of the vector in the host cell in which it resides. This feature is used to identify vectors in which an insert has inactivated the high copy number origin of replication, thereby causing the vector to be present at a low copy number or in a single copy. The copy number indicator may be a color based indicator or, alternatively, may be a selectable marker which is sensitive to the copy number of the vector. When the copy number indicator is a selectable marker, it not only allows copy number estimation but also permits copy number dependent selection to facilitate the identification and recovery of vectors containing inserts therein.

In some embodiments, the vector may contain more than one copy number indicator. For example, as shown in FIG. 1 and SEQ ID NO:1, pGenDel1 contains two copy number indicators. One of the copy number indicators is the rpsL gene (GenBank Accession number J01688, the disclosure of which is incorporated herein by reference), which is also referred to as the stra+ gene. In pGenDel1, the strA+ gene is located between base 6574 and base 7218 of SEQ ID NO:1, between the HpaI end of the pBeloBAC11 fragment and the left end of Tn1000. However, those skilled in the art will appreciate that the copy number indicator is not limited to this location and may be located at any position in the vector consistent with its intended purpose. Similarly, it will be appreciated that the copy number indicator may be any copy number indicator consistent with its intended purpose, and that the copy number indicator is not limited to those specifically listed herein.

The strA+ gene in pGenDel1 has been modified to change the base corresponding to position 342 of the strA+ gene of GenBank Accession number J01688 (position 7058 in pGenDel1) from A to T. This modification does not affect the amino acid sequence of the translated protein but removes a PmlI site in order to maintain the PmlI site in the high copy number origin of replication as a unique site. The present vectors utilize the new observation that when the strA+ gene is present in high copy number, it confers streptomycin sensitivity on cells which are normally streptomycin resistant. Thus, prior to cloning of an insert into the high copy number origin of replication, host cells which are normally resistant to streptomycin will be sensitive to streptomycin as a consequence of the high copy number of the strA+ gene. When an insert is cloned into the high copy number origin of replication thereby reducing the copy number of the vector, the cells will become resistant to streptomycin. Thus, streptomycin resistance may be used to positively select cells containing vectors with inserts in the high copy number origin of replication.

In addition to the strA+ gene, pGenDel1 contains a second marker indicative of the copy number of the vector in the host cell. This second marker is a truncated version of the LacZ gene which was obtained as follows. The double stranded synthetic linker HE1 having the sequence AGC-TACGGGAAAGCC (SEQ ID NO:4)/ HE2:AATTGGCTTTCCCGT (SEQ ID NO: 20) was ligated to pUC19 DNA which had been digested with HindIII and EcoRI, thereby eliminating the HindIII and EcoRI sites in pUC19. When transformed into bacterial host cells, the modified pUC19 plasmid gives blue colonies on X-Gal/IPTG containing media. As is discussed in greater detail below, the truncated LacZ gene permits discrimination between vectors containing inserts, vectors containing point mutations in the strA gene, and vectors lacking an insert.

The modified pUC19 plasmid was subjected to PCR amplification with the primers:

lacLRS2Avr: AGTCCTAGGTGAGCGCAACGCAAT-TAATG (SEQ ID NO:5) and lacE2Mlu having the sequence AACACGCGTAGGCGC-CATTCGCCATT (SEQ ID NO:6), in order to generate a truncated 379 bp version of the lacZ α peptide gene containing bases 1–326 of the LacZ gene having the sequence of SEQ ID NO:7. The resulting fragment was inserted into pGenDel1 at bases 9298 through 9623 such that it is positioned near the high copy number origin of replication. However, those skilled in the art will appreciate that the second copy number indicator is not limited to this location and may be located at any position in the vector consistent with its intended purpose. Similarly, it will be appreciated that the second copy number indicator may be any copy number indicator consistent with its intended purpose and is not limited to the truncated lacZ α peptide of SEQ ID NO:7.

The truncated LacZ gene causes colonies containing the vector in high copy number to appear dark blue when grown in the presence of Xgal and IPTG. In contrast, colonies containing the vector at low copy number or in a single copy appear light blue when grown in the presence of Xgal and IPTG. The light blue colonies containing the vector at low copy number or in a single copy are easily distinguishable from colonies containing the vector at high copy number.

Although the truncated lacZ derivative in pGenDel1 contains bases 1–326 of the lacZ gene, other truncated derivatives may be prepared which are also capable of indicating the copy number of the vector. Preferably, the truncated lacZ gene contains bases 1 through 392 of the lacZ gene. The truncated lacZ gene may also contain bases 1 through 292 of the lacZ gene. It will be appreciated that other truncated lacZ derivatives may be designed which are consistent with the uses described herein, and such derivatives are within the scope of the present invention.

In those embodiments of the present vectors used for transposition based methods and/or enzymatic methods of generating nested deletions, the truncated lacZ gene may also be used as a deletion indicator which allows identification or selection of cells in which transposition has generated a deletion within the insert in the high copy number origin of replication. The use of the truncated lacz gene for this purpose is described below.

D. Vector Maintenance Marker

The vectors of the present invention also include a marker for selecting host cells which contain the vector. This selectable marker may be any of a variety of selectable markers known to those skilled in the art. In particular, the selectable marker may confer resistance to a drug, biomolecule, metabolite, or other agent.

In pGenDel1, the marker for selecting host cells harboring the vector is the kan$^r$ gene derived from bases 720 through 1535 of the plasmid pUC4K (GenBank Accession No. X06404, the disclosure of which is incorporated herein by reference) available from Pharmacia. The kan$^r$ gene is located between bases 9 and 1266 of pGenDel1. However, those skilled in the art will appreciate that the marker for selecting host cells harboring the vector is not limited to this location or this particular marker. Instead, the marker for selecting host cells harboring the vector may be any marker consistent with its intended purpose and may be located at any position in the vector consistent with its intended purpose.

In the pGenBac vectors, the vector maintenance marker is the chloramphenicol acetyl transferase gene, which confers resistance to chloramphenicol. Those skilled in the art will appreciate that a number of other plasmid maintenance markers may also be used. The present invention contemplates the use of any plasmid maintenance marker consistent with the purposes described herein.

E. Insert Amplification Primers

In a preferred embodiment, hybridization sites for insert amplification primers are located on each side of the cloning sites in the high copy number origin of replication. The insert amplification primers may have any sequence complementary to a sequence near the cloning sites in the high copy number origin of replication. Preferably, the insert amplification primers are at least 15 nucleotides in length. More preferably, the insert amplification primers are between 15 and 25 nucleotides in length.

The hybridization sites for insert amplification primers may be from about 20 to about 800 bases from the cloning sites in the high copy number origin of replication. Preferably, the hybridization sites for insert amplification primers are from about 20 to about 200 bases from the cloning sites in the high copy number origin of replication. More preferably, the hybridization sites for insert amplification primers are from about 20 to about 80 bases from the cloning sites in the high copy number origin of replication.

As shown in FIG. 1 and SEQ ID NO:1, the left hybridization site for an insert amplification primer is located between base 9856 and base 9881 of pGenDel1 and is complementary to the insert amplification primer designated oriLRd. OriLRd has the sequence CTACATAC-CTCGCTCTGCTAATCCTG (SEQ ID NO:8). However, those skilled in the art will appreciate that the left hybridization site for the insert amplification primer is not limited to this particular sequence or this particular location and that it may be any sequence or located at any position in the vector consistent with its intended purpose.

As shown in FIG. 1, the right hybridization site for an insert amplification primer is located between base 10182 and base 10202 of pGenDel1 and is complementary to the sequencing primer designated oriLRr. OriLRr has the sequence GACGCTCAAGTCAGAGGTGGC (SEQ ID NO:9). However, those skilled in the art will appreciate that the right hybridization site for an insert amplification primer is not limited to this particular sequence or this particular location and that it may be any sequence or located at any position in the vector consistent with its intended purpose.

The insert amplification primers are used to amplify the insert which has been cloned into the high copy number origin of replication. After amplification of the insert by PCR or other amplification techniques, the insert may be sequenced using insert sequencing primers as described below.

F. Insert Sequencing Primers

In a preferred embodiment, hybridization sites for insert sequencing primers are located on each side of the cloning sites in the high copy number origin of replication. The insert sequencing primers may have any sequence complementary to a sequence near the cloning sites in the high copy number origin of replication. Preferably, the insert sequencing primers are at least 15 nucleotides in length. More preferably, the insert sequencing primers are between 15 and 25 nucleotides in length.

The hybridization sites for insert sequencing primers may be from about 1 to about 200 bases from the cloning sites in the high copy number origin of replication. Preferably, the hybridization sites for insert sequencing primers are from about 1 to about 100 bases from the cloning sites in the high copy number origin of replication. More preferably, the hybridization sites for insert sequencing primers are from about 1 to about 50 bases from the cloning sites in the high copy number origin of replication.

Preferably, the hybridization sites for insert sequencing primers are between the hybridization sites for insert amplification primers.

As shown in FIG. 1 and SEQ ID NO:1, the left hybridization site for an insert sequencing primer is located between base 10009 and base 10026 of pGenDel1 and is complementary to the sequencing primer designated OS1. OS1 has the sequence GAACGACCTACACCGAAC (SEQ ID NO:10). However, those skilled in the art will appreciate that the left hybridization site for an insert sequencing primer is not limited to this sequence or this location and that it may be any sequence or located at any position in the vector consistent with its intended purpose.

As shown in FIG. 1 and SEQ ID NO:1, the right hybridization site for an insert sequencing primer is located between base 10046 and base 10062 of pGenDel1 and is complementary to the sequencing primer designated OR1. OR1 has the sequence GTGGCGCTTTCTCATAG (SEQ ID NO:11). However, those skilled in the art will appreciate that the right hybridization site for an insert sequencing primer is not limited to this sequence or this location and that it may be any sequence or located at any position in the vector consistent with its intended purpose.

The insert sequencing primers are used to determine the sequences of the inserts or the sequences of the ends of inserts which have been cloned into the cloning sites in the high copy number origin of replication using standard DNA sequencing techniques. In such procedures, the insert may be amplified using the insert amplification primers. The insert sequencing primers are hybridized to the complementary sequences (the insert sequence hybridization sites) in the amplification product and extended in the presence of detectable dideoxy nucleotides using standard DNA sequencing techniques. The products of the sequencing reaction are then electrophoretically separated and the sequences of the inserts or the ends of the inserts are read using an automated sequencer such as the ABI Prism 377 sequencers (Perkin Elmer, Applied Biosystems Division, Foster City, Calif.).

Alternatively, the insert sequencing primers may be used to sequence the inserts or the ends of the inserts in the vectors directly without PCR amplification using standard plasmid sequencing procedures.

G. Single Stranded Origin of Replication

The high throughput DNA sequencing vectors of the present invention may optionally contain an origin of replication derived from a single stranded bacteriophage. For example, pGenDel1 contains a 600 bp fragment derived from bases 3 through 475 of PCR-ScriptAmpSK+ (GenBank accession number U46017, the disclosure of which is incorporated herein by reference). This fragment, which lies between bases 1423 and 1894 of pGenDel1, contains the origin of replication of bacteriophage f1. The f1 origin of replication permits the isolation of single stranded DNA templates for use in sequencing procedures by superinfection with f1 or M13 bacteriophages in bacterial strains having f pili.

As shown in FIG. 1 and SEQ ID NO:1, the f1 origin of replication in pGenDel1 is located near the XhoI site of the pBeloBac11 derived fragment. However, those skilled in the art will appreciate that the f1 origin is not limited to this location and may be located at any position in the vector consistent with its intended purpose.

Vectors Designed for Generating Nested Deletions Using Transposition Based Methods The features of high throughput sequencing vectors which are transposition based deletion vectors are described below. Each of the vectors for generating nested deletions using transposition based methods has the features listed below. While pGenDel1 is used as a representative of this class of vectors, it will be appreciated that this class of vectors need not include all the features of pGenDel. Instead, this class of vectors comprises the features listed below.

The vectors for generating nested deletions using transposition based methods contain a high copy number origin of replication having cloning sites therein, a low copy number origin of replication and any controlling genes required for the activity of the low copy number origin of replication, and at least one copy number indicator as described above. In addition, the transposition based deletion vectors have transposition elements and at least one deletion indicator. The transposition based deletion vectors may also have the other features described above, such as a vector maintenance marker, hybridization sites for insert amplification primers, hybridization sites for insert sequencing primers, and single stranded origin of replication. Furthermore, the transposition based deletion vectors may also have hybridization sites for transposition deletion amplification primers and hybridization sites for transposition deletion sequencing primers.

A. Transposition Elements

The vectors of the present invention which are designed for facilitating the generation of nested deletions using transposition based techniques include transposition elements therein. Preferably, the transposition elements comprise the minimal sequences capable of undergoing transposition in the presence of transposase. Preferably, the transposase is expressed from a source other than the sequencing vector, such as a separate plasmid encoding transposase.

The transposition elements may be derived from any of the transposons known to those skilled in the art, such as Tn9 or Tn1000. Preferably, the transposition elements are derived from a transposon which exhibits little sequence specificity for transposition sites, such as Tn1000.

As shown in FIG. 1 and the sequence of SEQ ID NO:1, pGenDel1 contains the rightmost and the inverted leftmost 39 bp of Tn1000. As shown in FIG. 1, the leftmost 39 bp of Tn1000 are on one side of the high copy number origin while the inverted rightmost 39 bp of Tn1000 are on the other side of the high copy number origin.

As illustrated in FIG. 1, the ends of Tn1000 in pGenDel1 are located near the f1 origin and strA+ gene (discussed below). However, those skilled in the art will appreciate that the transposition elements are not limited to these locations and may be located at any positions in the vector consistent with their intended purpose. It will also be appreciated that any transposition elements consistent with the intended purpose may be used.

B. Deletion Indicator

The high throughput DNA sequencing vectors of the present invention which are designed for facilitating the generation of nested deletions using transposition based techniques include at least one deletion indicator which allows identification or selection of cells in which transposition has generated a deletion within the insert in the high copy number origin of replication. The indicator may be any of a variety of markers known to those skilled in the art. Preferably, the deletion indicator allows the selection of cells containing vectors in which a transposition event has generated a deletion to facilitate the identification and recovery of vectors containing deletions in the genomic DNA insert. However, the deletion indicator may also be any other type of marker for which a loss of activity is readily detectable.

The deletion indicator lies between the transposition elements and is located near the cloning sites in the high copy number origin of replication, such that it is likely that a transposition based deletion which deletes the deletion indicator will extend into the insert which has been cloned into the high copy number origin of replication. The deletion indicator may be from about 200 to about 10,000 bases from the cloning sites in the high copy number origin of replication. Preferably, the deletion indicator is from about 200 to about 1000 bases from the cloning sites in the high copy number origin of replication. More preferably, the deletion indicator is from about 200 to about 400 bases from the cloning sites in the high copy number origin of replication. However, it will be appreciated that the deletion indicator may also be placed at any other location in the vector consistent with its intended purpose, and such other locations are within the scope of the present invention.

As shown in FIG. 1 and the sequence of SEQ ID NO:1, pGenDel1 contains the selectable marker sacB between bases 7305 and 9227 such that the sacB gene is positioned between the transposition elements. The SacB gene encodes levan-sucrase, a protein which renders the host cells sensitive to sucrose. Thus, cells containing vectors in which a transposition based deletion has removed the SacB gene are sucrose resistant, while cells in which no deletion has occurred are sucrose sensitive. Accordingly, sucrose containing medium may be used to select cells bearing a transposition based deletion.

The high throughput DNA sequencing vectors of the present invention which are designed for facilitating the generation of nested deletions using transposition based techniques may also include a second deletion indicator to identify cells having vectors in which the deletion resulting from a transposition event extends into the insert which was cloned into the high copy number origin of replication.

Preferably, the second deletion indicator is relatively short in length to minimize the recovery of transposition based deletions which delete the deletion indicator but do not extend into the insert which has been cloned into the high copy number origin of replication. For example, the deletion indicator may be from about 100 to about 2000 bases in length. Preferably, the deletion indicator is from about 100 to about 800 bases in length. More preferably, the deletion indicator is from about 100 to about 300 bases in length.

Preferably, the second deletion indicator is located near the end of the insert in which the desired deletions will occur. For example, the second deletion indicator may be from about 1 to about 2000 bases from the end of the insert in which the desired deletions will occur. Preferably, the second deletion indicator is from about 1 to about 300 bases from the end of the insert in which the desired deletions will occur. However, it will be appreciated that the second deletion indicator may be placed at other locations consistent with its intended purpose, and such other locations are within the scope of the present invention.

In pGenDel1, the second deletion indicator is the truncated lacZ gene located between base 9298 and base 9623 in the sequence of SEQ ID NO:1. However, those skilled in the art will appreciate that the deletion indicator is not limited to this location and may be located at any position in the vector consistent with its intended purpose. Transposition based deletions which extend from the left end of Tn1000 into the insert which has been cloned into the high copy number origin of replication will delete the truncated lacZ gene, thereby causing the colonies containing such deletions to be white when grown on Xgal and IPTG.

In addition, the truncated lacZ gene permits the recovery of cells carrying vectors in which a non-transposition based mutation has inactivated the SacB gene to be eliminated. Cells containing a vector in which a transposition based deletion has deleted both the sacB gene and the truncated lacZ gene will be sucrose resistant and white on medium containing Xgal and IPTG. In contrast, cells in which a non-transposition based mutation has inactivated the SacB gene will be sucrose resistant and light blue on Xgal and IPTG.

The vectors of the present invention may also contain markers which facilitate counterselection of vectors which contain deletions which have proceeded too far, thereby resulting in a complete deletion of the insert. For example, in pGenDel1, transposition-mediated deletion (described in more detail below) of the kan$^r$ gene renders host cells containing a vector with a fully deleted insert unable to grow on kanamycin.

C. Hybridization Sites for Deletion Amplification Primers

In some embodiments, it may be desirable to obtain the sequence of nested deletions resulting from transposition events by amplifying the inserts resulting from the transposition and sequencing the amplification product.

In those embodiments of the present vector designed for generating nested deletions using transposition based methods, the vectors preferably contain hybridization sites for primers for amplifying inserts in vectors containing deletions generated by transposition. Preferably, the deletion amplification primers are at least 15 nucleotides in length. More preferably, the deletion amplification primers are between 15 and 25 nucleotides in length.

The hybridization site for the first deletion amplification primer is located near the cloning sites in the high copy number origin of replication on the opposite end of the insert from the end where the desired deletions occur such that the hybridization site for the first deletion amplification primer remains present in the vector following a deletion that partially deletes the insert. The hybridization site for the first deletion amplification primer may be from about 15 to about 300 bases from a cloning site in the high copy number origin of replication. Preferably, the hybridization site for the first deletion amplification primer is from about 15 to about 150 bases from the cloning site in the high copy number origin of replication. More preferably, the hybridization site for the first deletion amplification primer is from about 15 to about 60 bases from the cloning site in the high copy number origin of replication. However, it will be appreciated that the hybridization site for the first deletion amplification primer may be placed at other locations consistent with its intended purpose, and such other locations are within the scope of the present invention.

The hybridization site for the second deletion amplification primer is located near the transposition element which produces the desired nested deletions such that it remains present in the vector following a transposition event which generates a deletion in the insert. The hybridization site for the second deletion amplification primer may be from about 15 to about 2000 bases from the transposition element which produces the desired nested deletions. Preferably, the hybridization site for the second deletion amplification primer is from about 15 to about 1000 bases from the transposition element which produces the desired nested deletions. More preferably, the hybridization site for the second deletion amplification primer is from about 15 to about 600 bases from the transposition element which produces the desired nested deletions. However, it will be appreciated that the hybridization site for the second deletion amplification primer may be placed at other locations consistent with its intended purpose, and such other locations are within the scope of the present invention.

As shown in FIG. 1 and SEQ ID NO:1, the hybridization site for the first deletion amplification primer is located between base 10182 and base 10202 of pGenDel1 and is complementary to the sequencing primer designated OriLRr, which was discussed above. However, those skilled in the art will appreciate that the hybridization site for the first deletion amplification primer is not limited to this location and may be located at any position in the vector consistent with its intended purpose.

As shown in FIG. 1 and SEQ ID NO:1, the hybridization site for the second deletion amplification primer is located between base 7155 and base 7174 of pGenDel1 and is complementary to the sequencing primer designated rpsLR. RpsLR has the sequence AGGACGCCGAATTTTAGGGC (SEQ ID NO:12). However, those skilled in the art will appreciate that the hybridization site for the second deletion amplification primer is not limited to this location and may be located at any position in the vector consistent with its intended purpose.

As discussed further below, the deletion amplification primers are used to amplify inserts having deletions created by transposition. After amplification of the insert by PCR or other amplification techniques, the insert may be sequenced using sequencing primers for transposition based deletions as described below.

D. Sequencing Primers for Transposition Based Deletions

In a preferred embodiment, the vector contains hybridization sites for sequencing primers for transposition based deletions. The hybridization sites for sequencing primers for transposition based deletions are located near the transposition element which generates the desired deletions and are preferably positioned such that they will be contained in the amplification product generated using the amplification primers for transposition based deletions. Preferably, the sequencing primers for transposition based deletions are at least 15 nucleotides in length. More preferably, the sequencing primers for transposition based deletions are between 15 and 25 nucleotides in length.

The hybridization sites for sequencing primers for transposition based deletions may be from about 15 to about 300 bases from the transposition element which generates the desired deletions. Preferably, the hybridization sites for sequencing primers for transposition based deletions are from about 15 to about 150 bases from the transposition element which generates the desired deletions. More preferably, the hybridization sites for sequencing primers for transposition based deletions are from about 15 to about 60 bases from the transposition element which generates the desired deletions.

As shown in FIG. 1, the hybridization sites for sequencing primers for transposition based deletions are located between base 7230 and base 7248 (SP6 Sequencing Primer) or between base 7155 and base 7174 (rpsLR Sequencing Primer) of pGenDel1. The hybridization site for the SP6 primer is complementary to the sequence GATTTAGGT-GACACTATAG (SEQ ID NO:13). The hybridization site for the rpsLR primer is complementary to the sequence AGGACGCCGAATTTTAGGGC (SEQ ID NO:12). However, those skilled in the art will appreciate that the hybridization sites for sequencing primers for transposition based deletions are not limited to these locations or sequences and may be any sequence or located at any position in the vector consistent with their intended purpose.

The sequencing primers for transposition based deletions are used to determine the sequence of inserts having deletions generated by transposition. In such procedures, the insert is amplified using the amplification primers for transposition based deletions. The sequencing primers for transposition based deletions are hybridized to the complementary sequences in the amplification product and extended in the presence of detectable dideoxy nucleotides using standard DNA sequencing techniques. The products of the sequencing reaction are then electrophoretically separated and the sequence of the inserts is read using an automated sequencer such as the ABI Prism 377 sequencers (Perkin Elmer, Applied Biosystems Division, Foster City, Calif.).

The use of the above features for generating and sequencing nested deletions is described below.

Vectors Designed for Generating Nested Deletions Using Enzymatic Methods

The features of high throughput sequencing vectors which are enzymatic deletion vectors are described below. Each of the vectors for generating nested deletions using enzymatic methods has the features listed below. While pGenDel1 is used as a representative of this class of vectors, it will be appreciated that this class of vectors need not include all the features of pGenDel. Instead, this class of vectors comprises the features listed below.

The vectors for generating nested deletions using enzymatic methods contain a high copy number origin of replication having cloning sites therein, a low copy number origin of replication and any controlling genes required for the activity of the low copy number origin of replication, a deletion indicator and at least one copy number indicator as described above. The enzymatic deletion vectors may also have hybridization sites for primers for creating substrates for enzymatic deletions, hybridization sites for primers for amplifying deletions, and hybridization sites for primers for sequencing deletions. In addition, deletion vectors may also have the other features described above, such as a vector maintenance marker, hybridization sites for insert amplification primers, hybridization sites for insert sequencing primers, and a single stranded origin of replication.

A. Deletion Indicator

Preferably, the vectors designed for use in enzymatic methods for generating nested deletions have at least one deletion indicator for indicating when an enzymatic deletion has progressed into the insert in the high copy number origin of replication. The deletion indicator is preferably a marker for which the loss thereof through enzymatic deletion is readily detectable. The marker may be a selectable marker or a readily assayable protein, such as a calorimetrically detectable protein such as beta galactosidase. The deletion indicator is preferably of short length to minimize the recovery of deletions which have deleted enough of the deletion indicator to destroy the activity of the deletion indicator but have not progressed into the insert in the high copy number origin of replication. In those embodiments which are designed for generating nested deletions using both enzymatic and transposition-based methods, the deletion indicator for determining whether an enzymatic deletion has proceeded into the insert may also act as a deletion indicator for determining whether a deletion has been generated in the insert through a transposition event.

Preferably, the deletion indicator is located near the insert to maximize the probability that a deletion which removes the deletion indicator has progressed into the insert in the high copy number origin of replication. The deletion indicator may be from about 200 to about 10000 bases from the cloning sites in the high copy number origin of replication.

Preferably, the deletion indicator is from about 200 to about 1000 bases from the cloning sites in the high copy number origin of replication. More preferably, the deletion indicator is from about 200 to about 400 bases from the cloning sites in the high copy number origin of replication. However, it will be appreciated that the deletion indicator may be located at other positions consistent with its intended purpose, and such other positions are within the scope of the present invention.

The vectors of the present invention may also contain markers which facilitate counterselection of vectors which contain deletions which have proceeded from the undesired direction or vectors in which the entire insert has been deleted. For example, in pGenDel1, enzymatic deletion (described in more detail below) of the repE gene prevents the plasmid from replicating, thereby counterselecting cells containing vectors in which a deletion has proceeded from an undesired direction. Similarly, in pGenDel1, the kan$^r$ gene permits counterselection of cells containing vectors in which the entire insert has been deleted.

B. Amplification Primers for Generating Enzymatic Deletions

The enzymatic deletion vectors preferably contain hybridization sites for primers for generating a substrate for enzymatic deletions by amplifying a portion of the vector containing the low copy number origin of replication, the vector maintenance marker, the insert and the deletion indicator. The insert in the resulting amplified fragment is enzymatically deleted and colonies containing the desired nested deletions in the insert are identified.

The hybridization sites for amplification primers for generating enzymatic deletions are located on each side of the cloning sites in the high copy number origin of replication. Preferably, the amplification primers for generating enzymatic deletions are at least 15 nucleotides in length. More preferably, the amplification primers for generating enzymatic deletions are between 15 and 25 nucleotides in length.

The hybridization site for the first amplification primer for generating enzymatic deletions is located near the cloning sites in the high copy number origin of replication and provides the end of the fragment from which the desired deletions in the insert are generated. The hybridization site for the first amplification primer for generating enzymatic deletions may be from about 15 to about 3000 bases from a cloning site in the high copy number origin of replication. Preferably, the hybridization site for the first amplification primer for generating enzymatic deletions is from about 15 to about 2500 bases from the cloning site in the high copy number origin of replication. More preferably, the hybridization site for the first amplification primer for generating enzymatic deletions is from about 15 to about 400 bases from the cloning site in the high copy number origin of replication.

The hybridization site for the second amplification primer for generating enzymatic deletions is located further from the cloning sites in the high copy number origin of replication than the hybridization site for the first amplification primer for generating enzymatic deletions. Preferably, the hybridization site for the second amplification primer for generating enzymatic deletions is positioned such that the amplification product contains the low copy number origin of replication (and, where applicable, any genes necessary for the activity of the low copy number origin of replication), the vector maintenance marker, the insert, and the deletion indicator. As discussed below, in some embodiments the hybridization site for the second amplification primer for generating enzymatic deletions is designed to generate an end which is resistant to digestion by Exonuclease III. The hybridization site for the second amplification primer for generating enzymatic deletions may be from about 15 to about 5000 bases from a cloning site in the high copy number origin of replication. Preferably, the hybridization site for the second amplification primer for generating enzymatic deletions is from about 15 to about 3000 bases from the cloning site in the high copy number origin of replication. More preferably, the hybridization site for the second amplification primer for generating enzymatic deletions is from about 15 to about 2000 bases from the cloning site in the high copy number origin of replication.

As shown in FIG. 1 and SEQ ID NO:1, in pGenDel1 the hybridization site for the first amplification primer for generating enzymatic deletions is located between base 8711 and base 8731 and is complementary to the sequencing primer designated SLR3. SLR3 has the sequence TTTCGCGAAGGCTTGAGTCG (SEQ ID NO:14). However, those skilled in the art will appreciate that the hybridization site for the first amplification primer for generating enzymatic deletions is not limited to this location and may be located at any position in the vector consistent with its intended purpose.

As shown in FIG. 1 and SEQ ID NO:1, the hybridization site for the second amplification primer for generating enzymatic deletions is located between base 3045 and base 3069 of pGenDel1 and is complementary to the sequencing primer designated LRT3RA. LRT3RA has the sequence AAAGCCGTCCCTTTAGTGAGGGTTA (SEQ ID NO:15). However, those skilled in the art will appreciate that the hybridization site for the second amplification primer for generating enzymatic deletions is not limited to this sequence or this location and may be any sequence or located at any position in the vector consistent with its intended purpose.

As will be described in more detail below, the second amplification primer for generating enzymatic deletions may be designed to generate an end which is resistant to Exonuclease III digestion.

C. Amplification Primer for Generating Sequencing Templates from Enzymatic Deletions In preferred embodiments of the vectors designed for generating nested deletions using enzymatic methods, the vectors preferably contain hybridization sites for primers for generating sequencing templates from enzymatic deletions. Preferably, the hybridization sites for amplification primers for generating sequencing templates from enzymatic deletions are positioned such that they are included within the amplification product produced by the amplification primers for generating enzymatic deletions.

The hybridization site for the first amplification primer for generating sequencing templates from enzymatic deletions is preferably located near the hybridization site for the second amplification primer for generating enzymatic deletions and is on the opposite strand of the hybridization site for the second amplification primer for generating enzymatic deletions. The hybridization site for the first amplification primer for generating sequencing templates from enzymatic deletions may be located from about 15 bases to about 300 bases from the hybridization site for the second amplification primer for generating enzymatic deletions. Preferably, the hybridization site for the first amplification primer for generating sequencing templates from enzymatic deletions is located from about 15 bases to about 150 bases from the hybridization site for the second amplification primer for generating enzymatic deletions. More preferably, the hybridization site for the first amplification primer for generating sequencing templates from enzymatic deletions is located from about 15 bases to about 60 bases from the hybridization site for the second amplification primer for generating enzymatic deletions.

The hybridization site for the second amplification primer for generating sequencing templates from enzymatic deletions is preferably located near the undeleted end of the inserts having deletions produced using enzymatic techniques. The hybridization site for the second amplification primer for generating sequencing templates from enzymatic deletions may be located from about 15 bases to about 2000 bases from the undeleted end of the inserts having deletions produced using enzymatic techniques. Preferably, the hybridization site for the second amplification primer for generating sequencing templates from enzymatic deletions is located from about 15 bases to about 1000 bases from the undeleted end of the inserts having deletions produced using enzymatic techniques. More preferably, the hybridization site for the second amplification primer for generating sequencing templates from enzymatic deletions is located from about 15 bases to about 60 bases from the undeleted end of the inserts having deletions produced using enzymatic techniques.

As shown in FIG. 1 and SEQ ID NO:1, in pGenDel1, the hybridization site for the first amplification primer for generating sequencing templates from enzymatic deletions is between bases 2897 and 2918 and is complementary to the primer designated repELR. RepELR has the sequence CGCTTCCTGCAGGTCTGTGTTA (SEQ ID NO:16). However, those skilled in the art will appreciate that the hybridization site for the first amplification primer for generating sequencing templates from enzymatic deletions is not limited to this sequence or this location and may be any sequence or located at any position in the vector consistent with its intended purpose.

As shown in FIG. 1 and SEQ ID NO:1, in pGenDel1, the hybridization site for the second amplification primer for generating sequencing templates from enzymatic deletions is between bases 10182 and 10202 and is complementary to the primer designated oriLRr, which has the sequence GACGCTCAAGTCAGAGGTGGC (SEQ ID NO:9). However, those skilled in the art will appreciate that the hybridization site for the second amplification primer for generating sequencing templates from enzymatic deletions is not limited to this sequence or this location and may be any sequence or located at any position in the vector consistent with its intended purpose.

Following the generation of nested deletions using the techniques described below, an amplification reaction is conducted using the amplification primers for generating sequencing templates from enzymatic deletions. The amplification product is then sequenced using sequencing primers for enzymatic deletions as described below.

D. Sequencing Primers for Enzymatic Deletions

Preferably, the vectors designed for generating nested deletions using enzymatic methods, contain hybridization sites for sequencing primers for enzymatic deletions. The hybridization sites for sequencing primers for enzymatic deletions are preferably located near the end of the insert where enzymatic deletion occurred and are positioned such that they will be contained in the amplification product generated using the amplification primers for generating sequencing templates from enzymatic deletions. The sequencing primers for enzymatic deletions may have any sequence complementary to a sequence near the end of the insert where enzymatic deletion occurred. Preferably, the sequencing primers for enzymatic deletions are at least 15 nucleotides in length. More preferably, the sequencing primers for enzymatic deletions are between 15 and 25 nucleotides in length.

The hybridization sites for sequencing primers for enzymatic deletions may be from about 15 to about 300 bases from the end of the insert where enzymatic deletion occurred. Preferably, the hybridization sites for sequencing primers for enzymatic deletions are from about 15 to about 150 bases from the end of the insert where enzymatic deletion occurred. More preferably, the hybridization sites for sequencing primers for enzymatic deletions are from about 15 to about 60 bases from the end of the insert where enzymatic deletion occurred.

As shown in FIG. 1 and SEQ ID NO:1, the hybridization site for sequencing primers for enzymatic deletions is located between base 3043 and base 3059 of pGenDel1. The hybridization site for the sequencing primer for enzymatic deletions is complementary to the sequence of the primer designated as the T3 sequencing primer, which has the sequence ATTAACCCTCACTAAAG (SEQ ID NO:17). However, those skilled in the art will appreciate that the hybridization sites for sequencing primers for enzymatic deletions are not limited to this sequence or this locations and that it may be any sequence or located at any position in the vector consistent with their intended purpose.

The sequencing primers for enzymatic deletions are used to determine the sequence of inserts having deletions generated using enzymatic procedures. In such procedures, the insert is amplified using the amplification primers for generating sequencing templates from enzymatic deletions. The sequencing primers for enzymatic deletions are hybridized to the complementary sequences in the amplification product and extended in the presence of detectable dideoxy nucleotides using standard DNA sequencing techniques. The products of the sequencing reaction are then electrophoretically separated and the sequence of the inserts is read using an automated sequencer such as the ABI Prism 377 sequencers (Perkin Elmer, Applied Biosystems Division, Foster City, Calif.).

Vectors Designed for Generating Nested Deletions Using Transposition Based Methods and Enzymatic Methods The vectors of the present invention may also be designed for generating nested deletions using both transposition based methods and enzymatic methods. Such vectors are illustrated by pGenDel1. These vectors have a high copy number origin of replication having at least one cloning site therein, a low copy number origin of replication and its controlling genes, at least one copy number indicator as described above, transposition elements, at least one deletion indicator, and a maintenance marker. The transposition based deletion vectors may also have the other features described above, such as hybridization sites for insert amplification primers, hybridization sites for insert sequencing primers, and single stranded origin of replication. Furthermore, the transposition based deletion vectors may also have hybridization sites for transposition deletion amplification primers and hybridization sites for transposition deletion sequencing primers, hybridization sites for primers for creating substrates for enzymatic deletions, hybridization sites for primers for amplifying deletions, and hybridization sites for primers for sequencing deletions.

The use of each of the features described above is described further below.

I. Cloning Inserts into Cloning Sites in the High Copy Number Origin of Replication and Selection of Cells Containing Vectors Having Inserts Therein As described above, the present vectors contain cloning sites in the high copy number origin of replication which do not disrupt the ability of the origin to direct high copy number replication. The high copy number origin of replication facilitates the preparation and manipulation of vector DNA, a crucial feature which limits the applicability of the current oriS containing plasmids.

Cells carrying the pGenDel1 vector without an insert are kanamycin resistant, streptomycin sensitive, sucrose sensitive, and dark blue on Xgal and IPTG. As described in more detail below, cells carrying pGenDel1 derivatives in which inserts have been cloned into the cloning sites in the high copy number origin of replication are kanamycin resistant, streptomycin resistant (where streptomycin resistant host cells are used), sucrose sensitive, and light blue on Xgal and IPTG. Moreover, aberrant plasmids resulting from rearrangement or degradation during the cloning steps usually lack an intact lacZ gene and are easily identified due to their white coloration in the presence of IPTG/Xgal.

Upon cloning an insert into the cloning sites in the high copy number origin of replication, the function of the high copy number origin of replication is disrupted and replication of the vector is directed by the low copy number origin of replication. In addition to simplifying the generation and sequencing of nested deletions using transposition based methods or enzymatic methods as discussed below, the low copy number of the resulting recombinants allows the stable cloning of fragments from several hundreds of bases to several hundreds of kilobases in length and permits the maintenance of sequences which are unclonable in high copy number.

In pGenDel1, the unique PmlI and ScaI blunt ended cloning sites in the high copy number origin of replication (ori pUC19 derived), allow the cloning of inserts at these sites, which in turn provokes a drastic change in the number of molecules per cell. The strA+ gene carried by pGenDel1 renders streptomycin-resistant recipient cells sensitive to streptomycin when present at a high copy number. Thus, streptomycin-resistant cells transformed by a pGenDel1 plasmid without an insert in the high copy number origin of replication (ori pUC19), will be sensitive to streptomycin and unable to grow on streptomycin-containing media. However, cells containing recombinant pGenDel1 plasmids with inserts in the high copy number origin of replication (ori pUC19) will be present at low copy numbers and will be able to grow in the presence of streptomycin.

Cells containing rare spontaneous mutations which inactivate the stra+ gene would also grow on streptomycin. However, such cells can be effectively detected and rejected using the truncated LacZ color-based selection system. Cells containing pGenDel1 in high copy number will grow as deep blue colonies in the presence of Xgal and IPTG due to the multiple copies of the truncated lacZ gene. In contrast, cells containing the truncated lacZ gene at a low copy number or in a single copy are light blue in the presence of Xgal and IPTG and are easily distinguished from cells containing high numbers of the lacZ gene. Thus, cells containing recombinant pGenDel1 plasmids with a disrupted ori pUC 19, will be streptomycin resistant and light blue on Xgal and IPTG, while cells containing vectors with a spontaneous mutation in the strA+ gene will be streptomycin resistant and dark blue on Xgal and IPTG. Thus, cells containing vectors with spontaneous mutations in the strA+ gene can be easily discarded based on their color on medium containing Xgal and IPTG.

The selection procedure described above is so effective in isolating recombinant clones harboring an insert within the ori pUC 19, that it is not obligatory to isolate the linear plasmid DNA on a gel after digestion, nor to subject it to a dephosphorylation procedure, although dephosphorylation may be performed if necessary to further decrease the background. When transformed into cells carrying a chloramphenicol resistance gene on a plasmid other than pGenDel1, pale blue colonies typically represented 90%, and in all cases no less than 50%, of resistant colonies on kanamycin, chloramphenicol, streptomycin, IPTG/Xgal containing medium; of these, 95% contained an insert.

Example 1 describes the selection and sequencing of pGenDel1 derivatives having inserts cloned into the high copy number origin of replication.

EXAMPLE 1

A. Preparation of Insert DNA

A bacterial artificial chromosome (BAC) clone (B0166G11) containing a 145 kb human genomic DNA insert in pBeloBAC11 vector was grown overnight in LB broth containing 12.5 µg/ml of chloramphenicol. DNA was extracted by the alkaline lysis method and treated with RNAse. The supercoiled DNA band was isolated by Ethidium bromide/CsCl gradient centrifugation. Ethidium bromide was removed by passing the resulting material through Biorad AG50 resin. 3 µg of the resulting BAC DNA in 3 µl of 10 mM TrisHCl 1 mM EDTA pH 7.5 was sonicated using a XL2020 sonicator (available from Misonix) by 10 pulses of 0.5 second with 2 second intervals at maximum energy setting. The sonicated DNA was concentrated by Microcon 100 centrifugation. The concentrated DNA was size-fractionated by preparative 1% agarose gel electrophoresis. The resulting fractions of 4–6 kb size were excised and DNA was extracted by electroelution and subsequent concentration on Microcon 100 columns.

The ends of the resulting DNA fragments were repaired by treatment with 4 units of Vent DNA polymerase (New England Biolabs) in the presence of 125 µM of all four dNTPs, for 20 minutes at 72° C. in a final volume of 20 µl of ThermoPol buffer supplied by the manufacturer. The DNA was extracted with chloroform, precipitated in ethanol and resuspended in 10 mM Tris-HCL pH 7.5, 1 mM EDTA. DNA concentrations were estimated by relative fluorescence of agarose gels containing lambda phage DNA samples of known concentrations.

B. Preparation of Vector DNA pGenDel1 vector DNA was extracted from overnight cultures by the standard alkaline lysis procedure. In order to check the integrity of the vector, 1 µl of the overnight cultures was plated on LB agar containing either sucrose and kanamycin or streptomycin and kanamycin. Only cultures giving no more than 5–10 resistant colonies in these tests were used for further DNA extraction. Supercoiled plasmid was obtained by Ethidium bromide/CsCl gradient centrifugation. 2 µg of the resulting plasmid DNA was then digested with 10 units of ScaI enzyme, in conditions recommended by the manufacturer (New England Biolabs). After adding EDTA at a 10 mM concentration, the vector DNA was extracted with phenol, and concentrated by Microcon 100 centrifugation.

C. Ligation of Insert DNA into Vector and Selection of Clones Having Inserts 10 ng of pGenDel1 vector DNA was then ligated in a 10 µl reaction volume, with 50 ng of the BAC fragment DNA, in the presence of 200 units of T4 DNA ligase (Epicentre) according to manufacturer's recommendations, at 12° C. overnight. Following addition of 20 µg of bacterial tRNA, the ligation products were extracted with phenol and precipitated in ethanol.

D10HB cells containing or lacking the transposase expression plasmid pXRD4043 were washed, and subjected to electroporation in the presence of the purified ligation products, in a 40 µl final reaction volume. Following the addition of L broth, the mixtures were incubated for 45 minutes at 30° C. (to reduce transposition), and plated in 20 µl aliquots on the surface of 100 mm Petri dishes containing 2% agar-LB, 20 µl kanamycin, 20 µg/ml chloramphenicol (in procedures using DH10 B cells containing pXRD4043, which confers chloramphenicol resistance), 100 µg/ml streptomycin, IPTG and Xgal. Following incubation for 24 hours at 30° C., white, pale blue and dark blue colonies were scored.

The results were as follows. For DH10B cells lacking the pXRD4043 plasmid, the plates contained 10–60 colonies which were all pale blue. No white or deep blue colonies were observed.

For DH10B cells containing the pXRD4043 plasmid, pale blue colonies represented 70% to 100% of all resistant colonies, with an average of 95%.

Only pale blue colonies, representing 50% to 90% of all resistant colonies, were selected for further experiments. Dark blue colonies resulting from spontaneous mutations in the rpsL gene, did not account for more than a few percent of total resistant colonies. The number of white colonies resulting from degradation of the vector at any stage during the above mentioned preparation steps varied in number depending upon the quality of the restriction and ligation enzymes used, as well as upon the purity of the sonicated/repaired fragments.

Alternatively, recombinant plasmids were obtained by electroporation of above mentioned ligation products into D10HB cells. After incubation on 2% agar-LB, 20 µg/ml kanamycin, 100 µg/ml streptomycin, IPTG and Xgal Petri dishes at 37° C., pale blue recombinant colonies were isolated, the transposase expression plasmid pXRD4043 was inserted by electroporation and the resulting mix was plated on kanamycin/chloramphenicol containing Petri dishes at 30° C. These two methods gave essentially similar results.

D. Analysis of Positive Clones

Inserts in positive colonies obtained following electroporation of DH10B cells containing or lacking the pXRD4043 plasmids were amplified by Long Range PCR with the primers oriLRr and oriLRd. (Long Range PCR, Barnes, W. M., *Proc. Natl. Acad. Sci. USA* 91: 2216–2220, 1994, the disclosure of which is incorporated herein by reference) Positive colonies were resuspended in 30 µl of water, and 10 µl of the resulting solution was used to run a PCR reaction in a 30 µl final volume according to the conditions recommended in the GeneAmp XL PCR kit (PE Applied Biosystems) at 68° C. with 4 minutes of elongation. One third of the PCR reaction product was loaded on 1% agarose gel in Tris-acetate-EDTA buffer and subjected to electrophoresis at 80 V for 2 hours. For DH10B cells lacking the pXRD4043 plasmid, out of 36 colonies tested, 28 gave inserts of 4–6 kb, 3 contained inserts of less than 600 bp and 5 failed to amplify any product.

For DH10B cells containing the pXRD4043 plasmid, out of 192 colonies tested 19 had inserts of less than 400 bp in length, 26 had inserts between 400 bp and 1 kb in length, 5 had inserts between 1 kb and 5 kb in length, 130 had inserts between 4 and 7 kb in length, and 12 gave no amplification product.

On average, 90%–95% of the colonies contained an insert and 70–80% of the colonies contained inserts in the expected size range of 4–7 kb.

The ends of the inserts present in the PCR products were sequenced on ABI automatic sequencers using the OS1 and OR1 primers.

Figure 2A:
FIGS. 2A–2C summarize the procedures for cloning inserts into the vectors of the present invention, selecting cells containing derivatives of the vectors of the present invention having inserts cloned therein as well as a procedure for generating vectors having transposition-based deletions in the inserts and selecting cells containing such vectors.
Figure 2B:
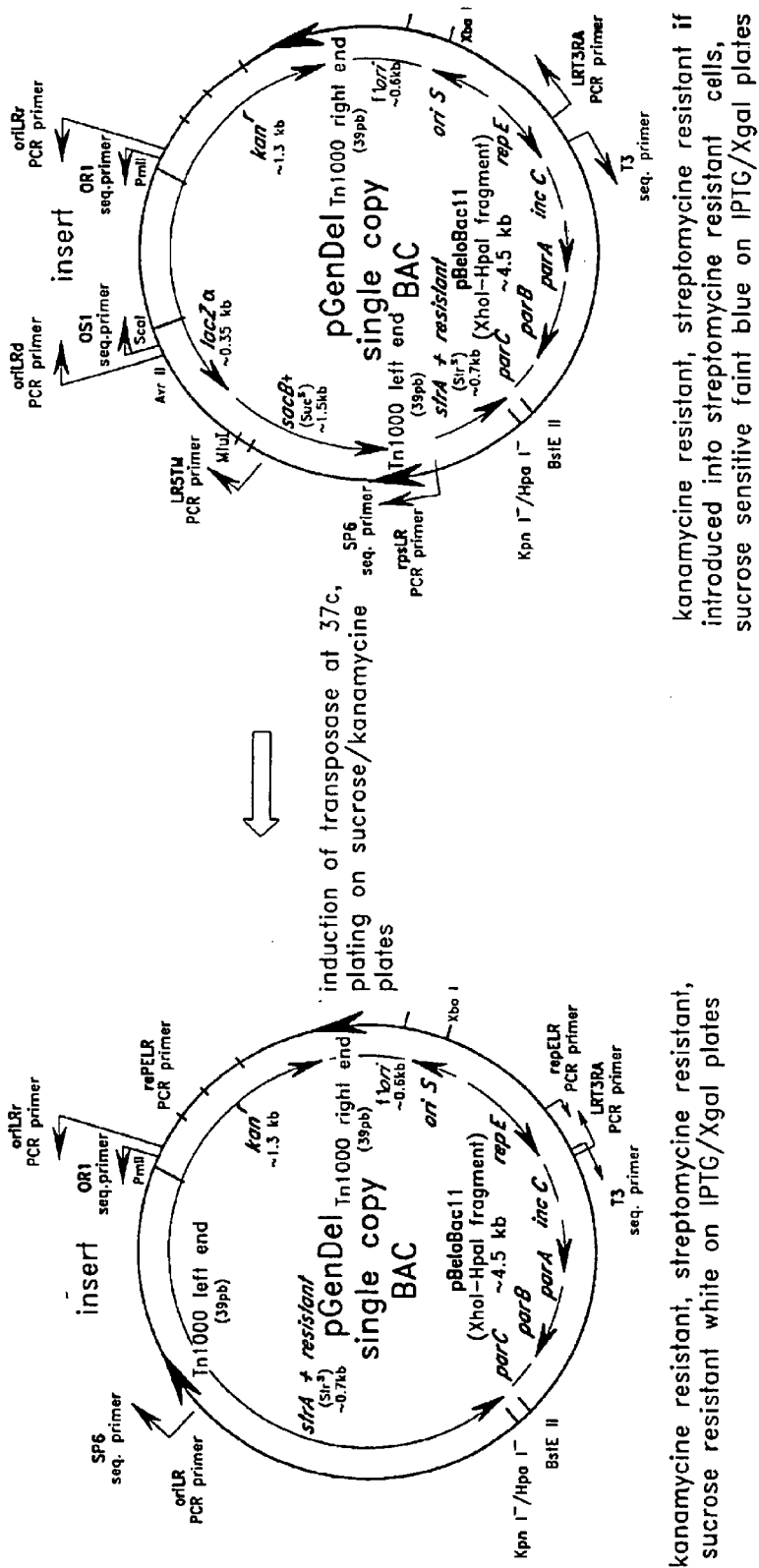

The cloning and selection of pGenDel1 recombinants having inserts in the high copy number origin of replication is summarized in the section of FIG. 2B in which the insert is cloned into pGenDel1. As indicated in FIG. 2B, cells containing pGenDel1 derivatives containing an insert are kanamycin resistant, streptomycin resistant, sucrose sensitive and faint blue on IPTG/Xgal plates. Thus, such cells can be selected and identified on IPTG/Xgal plates containing kanamycin and streptomycin.

II. Generation and Analysis of Nested Deletions Using Transposition Based Methods For the generation of nested deletions by transposition, pGenDel1 is introduced into cells containing a source of transposase. As described above, the bacterial strain D10HB, containing the plasmid pXRD4043 (Tsai, M.-M., Wong., R. R., Hoang, A. T., Deonier, R. C. (1987) J. Bacteriol. 169, 5556–5562.) was used for the initial cloning of inserts into pGenDel 1 pXRD4043 is a moderate copy number pACYC184 plasmid which contains the tnpA gene under the control of a synthetic tac promoter. As a selectable marker, pXRD4043 contains the chloramphenicol resistance gene. However, it will be appreciated that the selectable marker on the plasmid which serves as a source of transposase may be any of a variety of selectable markers, provided that the same selectable marker is not on the vector containing the insert in which deletions are to be generated.

Initially, the cells are grown at 30° C. in order to restrict transposition. When cells are cultivated at 37° C., the transposase becomes active and mediates the intramolecular transposition of the Tn1000 ends within pGenDel1. Transposition based deletions which result in linking the left transposon end to any position within the cloned insert will remove both the SacB and lacZ genes but leave the kanamycin resistance gene intact. Thus, cells containing clones which have undergone such transposition based deletions are able to grow in the presence of kanamycin (kan$^R$), are white in the presence of IPTG and X-gal (lacZ$^-$) and grow in the presence of sucrose (SacB$^-$). In addition, where streptomycin resistant host cells are used, the cells are streptomycin resistant, since the strA+ gene is present in low copy number.

Currently available vectors for generating nested deletions using transposition based methods are present in high copy number, thereby necessitating multiple transformation steps to recover pure colonies containing only vectors containing deleted inserts. Since pGenDel1 is present in a single copy following the cloning of an insert into the high copy number origin of replication, it is not necessary to retransform these plasmids in order to obtain pure final subclones. In fact, the majority of sucrose resistant, kanamycin resistant, white colonies are derived from intramolecular transposition linking the left transposon end to variable points within lacZ or the insert.

Due to the single copy nature of transposition based nested deletions in recombinant pGenDel1 vectors, the most efficient way to generate sequencing templates is to run a PCR (Polymerase Chain Reaction) under conditions favoring high fidelity, long reading amplification (Long Range PCR, Barnes, W. M., *Proc. Natl. Acad. Sci. USA* 91: 2216–2220, 1994). For this purpose, the rpsLR and oriLRr primers are used. This set of primers allows the efficient and faithful amplification of inserts of up to 10 kb from bacterial cells containing recombinant pGenDel1 vectors having inserts therein. In such procedures, 0.5 µl of an overnight suspension of bacterial cells harboring pGenDel1 derivatives with transposition based deletions in the inserts were used to start a long range PCR reaction with the rpsLR/oriLRr primers.

Since the selected transposition events in the pGenDel1 system only proceed from one end, the minimal tiling path clones containing progressing, overlapping deletions can be determined by simple size determination of inserts. As used herein, the terminology minimal tiling path refers to a series of deletions sharing a common end point which are spaced such that the difference in length between two successive deletions is close to the maximum length routinely sequenceable. In this way, the entire sequence of the insert can be determined by sequencing the minimum number of deletions possible.

Randomly picked subclones were grown for four hours in LB broth containing 20 µg/ml kanamycin and the resulting cultures were centrifuged in microplates. The cell pellets were resuspended in water and used to initiate a long range PCR reaction with primers rpSLR and oriLRr. After the PCR, part of the reaction product was loaded on a 1% agarose gel in TAE buffer and the molecular weight of inserts was determined by comparison with molecular weight markers. Minimal tiling path clones were chosen in order to allow a 300–500 bp difference between two successive deletion fragments, resulting in the selection of ~20 subclones for an insert size of ~4 kb.

The sequence of 99% of the entire ~4 kb original insert was obtained after fluorescent automatic cycle sequencing of the ~20 selected PCR products using the SP6 sequencing primer.

If necessary, more clones can be used as templates in problem regions resulting from the presence of repeats or high GC content DNA. Moreover, particularly difficult regions could be re-sequenced by primer walking from the opposite strand.

The minimal tiling path approach greatly reduces contigation efforts, since the position of problem regions can easily be determined from the size of the corresponding deletion.

Example 2 describes the selection of transposition based deletions and the identification of clones containing minimal overlaps.

EXAMPLE 2

Transposition based deletions were obtained from eight pGenDel1 sub-clones having the following inserts derived from the bacterial artifical chromosome clone BAC B0166G11:

B0166G11.D10, containing a 4200 bp insert

B0166G11.C03: containing a 5100 bp insert

B0166G11.D05: containing a 5300 bp insert

B0166G11.G06: containing a 5300 bp insert

B0166G11.D03: containing a 4500 bp insert

B0166G11.E07: containing a 4500 bp insert

B0166G11.A04: containing a 4200 bp insert

B0166G11.G05: containing a 5100 bp insert

These pGenDel1 subclones were obtained in cells containing pXRD4043 as described in Example 1 above. The pGenDel1 subclones were grown in 1 ml of LB containing 40 µg/ml kanamycin, and 12 µg/ml chloramphenicol at 30° C. overnight. After incubation for one hour at 37° C. to induce transposition, 4 µl of each resulting cell suspension was spread onto 140 mm Petri dishes containing 1% agar LB, 40 µg/ml kanamycin, 7.5% sucrose containing IPTG and X-Gal. After incubation at 37° C., the subclones gave varying numbers of kanamycin resistant, sucrose resistant, white colonies (containing transposition mediated deletions) ranging from 1600 to 200 per clone, with 10%–30% of blue colonies. 48 kanamycin resistant, sucrose resistant, white colonies for each subclone were picked and resuspended in 30 µl of water. 10 µl aliquots were used for a long range PCR reaction with the primers rpsLR/oriLRr under the conditions recommended in the GeneAmp XL PCR kit (PE Applied Biosystems), in a 30 µl final volume at 68° C., with a 4 minute elongation step. The reaction products were analyzed by electrophoresis in a 1% agarose gel. More than 95% of all kanamycin resistant, sucrose resistant, white colonies analyzed gave distinct PCR products with the sizes expected for transposon mediated deletions in the cloned insert. After a preliminary analysis of the deletion sizes, the PCR products corresponding to deletions differing in size by 300–500 bp were deposited in adjacent wells of an agarose gel and analyzed by electrophoresis.

Out of 48 transposon-mediated deletions, 18–20 clones giving a minimal tiling path for more than 90% of the initial subclone length were selected for further analysis. The long range PCR products were used as a template for automatic fluorescent sequencing of the deletions using the SP6 universal primer.

Figure 2C:
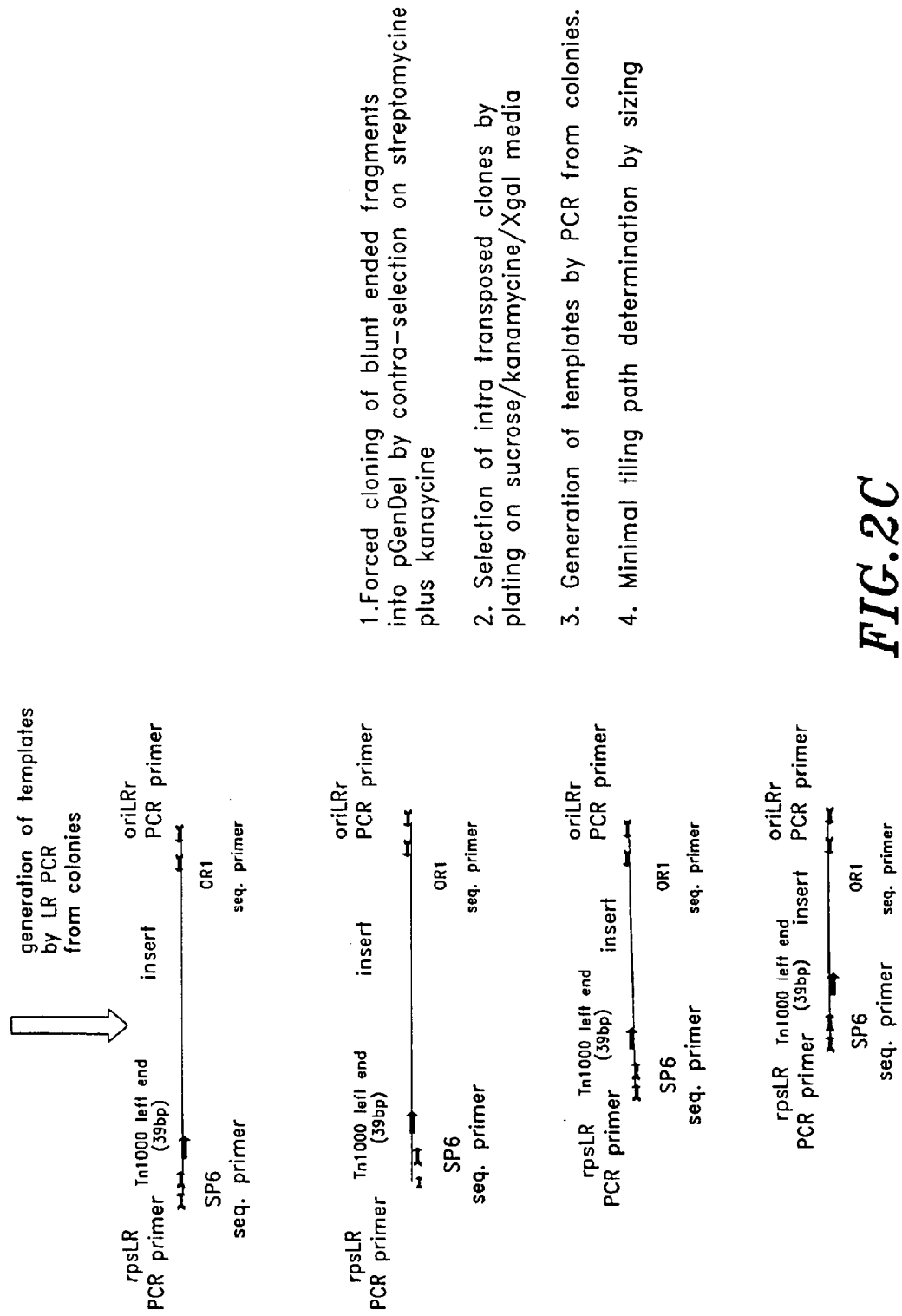

FIGS. 2A–2C summarize the procedure for obtaining and sequencing nested deletions using transposon based methods.

III. Generation and Sequencing of Nested Deletions Using Exonuclease III

Transposition of Tn1000 is only weakly sequence specific. Nevertheless, the immense variation of genomic sequences in higher eucaryotes may result in some clones being either resistant to transposition or containing preferential sites for it (hot spots of transposition). Therefore, for the corresponding DNA regions, it will be necessary to generate and analyze more subclones in order to obtain a minimal tiling path of overlapping clones. In practice, one can expect occasional gaps in the sequence due to this bias of transposition. In order to overcome this limitation, pGenDel1 was designed to also permit the generation of nested deletions using enzymatic methods.

Since pGenDel1-based subclones are single copy plasmids, the main problem in applying classic enzymatic methods is the poor availability of intact supercoiled plasmid DNA in microgram quantities. Another general problem associated with classic exonuclease-based methods is the necessity to obtain a specific cut in the vicinity of the insert and to block the 3' end of the opposite DNA strand.

In order to overcome both of these problems, a new method for generating templates for exoIII action was developed. pGenDel1 is adapted to facilitate the application of this new method. The method is performed as follows.

As illustrated in FIG. 3A, amplification of subclone DNA using the primers SLR3 and LRT3RA under long range PCR conditions gives rise to a fragment containing the truncated lacZ gene, the cloned insert, the kanamycin resistance gene, oriS, and the repE gene (which is necessary for replication from oriS). Circularization of the resulting amplification product generates a smaller, stable, viable plasmid, containing the original insert which confers resistance to kanamycin and gives blue colonies in the presence of IPTG and X-gal. In addition, since the amplification product lacks the sacB gene, cells containing the amplification product are sucrose resistant (while cells containing the parent plasmid possess the sacB gene and are sucrose sensitive). Because the cells containing the amplification product do not have the strA+ gene present at a high copy number, if the circularized amplification product is introduced into streptomycin resistant host cells the host cells remain streptomycin resistant. The circularized amplification product, which lacks the incC, par A, par B, and par C genes, replicates at a slightly elevated number of copies and gives 2–5 fold higher yields of plasmid DNA per cell than full length pGenDel1 recombinants.

The stable, moderate copy number of the recircularized amplification products allows the efficient generation and recovery of plasmids with exoIII nested deletions starting from the truncated lacZ gene of pGenDel1 and progressing into the insert.

Figure 3B:
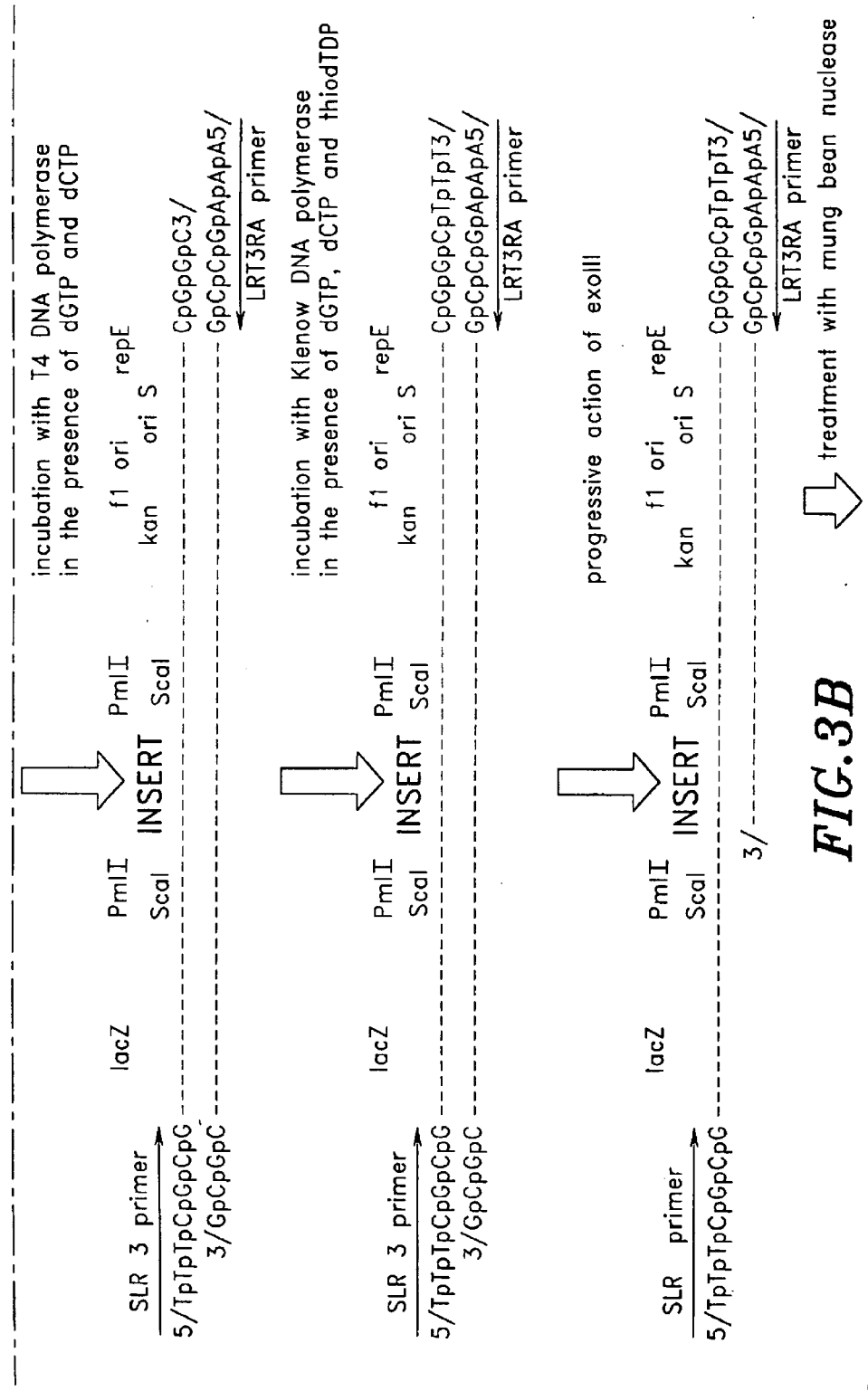

The pGenDel1 vector is designed to permit unidirectional Exonuclease III digestion. As shown in FIG. 3A, due to the sequence of the SLR3 primer, the long range PCR product made from the initial recombinant pGenDel1 derivative contains at its left end (proximal to the lacZ sequence) a tract of three thymidines followed by the sequence CGCG. Due to the sequence of the LRT3RA primer, the right end of the amplification product (near the repE gene) contains three adenosines, followed by the sequence GCCG. When the PCR product is treated with T4 DNA polymerase, (which exhibits a powerful 3' exonuclease activity) in the absence of dTTP and dATP, but in the presence of dGTP and dCTP the two opposite ends will contain 5' overhangs of TTT and AAA respectively. The subsequent action of Klenow DNA polymerase in the presence of dGTP, dCTP and alpha thio thymidine diphosphate will result in the right end (the end near the repE gene) being modified by thio substitution at its 3' end. The thio substitution renders the right end inactive as a substrate for exoIII action. However, the recessed 3' strand on the left end is available for digestion by exonuclease III (FIG. 3B).

During Exonuclease III treatment, aliquots are withdrawn at regular time intervals. Thereafter, the Exonuclease III digested vectors are treated with the single strand specific mung bean nuclease (New England Biolabs) to digest the 5' overhanging strand. Due to the processive nature of exoIII action, the deletions obtained are proportional to time of incubation with Exonuclease III. The time intervals necessary to produce clones differing by 300 bp can be deduced from calibration experiments. In this scheme, aliquots are withdrawn at regular time intervals and their sizes are analyzed on an electrophoresis gel. Those containing digested material differing by ~300 bp are used for ligation and electroporation of D10HB cells as discussed below. As an alternative, all the aliquots corresponding to different incubation durations can be pooled and subjected to preparative electrophoresis. The fractions differing by 300 bp can be used for ligation and electroporation.

The product resulting from Exonuclease III and mung bean nuclease digestion is then recircularized with DNA ligase and used to transform D10HB cells. Plasmids that contain progressive nested deletions of the initial insert will render the transformed cells kanamycin resistant and white on IPTG and Xgal. (FIG. 3C) In contrast, original PCR products which for some reason escaped digestion will still contain the lacZ gene. Thus, cells transformed with recircularized original PCR products will be kanamycin resistant and blue in the presence of Xgal and IPTG. PCR products in which the thio blocking treatment was ineffective such that they are deleted from both ends will not give rise to viable plasmids due to inactivation of the repE gene which is essential for plasmid replication from oriS. Cells transformed with a recircularized PCR product in which digestion proceeded into the kanamycin resistance gene will be unable to grow on medium containing kanamycin.

The inserts present in the resulting clones can be amplified by long range PCR between primer repELR, situated in repE, and primer oriLRr. This permits the analysis of the clones before their sequencing. The resulting minimal tiling path PCR fragments are sequenced using the T3 sequencing primer that was inserted between repE and incC during pGenDel1 construction.

Example 3 describes the generation of nested deletions using Exonuclease III.

EXAMPLE 3

Cells harboring sub-clone B180G09.H05 in pGenDel1 were cultured overnight in L Broth. 100 µl of this culture were centrifuged and the cells were resuspended in 1.25 ml of 10 mM TrisHCL pH 8.0, 1 mM EDTA. 8 µl of this solution were used to start a PCR reaction in a 50 µl total volume, with 20 pM each of the SLR3 and LRT3RA primers under the conditions recommended in the GeneAmp XL PCR kit (PE Applied Biosystems). The following cycles were performed on a PTC-200 (MJ RESEARCH) thermocycler.

A hot start was conducted at 94° C. for 3 minutes, during which $Mg(Oac)_2$ was added. Denaturation proceeded for 15 seconds at 94° C. followed by 20 cycles of elongation for 13 minutes at 66° C. 15 cycles of elongation at 68° C., with an elongation time of 13 minutes and a ramp of 15 seconds per cycle were then conducted. Elongation was performed at 72° C. for 10 minutes.

This procedure gave from 1 to 5 µg of PCR product. The entire volume of the PCR reaction was diluted into 500 µl of Tris, EDTA(10.1), passed through a Microcon 100 column, and washed with another 500 µl of TE (10.1). 6 µl of DNA solution were obtained as a result of this purification step.

A 1 µl aliquot of the DNA solution in TE (10.1) was added to a solution containing 5 µl dGTP, dCTP (2 mM), 5 µl T4 DNA polymerase buffer, 0.5 µl of 1% BSA solution, 33.5 µl $H_2O$. After preheating for 5 minutes at 37° C., 2 µl (3 units/µl) of T4 polymerase (Biolabs) were added. Following incubation at 37° C. for 10 minutes, 2 µl of alpha thio thymidine diphosphate (2,5 mM) and 1 µl of Klenow (5 units/µl) were added. Incubation was continued for another 15 minutes at 37° C. The solution was deproteinized by phenol/chloroform extraction and the DNA was precipitated with ethanol and resuspended in 5 µl of TE(10.1).

5 µl of DNA in TE were mixed with 5 µl β mercaptoethanol (100 mM), 25 µl 2× exo buffer (Stratagene) and 14 µl of water. One hundred units of exonuclease III (Stratagene) was added to this solution. The mixture was pre-incubated for 5 minutes at 37° C. 5 µl samples were withdrawn at 30 second intervals and added to 15 µl of mung bean mix. The mung bean mix was prepared by mixing 22 µl of 10× mung bean buffer, 143 µl of water and 1 unit of mung bean (Biolabs) and was kept in ice before use. After all time aliquots were withdrawn the samples were incubated at room temperature for 30 minutes.

Aliquots of these samples were run on agarose gels to evaluate the extent of exonuclease III digestion. Progressively shorter reaction products were observed with increasing digestion periods.

The reactions were stopped by adding 2 µl of a solution of 1M TrisHCl pH 7.5, 25 mM EDTA. Each sample was extracted with an equal volume of phenol/chloroform. After ethanol precipitation, the DNA was resuspended in 50 µl of ligation buffer supplemented with ATP and containing 1 unit of DNA ligase (Boehringer). Ligation was conducted overnight at 16° C. After chloroform deproteinization and precipitation with ethanol, the ligation products were dissolved in 5 µl of 10 mM TrisHCl pH7.5, 1 mM EDTA and 2 µl were electroporated into DH10B cells. The transformed cells were spread onto LB agar plates containing 40 µg/ml of kanamycin, with IPTG and Xgal.

Figure 3C:
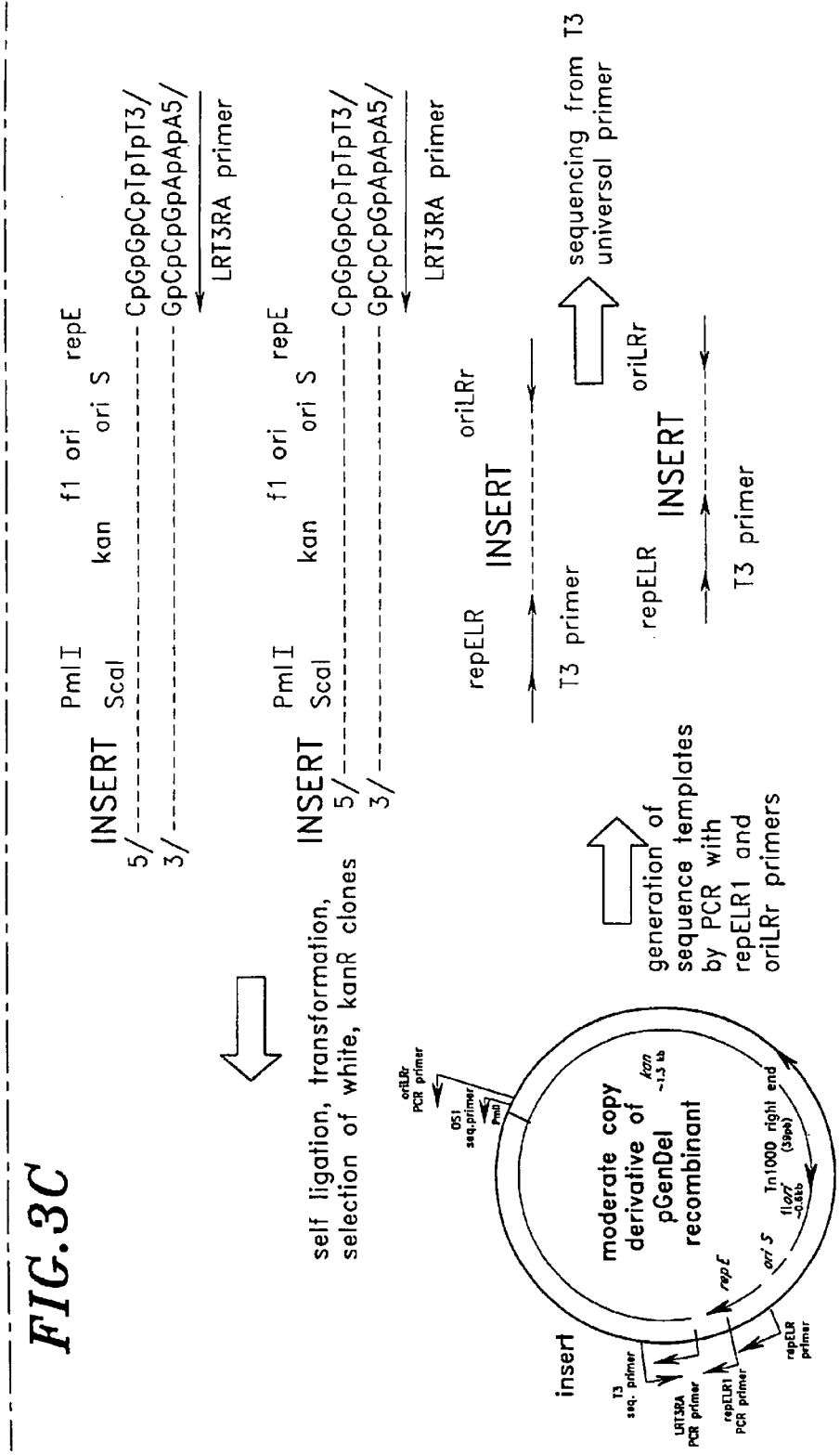

The nested deletions may be sequenced by amplifying the deleted insert with the repELR and oriLR primers and sequencing the amplification product with the T3 primer. FIGS. 3A–3C summarize the procedure for generating and sequencing nested deletions using Exonuclease III.

V. Generation and Sequencing of Nested Deletions Using Mung Bean Nuclease

During the experiments generating exoIII nested deletions described above, it was discovered that when the initial long range PCR products generated using the LRT3RA and SLR3 primers as described above were treated with a commercial preparation of mung bean nuclease nested deletions distributed throughout the region containing the lacZ alpha peptide gene and the cloned insert were recovered upon self ligation and transfection into D10HB cells plated onto kanamycin containing medium. These deletions resulted from either small amounts of double strand specific activity in the mung bean nuclease preparation or from a double stranded activity of mung bean nuclease itself when present in high concentrations.

Figure 4B:
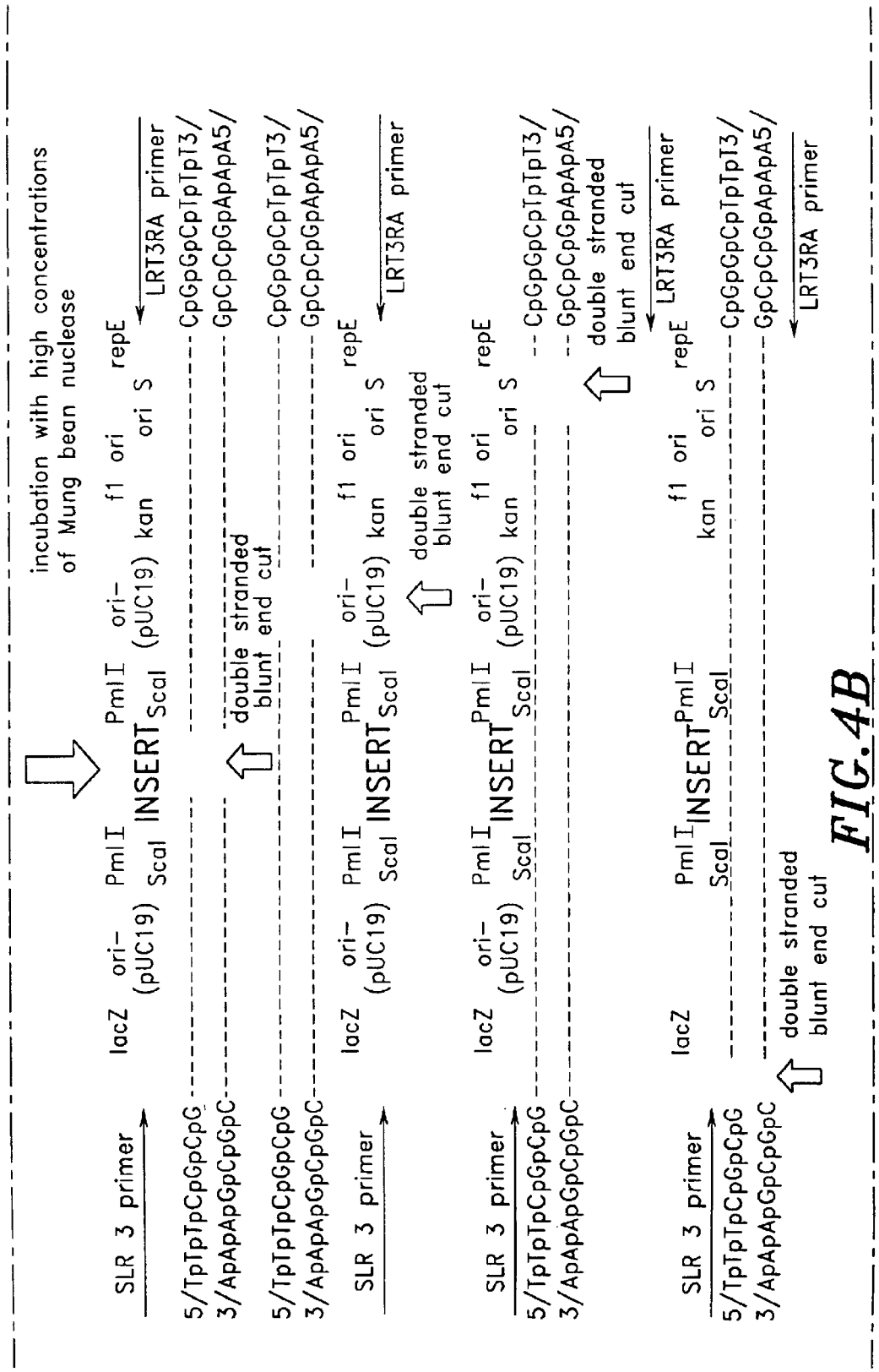
Figure 4C:
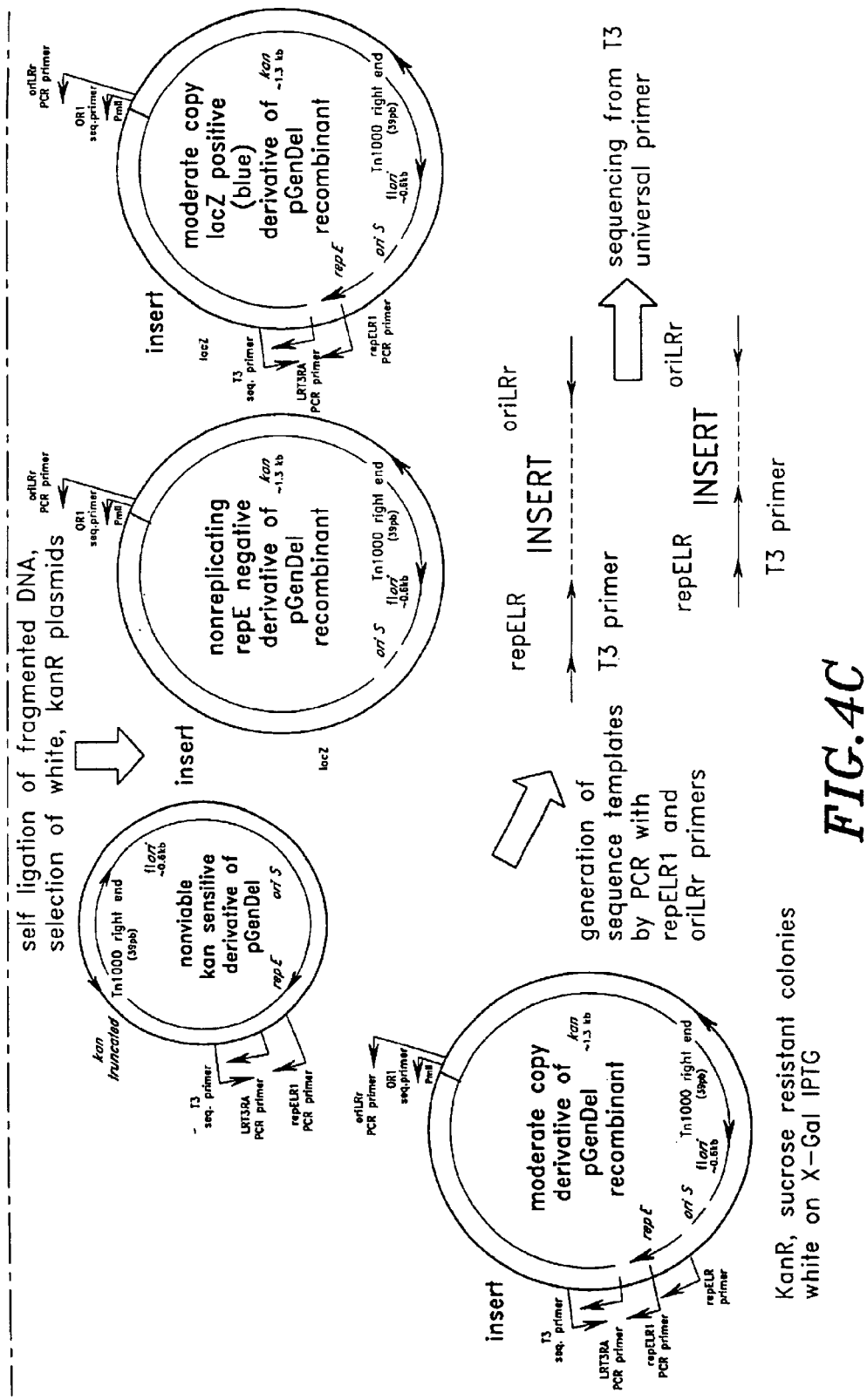

The distribution of the recovered deletions in the lacZ gene and the inserts is a consequence of the structure of pGenDel1. As shown in FIG. 4C, after self-ligation and transformation, only cells containing plasmids with an intact kan$^R$gene and repE gene are able to grow on kanamycin. In addition, as described above with respect to the ExoIII deletions, since the amplification product lacks the sacB gene, cells containing the amplification product are sucrose resistant (while cells containing the parent plasmid possess the sacB gene and are sucrose sensitive). Because the cells containing the amplification product do not have the strA+ gene present at a high copy number, if the circularized amplification product is introduced into streptomycin resistant host cells the host cells remain streptomycin resistant.

The circularized amplification product, which lacks the incC, par A, par B, and par C genes, replicates at a slightly elevated number of copies and gives 2–5 fold higher yields of plasmid DNA per cell than full length pGenDel1 recombinants. Cells carrying vectors with deletions extending through the lacZ gene and into the insert, i.e. those cells carrying vectors with the desired nested deletions, will be kanamycin resistant and white on Xgal and IPTG. In contrast, cells containing plasmids resulting from recircularization of the initial long range PCR product will be kanamycin resistant and blue on Xgal and IPTG. Cells having plasmids harboring a small deletion in lacZ will give rise to light blue colonies. However, the small sized version of lacZ gene (350 bp) present in pGenDel1 should statistically maximize the number of deletions occurring within the inserts. Plasmids in which deletions have progressed into the repE gene will be unable to replicate since this gene is required for replication from oriS. Thus, the structure of pGenDel1 allows selection of cells having plasmids bearing deletions in the insert.

The same set of primers used to amplify the inserts in nested deletions generated with Exonuclease III (the repELR and oriLRr primers) is used to amplify the inserts from subclones produced by the mung bean-based forced deletion method. The minimal tiling path of clones is picked after their sizing is determined and the resulting minimal tiling path PCR fragments are sequenced using the T3 sequencing primer that was inserted between repE and incC during pGenDel1 construction. FIGS. 4A–4C summarize the procedure for generating and sequencing nested deletions using mung bean nuclease.

Example 4 describes the mung bean nuclease method for generating nested deletions.

EXAMPLE 4

Cells carrying subclone B0180G09.H05 in pGenDel1 were cultivated overnight in L broth. 100 µl of this culture were centrifuged and the cells were resuspended in 1.25 ml of 10 mM TrisHcl pH8.0, 1 mM EDTA. 8 µl of this solution were used to start a PCR reaction in 50 µl total volume, with 20 pM of each SLR3 and LRT3RA primers under the conditions recommended in the GeneAmp XL PCR kit (PE Applied Biosystems). Cycles were as follows:

a denaturation step of 15 seconds at 95° C.;

20 cycles of elongation for 13 minutes at 66° C.;

15 cycles of elongation at 68° C., with an initial elongation time of 13 minutes and a ramp of 15 seconds per cycle;

an elongation step at 72° C. for 10 minutes.

This usually gave from 1 to 5 µg of PCR product. The entire volume of the PCR reaction was diluted into 500 µl of water, passed through a Microcon100 column, and washed with another 500 µl of water. This resulted in 6 µl of DNA solution. A 1 µl aliquot of this solution was added to 7 µl of Mung bean buffer (50 mM sodium acetate, pH5.0, 30 mM NaCl, 1 mM ZnSO4) containing 0.8 µl (5 units) of Mung bean nuclease (New England Biolabs). After incubation at 30° C. for 30 minutes, 6 µl of 1 M Tris-HCl pH 8.5, 25 mM EDTA and 10 µl of yeast tRNA (500 µg/ml) was added, the DNA was deproteinized by phenol/chloroform extraction, and the DNA was precipitated with ethanol. The precipitate was dissolved in 41 µl of water, 5 µl of 10× ligase buffer, and 2 µl of 25 mM ATP were added together with 2 µl (20 units) T4 DNA ligase (Epicentre). The ligation was conducted overnight at 16° C. After chloroform deproteinization and precipitation with ethanol the ligation products were dissolved in 5 µl of 10 mM Tris-HCl pH 7.5, 1 mM EDTA and 2 µl were electroporated into D10HB cells. The transformed cells were spread onto LB agar plates containing 20 µg/ml of kanamycin, IPTG and Xgal.

96 kanamycin resistant, white colonies were picked and resuspended in 30 µl water. 10 µl aliquots were subjected to Long Range PCR reactions with the primers repELR/oriLRr under conditions recommended in the GeneAmp XL PCR kit (PE Applied Biosystems), in a 30 µl final volume, at 68° C. with a 4 minute elongation step. The reaction products were analyzed by electrophoresis in a 1% agarose gel. After a preliminary analysis of the deletion sizes, the PCR products corresponding to deletions differing in size by 300–500 bp were deposited in adjacent wells of an agarose gel and analyzed by electrophoresis. Out of 96 mung bean nuclease generated deletions, 30 clones giving a minimal tiling path for more than 90% of initial sub-clone length were identified.

The resulting PCR product was used as template for automatic fluorescent sequencing of resulting deletions from the T3 universal primer.

Figure 5B:
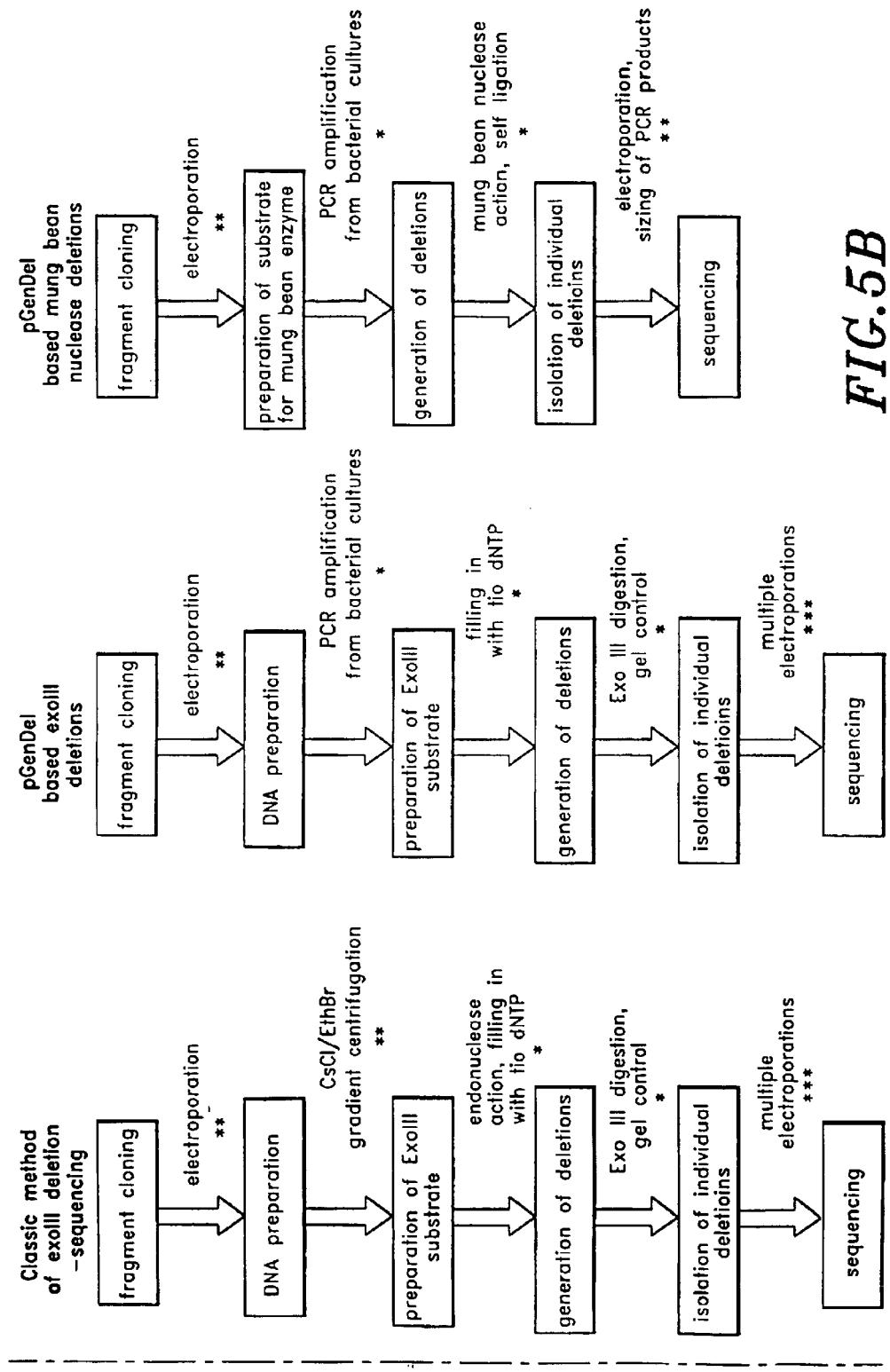

FIGS. 5A and 5B compare the steps in the classic procedures for generating nested deletions using transposition-based and enzymatic processes with the steps required when pGenDel1 is used. As shown in FIGS. 5A and 5B, pGenDel1 eliminates difficult or very difficult steps in each of these procedures, simplifying the industrial production of nested deletions and the sequencing of large genomes.

VI. Generation of Templates for Sequencing by Single Stranded Replicon Rescue

The methods of template generation described above are based on the ability to faithfully amplify relatively large fragments of DNA. Indeed, in the majority of cases, the resulting templates give high quality sequence either with fluorescent primer or fluorescent di-terminators.

Nevertheless, some simple repeats trigger sequence ambiguities because of polymerase slippage during PCR. Because of this, it is preferable to have an alternative method of template generation. It is to this end that pGenDel1 contains the origin of single stranded phage replication (f1 ori), which enables the production of single-stranded templates upon infection or transfection of cells containing recombinant plasmids which produce helper M13 phage. This can be achieved in bacterial strains containing F pili but no F factor. Such a derivative of D10HB strain can easily be constructed by genetic engineering methods which are well known by those skilled in the art. F episome genes necessary for the production of f pili are closely linked within a 33360 bp fragment described by Penfold, S. S., Simon, J. and Frost, L. S., Regulation of the expression of the traM gene of the F sex factor of *Escherichia coli*. Mol. Microbiol. 20 (3), 549–558 (1996), the disclosure of which is incorporated herein by reference. Cloning of this fragment into any F episome F compatible low copy vector or inserting it into a bacterial genome, either directly or by the help of lysogenic lambda phage, will create bacterial strains expressing f pili necessary for infection with single stranded bacteriophages in the absence of F episome immunity.

VII. Multiple Nucleation Point Walking Sequencing Strategy

Another aspect of the present invention is a multiple nucleation point sequencing method for reducing the sequencing redundancy required to assemble a complete or nearly complete sequence. The method is based on the construction of nested deletions using the transposition based or enzymatic approaches described above. The new method is facilitated by the features of vectors such as pGenDel1. In addition to simplifying nested deletion generation, pGenDel1 permits intrinsically unstable regions to be stably maintained as described above. This alleviates problems with gaps in the sequence often encountered when such unstable regions are cloned into other vectors.

Currently available procedures for constructing contigs and assembling complete or nearly complete sequences result in the same DNA being sequenced multiple times (i.e. sequencing redundancy). Sequencing redundancy results from the fact that it is currently impossible to directly sequence large DNA inserts such as the 80 kb to 250 kb inserts typically cloned in bacterial artificial chromosomes (BAC). As a result, it is necessary to subclone the BAC insert as shorter fragments of 10 kb or less and thereafter to order the subcloned fragments with respect to one another in order to determine the full sequence of the BAC insert.

Figure 6:
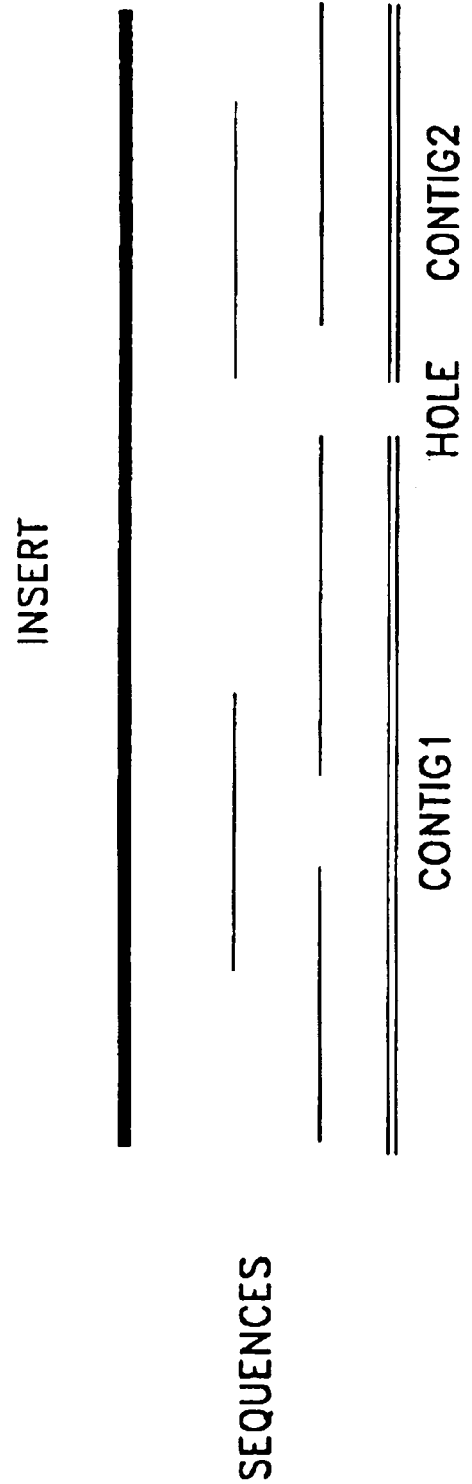
FIG. 6 is a summary of the shotgun sequencing strategy.
Figure 9A:
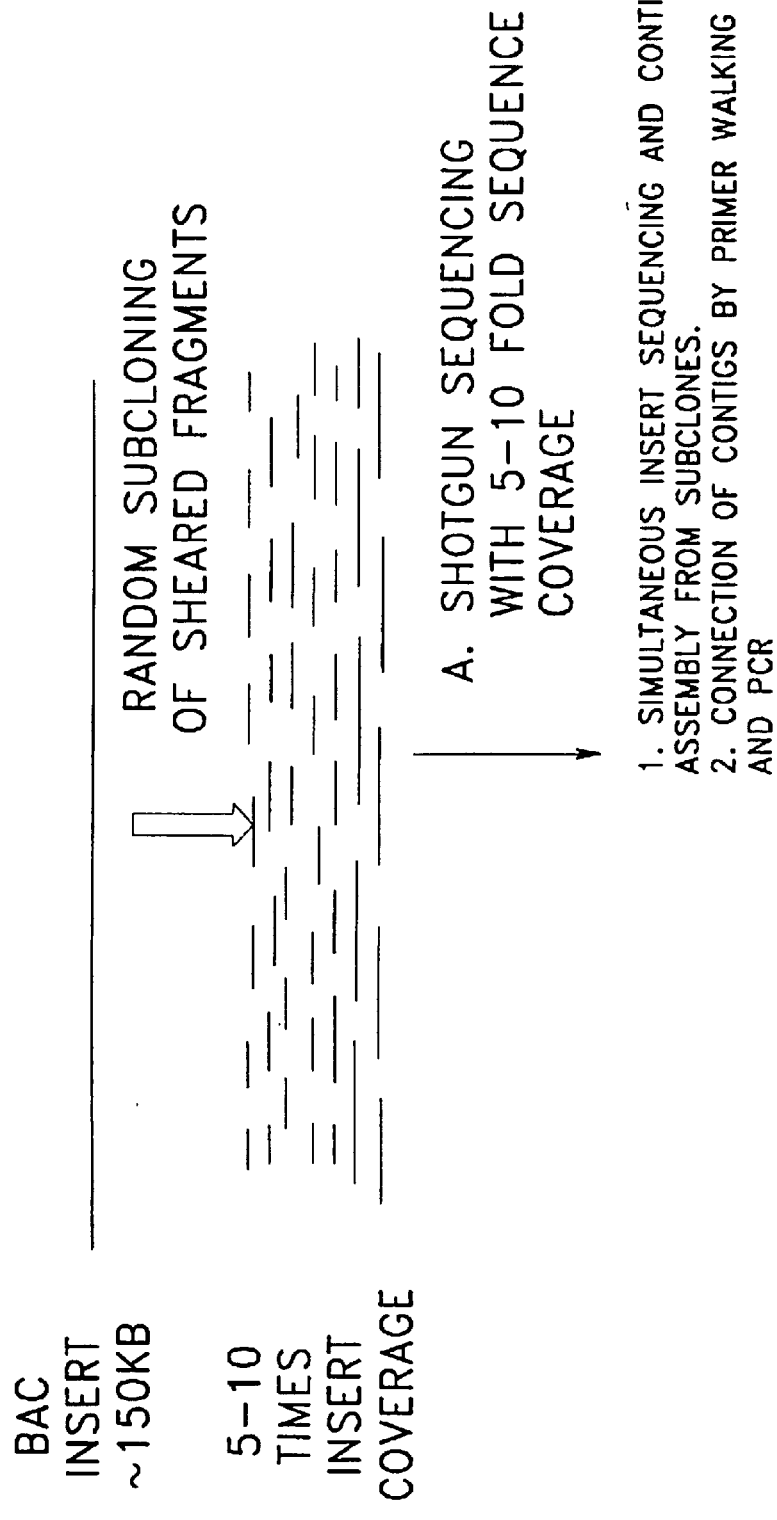
FIG. 9A is a summary of the shotgun sequencing strategy.

Several strategies for obtaining the complete sequence of large inserts are currently practiced. In the shotgun strategy illustrated in FIGS. 6 and 9A, the BAC insert is extracted and broken in a random manner, usually by sonication or enzymatic digestion. The resulting random smaller fragments are cloned into other vectors and the ends of the inserts in these subclones are sequenced. The insert sequences are used to assemble contigs which are connected together by primer walking and PCR. However, the orientation and proximity of each of the inserts relative to the other inserts is not determined. Instead, sequencing of the ends of the random inserts continues until contigs can be assembled. The contigs are then connected together by primer walking.

After all sequences have been determined, they can be assembled into islands and contigs [Staden, R. A new computer method for the storage and manipulation of DNA gel reading data. Nucl. Ac. Res. 8: 3673–3694, 1980, the disclosure of which is incorporated herein by reference]. An island is a set of overlapping sequences. A contig is an island containing at least two sequences. At the early stage (i.e. small number of sequences), there are many islands and holes (unsequenced regions). As the number of sequences increases, the sum of the islands' length increases and the sum of the holes' length decreases. The redundancy, defined as the total length of read sequences divided by the BAC insert length, is also increasing. The redundancy is a parameter which can be used in order to estimate the cost for sequencing a BAC insert.

The sequence of the full BAC insert is achieved when there is one island left which covers the whole BAC insert. For a sequence containing no repeats (the problem of the repeats will be detailed later), the redundancy required for completely sequencing a typical BAC insert using shotgun sequencing techniques is between 5 and 7, according to Poisson's law.

Figure 7:
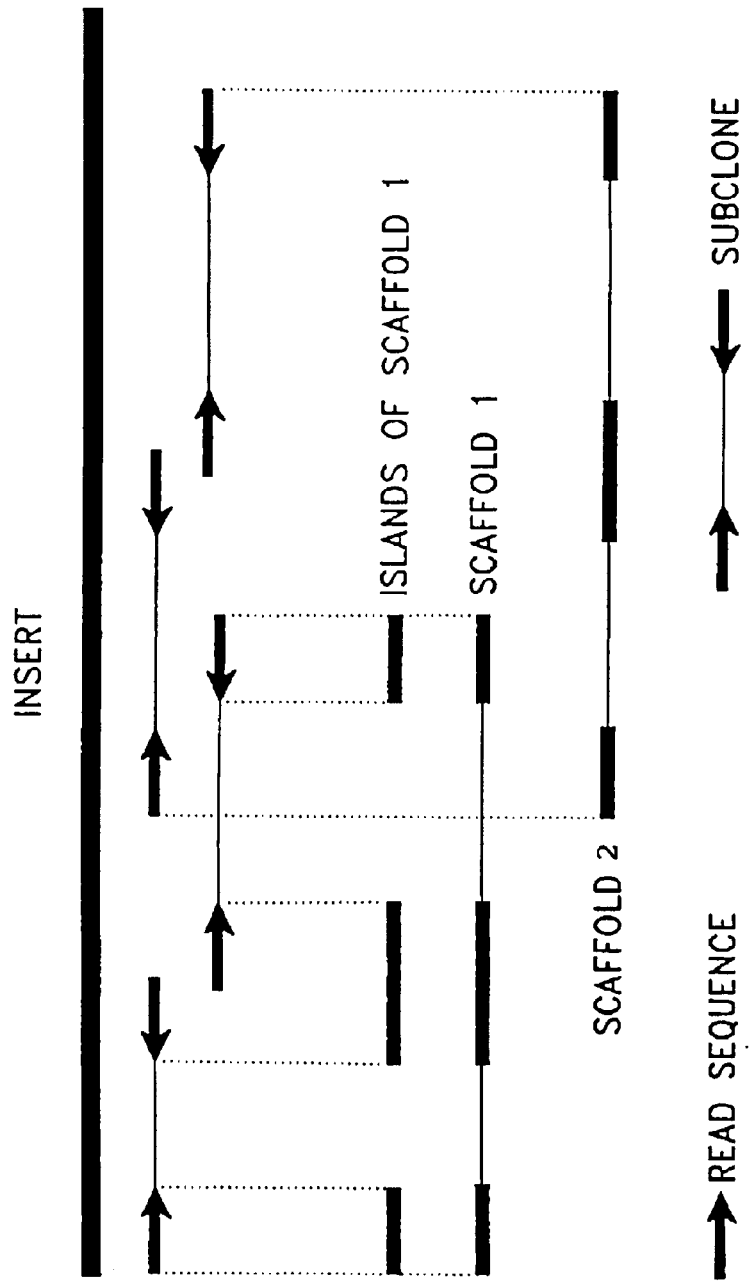
FIG. 7 is a summary of the pairwise sequencing strategy.
Figure 9B:
FIG. 9B is a summary of the OSS method of pairwise sequencing.
Figure 9B:
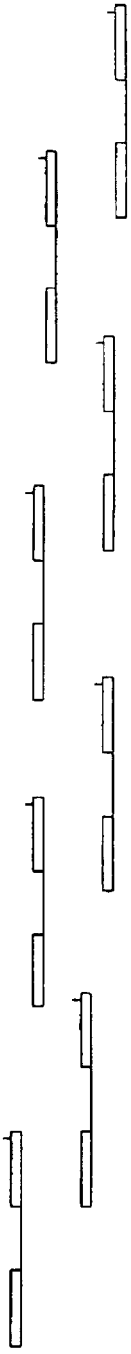
Figure 9C:
FIG. 9C is a summary of the multiple nucleation point sequencing strategy.
Figure 9C:
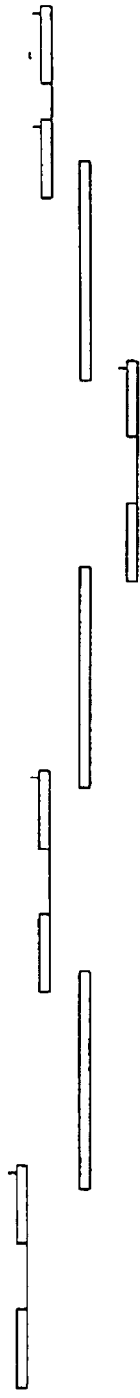

Another method currently in use is the OSS method of pairwise sequencing, which is illustrated in FIG. 9B. The OSS method of pairwise end sequencing [Chen, E., Schlessinger, D., Kere, *J. Genomics,* 17: 651–656 (1993), the disclosure of which is incorporated herein by reference] was proposed to assemble a minimal tiling path by sequencing ends of sub-clones. As depicted in FIGS. 7 and 9B, both ends of a limited number of subclones derived from randomly sheared DNA and having 1.5 to 2 fold sequence coverage are sequenced. A minimal tiling path of subclones is assembled by pairwise sequence overlap. Primer walking is used to sequence the subclones making up the minimal tiling path. In the OSS method, primary sequence information is used both for the determination of the final "finished" structure and for mapping, that is for production of a set of overlapping sub-clones covering the entire length of the initial clone. Each sub-clone of a BAC insert can provide two sequences, if the size of the insert is long enough.

In the shotgun sequencing method described above, the information about the orientation of both sequences and their proximity is not used. As illustrated in FIGS. 7 and 9, in the OSS method the ends of multiple subclones are sequenced and subclones having overlapping sequences are linked to create islands. Sets of islands are ordered and oriented with respect to one another to create scaffolds [Roach, J. C., Boysen, C., Wang, K., & Hood, L. Pairwise end sequencing: a unified approach to genomic mapping and sequencing. Genomics 26: 345–353, 1995, the disclosure of which is incorporated herein by reference]. The scaffolds constitute maps of the BAC with islands as landmarks (FIGS. 7 and 9). A scaffold contains holes, but their length is shorter than the maximum sub-clone size. Thus, a scaffold is a region of the BAC which is ready to be sequenced rapidly. By selecting an appropriate sub-clone size, the size of the holes in the scaffolds can be controlled. If the holes' length is short enough, it can be filled by primer walking. Thus, the OSS method produces an intermediate result, the construction of scaffolds.

The covering rate of the BAC insert by a scaffold is a critical value. As used herein, the covering rate refers to the percentage of bases of the insert which have already been determined. Another key point is the number of scaffolds. Independent scaffolds can be oriented by PCR. In such procedures, the extremities of each scaffold are analyzed in order to define PCR primers, oriented towards the outer ends of the scaffolds. For example, if pa1 and pa2 are a pair of primers defined by scaffold A and pb1, pb2 are a pair of primers for scaffold B the distance between the scaffolds and their orientation can be determined by PCR. Long range PCR is conducted using each possible combination of a primer from scaffold A and a primer from scaffold B (i.e (pa1, pb1), (pa1, pb2), (pa2, pb1) or (pa2, pb2)). If one of the long-range PCR reactions gives an amplified fragment, the relative orientation of the scaffolds and the distance between them can be estimated. This method is practical but the number of primers needed increases as the square of number of scaffolds. The reduction of the number of scaffolds is thus a critical point.

After a sufficient number of sub-clones have been sequenced, the minimal tiling path and a partial sequence can be produced. The resulting selected clones can then be sequenced by primer walking or other methods. When practically applied to human genomic BACs, however, several constraints of the OSS method are limiting. One limitation is the absolute necessity to get sequence information from both ends of the same sub-clone. This can usually be efficiently accomplished when the DNA fragment has no repeats. In the absence of repeats, computer simulations show that almost the whole insert can be covered by a single scaffold with a redundancy of less than 2 (Roach, 1995, supra).

The existence within the human genome of multiple repeats limits the number of clones with unique sequences at both ends and the efficiency of the OSS method. For instance, two distinct sequences can appear to overlap because they contain an ALU repeat. A practical way of avoiding this problem is to compare all primary produced sequences to a database of all known human repeats, and to mask all bases corresponding to the repeats. A masked base is declared to be not useful for the contigation. However, some of the primary sequences may contain a large part of a repeated sequence, preventing them from being contigated to the other sequences. Thus, when the repeat rate is high, a significant portion of the determined sequences can be lost for contigation. In such instances, the information necessary for the OSS method is lost and the gain of efficiency relative to the shotgun strategy is also lost. This phenomenon was observed empirically during practical application of the OSS strategy and in the computer simulation provided below.

The above factors substantially increase the amount of sequencing required to assemble a contig for subsequent final sequencing. In the new multiple nucleation point procedure, summarized in FIGS. 8 and 9C, the sequences of several full subclones derived from randomly sheared DNA are completely determined. The ends of the remaining subclones are sequenced to enable the subclones to be ordered into a contig. The sequence of the contig may then be determined using techniques such as transposon mediated sequencing or other conventional sequencing methods. Thus, using the multiple nucleation point strategy, the walking process is based on the end-sequencing of the totality of the subclones, while the internal sequences of the completely sequenced subclones allow them to be used in constructing the contig even if their ends contain repeat sequences. The problem of contig assembly which arises for a large region will be reduced to the assembly of several smaller contigs, thus reducing the possible branching due to artefacts. At each walking step of the multiple nucleation point strategy, more subclones will be "allocated" to each nucleation point, and many clones with only one informative end will be integrated into the contig. When enough deletion subclones are generated, it becomes possible to sort them by size and to select a set of subclones in which the difference of length between two consecutive clones is less than the number of base pairs that can be read in a sequencing gel. In this case, all sequences overlap with the sequences of the neighbour clones and the contigation will be quite easy. Since the positions of the deletion clones are known, even repeats can be contigated. This increases the number of consecutive bases that can be assembled into a contig for each sequencing reaction performed. Even when the frequency of repeat sequences is high, the multiple nucleation point procedure allows contigs to be efficiently constructed.

The number and length of the subclones which must be fully and partially sequenced in order to obtain the complete sequence of a given large region of DNA using the multiple nucleation point strategy may vary depending on factors such as the individual DNA sequence and the frequency of sub clones having repeat sequences at their ends. Consequently, the descriptions below are intended to illustrate the principles of the multiple nucleation point sequencing strategy and the practice of this method is not limited to the precise protocols set forth below.

The BAC insert or other large piece of chromosomal DNA may be subcloned as fragments comprising about 10 times the insert equivalent (i.e. the number of base pairs in the subcloned fragments is about 10 times the number of base pairs in the original BAC insert). In some embodiments, the large piece of DNA is subcloned as fragments comprising about 4 times the insert equivalent. In further embodiments, the large piece of DNA is subcloned as fragments comprising about 2.5 times the insert equivalent. In still further embodiments, the BAC insert or other large piece of chromosomal DNA is subcloned as fragments comprising less than 2 times the insert equivalent.

In some embodiments, 1–100% of the subclones may be completely sequenced, while only the ends of the remaining subclones are sequenced. In further embodiments about 20% of the subclones are completely sequenced while only the ends of the remaining subclones are sequenced. In still further embodiments, 1–10% of the subclones are completely sequenced, while only the ends of the remaining subclones are sequenced. In other embodiments, 1–5% of the subclones are completely sequenced, while only the ends of the remaining subclones are sequenced.

The fully sequenced subclones and the subclones in which only the ends were sequenced are arranged into one or more scaffolds comprising overlapping subclones which cover the complete sequence of the piece of DNA in the BAC insert. The overlapping subclones which cover the complete sequence of the piece of DNA are then sequenced to determine the full sequence of the piece of DNA. The overlapping subclones may comprise about 1 to about 5 insert equivalents of DNA. Preferably, the overlapping subclones comprise about 2.5 insert equivalents of DNA. The overlapping subclones are completely sequenced to determine the complete sequence of the piece of DNA.

For example, in some embodiments about one insert equivalent of DNA in the subclones may be completely sequenced and about one insert equivalent of DNA in the subclones may be sequenced at the ends to establish an overlapping set of subclones covering the complete sequence of the piece of DNA. An additional 0.5 (or less) insert equivalents of DNA in the overlapping sub clones covering the complete sequence of the piece of DNA may be sequenced to fill in gaps between the fully sequenced subclones and the end sequenced subclones.

Figure 8:
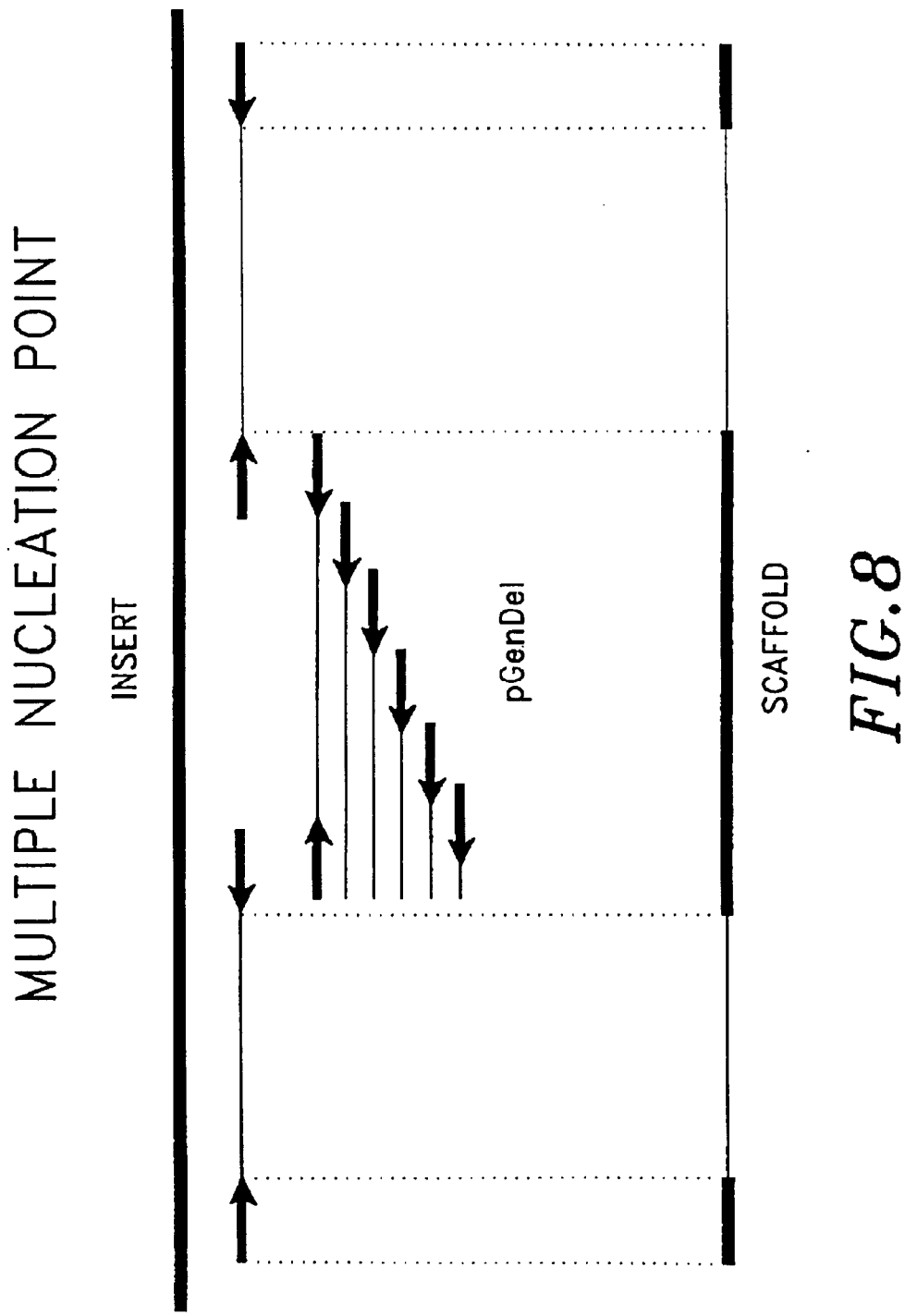
FIG. 8 is a summary of the multiple nucleation point sequencing strategy.

The multiple nucleation point walking strategy is illustrated in FIGS. 8 and 9. Example 5 describes the implementation of the multiple nucleation point strategy.

EXAMPLE 5

A Bacterial Artificial Chromosome with a 100 kb insert is randomly subcloned in pGenDel1, with an average subclone insert size of 10 kb. Ninety six subclones, comprising 10 times the insert equivalent, are picked. One out of five such subclones is entirely sequenced, while for the rest of the subclones, only their end sequences are determined. With this one to five ratio between the numbers of entirely sequenced and end sequenced sub clones, nearly all clones can be attributed to one of the resulting nucleation points, thus giving a high chance of building a minimal tiling path of subclones covering the full length of the insert which can be readily sequenced by nested deletions.

Computer simulations indicate that the multiple nucleation point strategy increases efficiency. These computer simulations allow the optimal number of nucleation points to be defined as a function of the presence of repeats, and of the real efficiency in sequence reading. These parameters can be determined experimentally throughout the end sequencing phase of the project for each individual BAC insert. As a result, optimization of the amount of raw sequencing required through the use of the multiple nucleation point strategy will decrease the amount of sequence information necessary to obtain the complete sequence by several fold. The computer simulation below illustrates the increased efficiency of the multiple nucleation point strategy.

In order to better estimate the advantages of the multiple nucleation point sequencing strategy in different DNA content situations, computer simulations were run comparing the number of sequence scaffolds generated, as well as the maximum length of sequenced scaffolds, using both a classical pure pairwise method and the multiple nucleation point strategy, assuming pairwise sequencing in addition to the prior sequencing of one genome equivalent of the new vector.

The hypotheses used were the following:
OSS method:
  size of the BAC insert: 100 kb
  size of subclones for pairwise sequencing: 10 kb
MNP method:
  size of subclone inserts: 10 kb
problems:
  ALU rate: 40% (compared to a documented 20% average along the whole human genome)
  3 regions of 6.5 kb, not possible to contigate (ALU clusters, long repeat stretches)
technical constraint read presequence run: 400 bp contigation based on 35 bp overlap.

Figure 10:
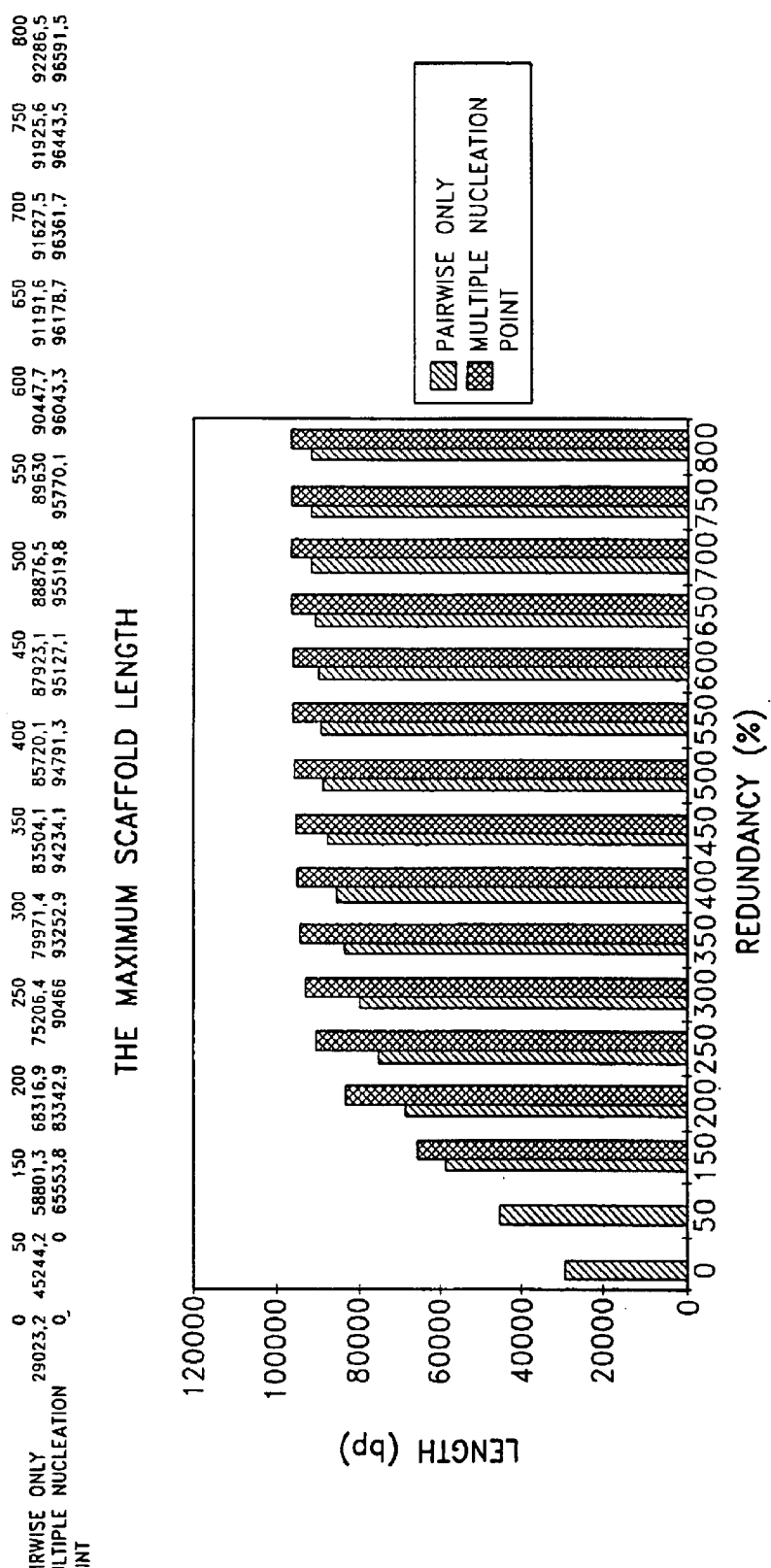
FIG. 10 is a comparison of the maximum scaffold lengths using the OSS method of pairwise sequencing and the multiple nucleation point sequencing strategy.

FIG. 10 shows the maximum scaffold readable using both approaches under the above conditions. The multiple nucleation strategy allows a better final covering rate of the sequence (higher than 95%, as opposed to 90% using the pairwise strategy). In addition, the multiple nucleation point strategy requires the sequencing of fewer genome equivalents to cover the sequence than the pairwise strategy. Using multiple nucleation point sequencing, the covering rate is optimized (95%) when approximately 3 genome equivalents have been sequenced. In contrast, the pairwise method achieves a 90% covering rate when approximately 7 genome equivalents have been sequenced.

Figure 11:
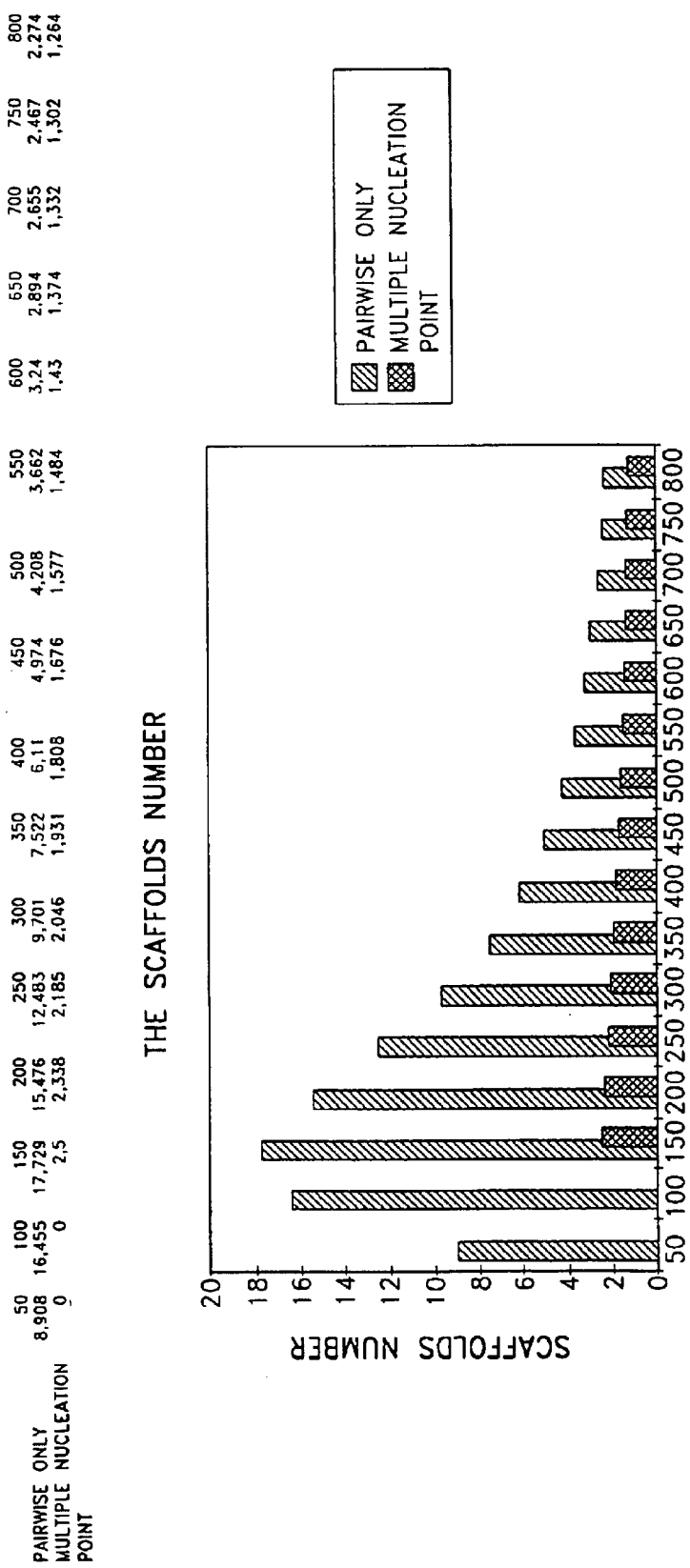
FIG. 11 is a comparison of the number of scaffolds generated using the OSS method of pairwise sequencing and the multiple nucleation point sequencing strategy.

FIG. 11 exemplifies the number of scaffolds generated using both of the above-mentioned approaches, assuming the above conditions. FIG. 10 shows that when 3 genome equivalents have been sequenced, the covering rate is quite satisfactory. Let's consider the case where the redundancy is 3. With the multiple nucleation point strategy, the average scaffold number is 2, as opposed to 10 with the classical pairwise strategy. Converted to the number of long range PCR reactions needed for ordering the scaffolds, the ratio is 4:100. The multiple nucleation point strategy allows the finishing steps (scaffold ordering and gap filling by PCR) to be started with a low redundancy (2.5–3) while the pairwise method does not.

Figure 12:
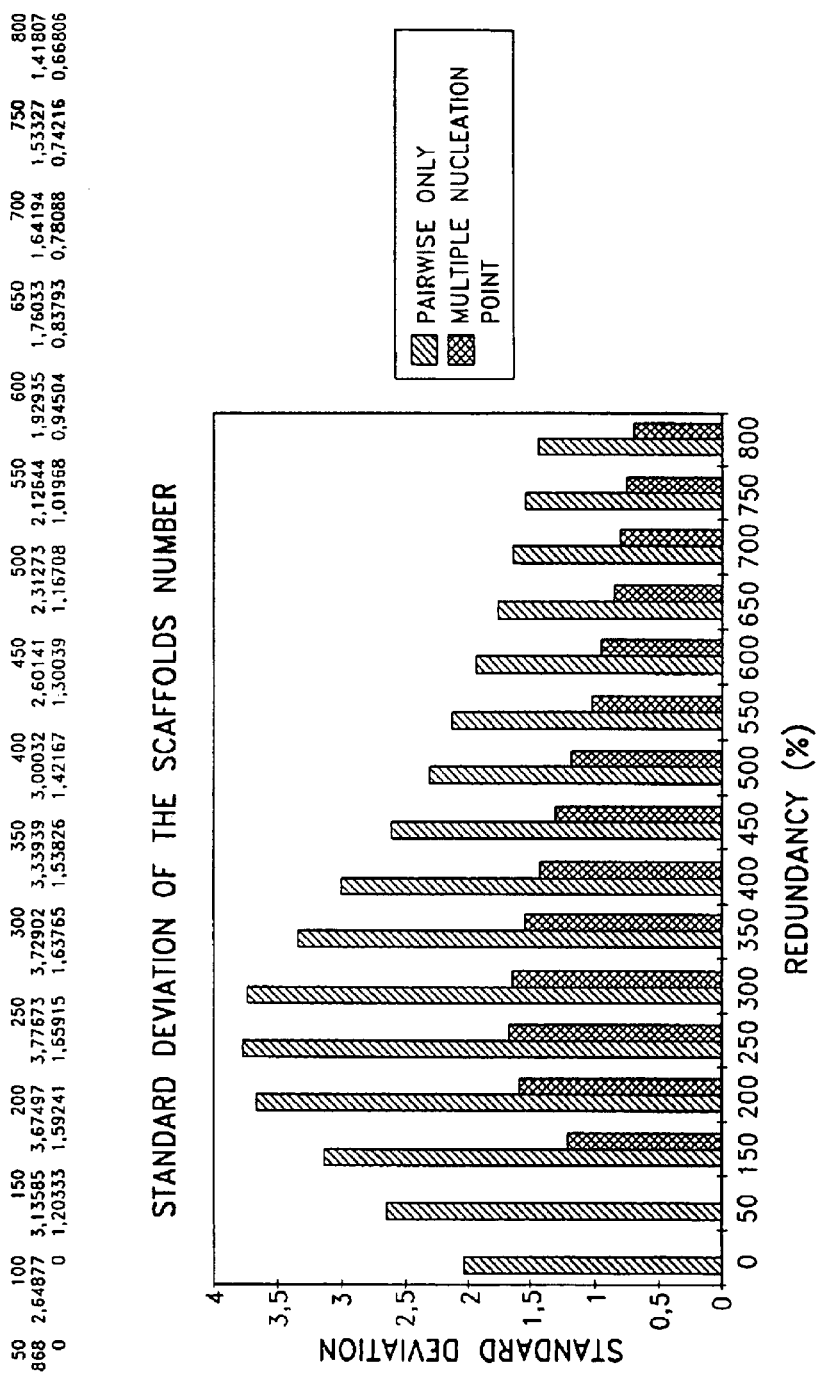
FIG. 12 is a comparison of the standard deviations of the scaffold numbers between the multiple nucleation point and the pairwise strategies.

The reduction of the scaffold number is a main advantage of the multiple nucleation point strategy (FIG. 11). FIG. 11 compares the average values of the scaffold numbers between the multiple nucleation point and the pairwise strategies. FIG. 12 shows the variability of these values, described by the standard deviation. When the redundancy is 2.5–3.0 (which is required for a good coverage rate using the multiple nucleation point strategy), the standard deviation of the scaffold number is only 1.5 with the multiple nucleation point method, as opposed to more than 3.5 with the pairwise method. Statistically, the scaffold number can easily reach values near to: (mean+standard deviation). This value for both methods is:
  Multiple nucleation point: 2+1.5–3.5
  Pairwise: 10+3.5=13.5

The numbers of long range PCR reactions needed are 12 for the multiple nucleation point strategy and 182 for the pairwise strategy.

Thus, the multiple nucleation point strategy allows the finishing steps (scaffold ordering, gap filling) to be started when the redundancy is lower than 3, even if the statistical variation of the scaffold number is taken into account, taking into account the statistical variability.

The results obtained using the new approach are much less variable (see FIG. 12). This is a great advantage if one wishes to develop an industrialized automated large scale sequencing process.

Another aspect of the present invention is a method for mapping the position of a marker along a large region of DNA by determining whether the marker is present in a series of nested deletions made in the large region of DNA.

VIII. Mapping of DNA Features with pGenDel1

The nested deletions generated using pGenDel1 may also be used to map the distribution of markers along the insert cloned therein.

The nested deletions generated with the help of pGenDel1 can be used not only to sequence large inserts, but also to map virtually any DNA pattern alongside large ranges of inserts. As previously mentioned, the single copy, stable nature of pGenDel1-based recombinants allows the efficient cloning of fragments from several bases to several hundreds of kilobases long. After any of the above described deletion methods is applied, a minimal tiling path of the resulting subclones can be generated by sizing the inserts using PCR or restriction analysis.

The presence of a particular sequence within the deleted inserts can be evaluated using PCR or by hybridizing a detectable probe to the deleted plasmids. When tested by PCR or with a hybridization probe, this minimal tiling path will show a positive signal up to the point of localization of the studied marker. Measuring the size of the last positive insert will correspond to mapping the position of the marker being evaluated. Therefore, pGenDel1 can be used for mapping a wide range of markers, including bi-allelic marker, STS (sequence tagged site), or mutation mapping, as well as the localization of genes, simple and other repeats, promoters, enhancers, terminators of RNA synthesis and other markers. Example 6 below illustrates a mapping procedure using nested deletions in pGenDel1 inserts.

EXAMPLE 6

Three sequence tagged sites (STS) were mapped using deletions generated in pGenDel1 inserts using transposon based procedures. The deletions were generated in a subclone containing an insert (B0180G09.H05) derived from the chromosome 21 specific BAC vector designated BAC B0180G09. Transposon based deletions were generated as described above. The transposon based deletions in the insert were characterized by PCR analysis as described above and a minimal tiling path of 18 deletions was picked. The insert sizes in the various deletions were as follows:

E11: 5000 bp
B02: 4900 bp
B06: 4800 bp
C04: 4500 bp
G01: 4300 bp
D08: 4100 bp
G11: 3900 bp
C06: 3800 bp
B11: 3300 bp
B07: 3000 bp
C05: 2600 bp
A12: 2200 bp
A03: 1900 bp
G10: 1700 bp
H04: 1250 bp
D07: 1100 bp
E03: 700 bp
F08: 300 bp.

To evaluate whether each of the above inserts contain STSg621, a PCR reaction was performed using the primers g621d: GCAGAGAAGTAAGCCTTCAA and (SEQ ID NO: 21) and g621r: AGAGGTCTCAGTAACCAGACC (SEQ ID NO: 22).

The PCR was performed on 2 $\mu$l of an overnight culture of cells harboring the above subclones, with 3.2 pM of each primer and 1 unit of Taq DNA polymerase (Perkin Elmer), in a 15 $\mu$l final reaction volume. 30 cycles were performed each consisting of 30 seconds at 94° C., 30 seconds at 55° C., and 30 seconds at 72° C. The PCR reaction would produce a 213 bp amplicon if STSg621 is present in the insert. The resulting reaction products were analyzed on a 2% agarose gel for the presence of the 213 bp amplicon. The 213 bp amplicon was observed in all clones having inserts of 1.9 kb or longer. In contrast, the clones having inserts primers of 1.7 kb or shorter did not produce the 213 bp amplicon, thus positioning g621 in the interval 1.7–1.9 kb from the oriLRr primer. This location was confirmed by sequence analysis.

The above mapping procedures were also used to map the positions of STS g620 and STS g622 using two other subclones derived from BAC B0180G09. STS g620 was mapped to a position around 1.8 kb of sub-clone 01H08, and STS g622 was mapped to a position at 3 kb in the insert of subclone 01G10. The positions of each of these STS were also confirmed by sequence analysis.

Those skilled in the art will appreciate that other non-PCR based methods can be used to determine whether a given marker is present in a series of nested deletions. For example, standard hybridization based detection analyses may be used to determine whether the marker is present. In one version of such hybridization based analyses, traditional Southern blots may be performed. In such Southern blotting analyses, vector DNA may be isolated from transformed cells, digested with enzymes which cut out the insert, run on agarose gels and transferred to a nitrocellulose or nylon filter. The filter is then probed with a detectable primer having a sequence contained within the marker of interest. The presence of a detectable signal on the filter indicates that the marker is present in the insert while the absence of a detectable insert indicates that the deletion has removed the marker. Southern blotting techniques are well known to those with skill in the art. For a review of Southern blotting see Davis et al. (*Basic Methods in Molecular Biology*, 1986, Elsevier Press. pp 62–65) or Sambrook et al., Molecular Cloning: A Laboratory Manual 2nd Ed., Cold Spring Harbor Laboratory Press, 1989, the disclosures of which are incorporated herein by reference.

An alternative hybridization based detection procedure is the dot blot. Dot Blots are created by spotting the vector DNA onto nitrocellulose or the like using a vacuum dot blot manifold (BioRad, Richmond Calif.). The nitrocellulose filter containing the genomic sequences is baked or UV linked to the filter, prehybridized and hybridized with a detectable probe having a sequence contained within the marker being evaluated using techniques known in the art (Davis et al. or Sambrook et al., supra). The presence of a detectable signal indicates that the insert contains the marker, while the absence of a detectable signal indicates that the deletion has removed the marker.

Another hybridization based technique is colony hybridization. In such procedures, bacterial colonies containing vectors having nested deletions are grown on nitrocellulose or nylon filters. The colonies are lysed, and the vector DNA is fixed to the filter. The filter is then probed with a detectable probe contained within the sequence of the marker being mapped. The presence of a detectable signal indicates that the insert contains the marker, while the absence of a detectable signal indicates that the deletion has removed the marker. Colony hybridization techniques are disclosed in Sambrook et al., supra.

Alternatively, the presence of a given marker in a series of nested deletions can be evaluated using microarrays. In such procedures, the marker DNAs to be evaluated or portions thereof are affixed to a microarray chip. Techniques for preparing microarray chips are described in Schena et al. (Science 270:467–470, 1995; Proc. Natl. Acad. Sci. U.S.A. 93:10614–10619, 1996), Pietu et al. (Genome Research 6:492–503, 1996), Lockhart et al. (Nature Biotechnology 14: 1675–1680, 1996) and Sosnowsky et al. (Proc. Natl. Acad. Sci. 94:1119–1123, 1997), the disclosures of which are incorporated by reference. Probes are generated by performing PCR reactions on each member of the series of nested deletions using primers which would amplify the marker if it is present. The PCR products are hybridized to the marker DNA on the chips. Detection of a signal on the microarray indicates that the marker is present in the corresponding deletion construct.

IX. BAC Vectors

As described above, the present invention includes vectors for maintaining inserts at low copy number. Maintenance of the insert at low copy number reduces the likelihood that the insert-containing vectors used in manipulations following the cloning of the insert into the vector will contain mutations within the insert. In addition, maintenance of the insert at low copy number increases its stability and allows the recovery of insert sequences which may be toxic if present at a high copy number. These features may be particularly advantageous when constructing genomic DNA libraries such as BAC libraries.

Vectors useful in such applications comprise a high copy number origin of replication having at least one cloning site therein which is positioned such that the ability of the high copy number origin of replication to direct replication is lost when an insert is cloned into the cloning site. In addition, the vectors comprise a low copy number origin of replication and any genes necessary for the activity of the low copy number origin of replication, at least one copy number indicator for indicating the copy number of the vector in the host cells, and a vector maintenance marker for selecting cells containing the vector. If desired, the vectors may also include hybridization sites for primers for amplifying the insert and hybridization sites for primers for sequencing the amplified insert.

Figure 13:
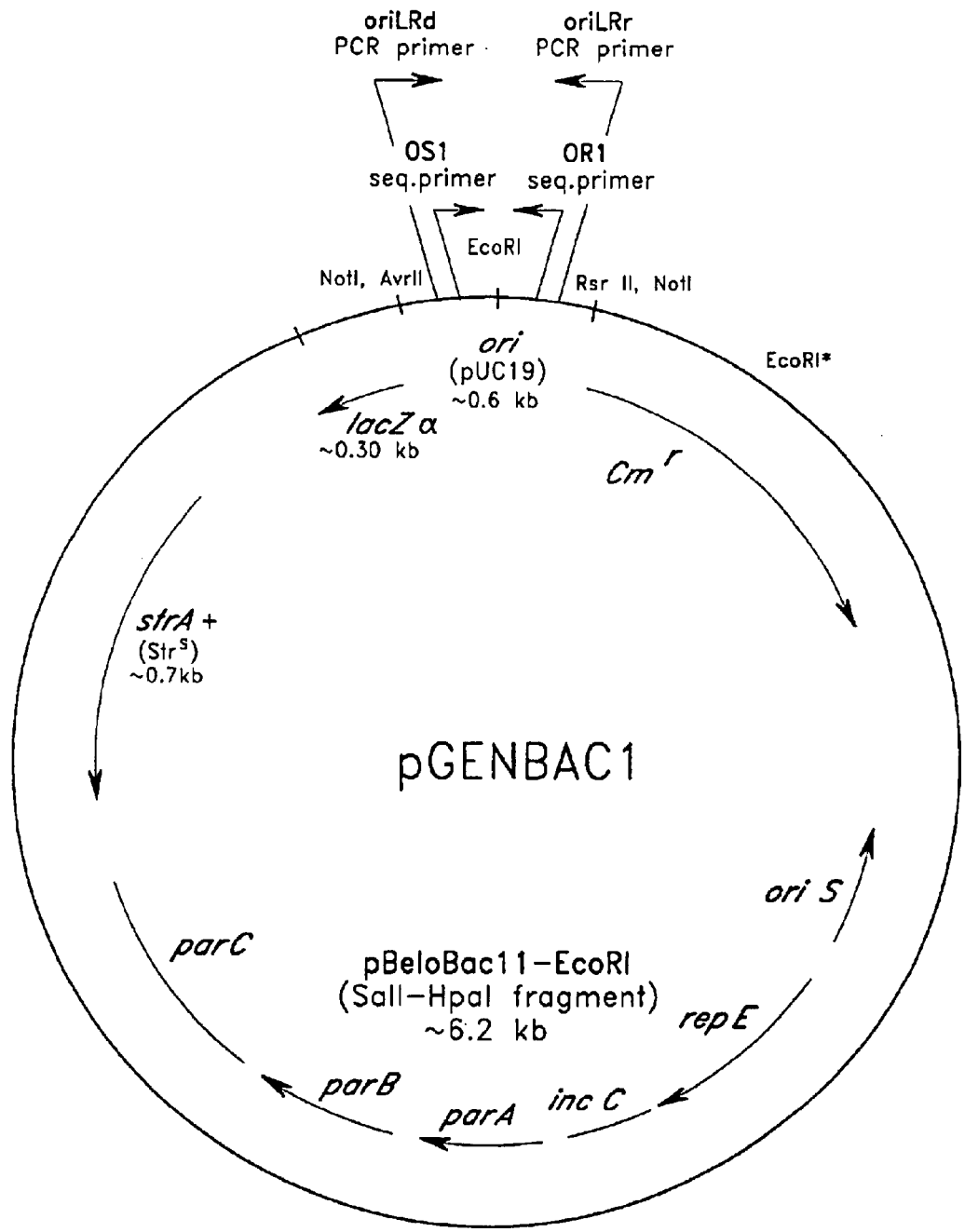
FIG. 13 is a map of pGenBac1.
Figure 14:
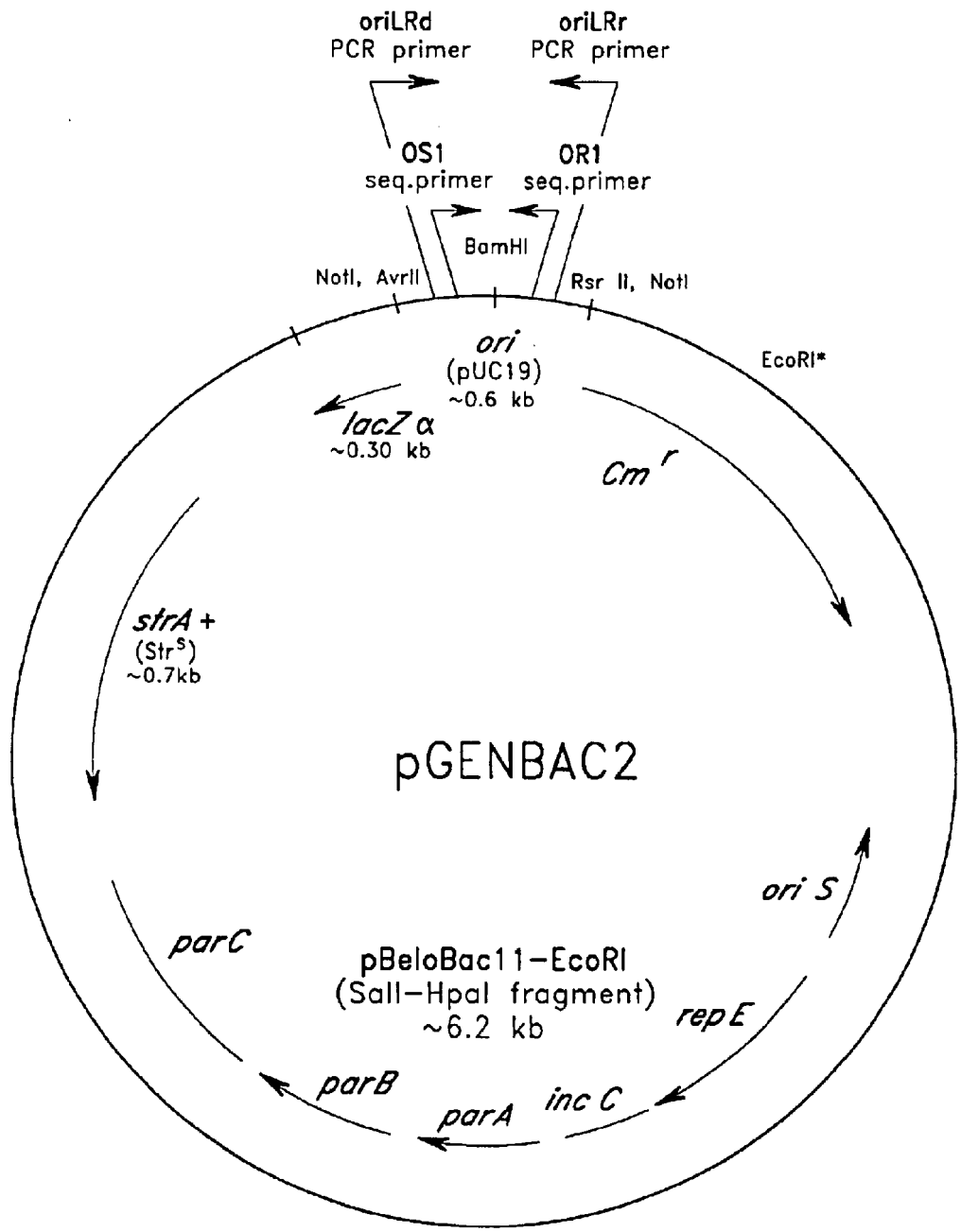
FIG. 14 is a map of pGenBac2.

Exemplary vectors for maintaining inserts at low copy number (designated pGenBac1 and pGenBac2) are shown in FIGS. 13 and 14. Each of these vectors contain the high copy number origin of replication from pUC19 with a unique cloning site therein. In pGenBac1 the unique cloning site in the high copy number origin of replication is an EcoRI site, while in pGenBac2 the unique cloning site in the high copy number origin of replication is a BamHI site. When an insert is cloned into the EcoRi site of pGenBac1 or the BamHI site of pGenBac2, the activity of the high copy number origin of replication is disrupted. However, as described above, vectors having inserts therein are capable of replicating at low copy number under the control of oriS and its associated regulatory genes.

pGenBac1 and pGenBac2 also contain the strA gene which permits the selection of streptomycin resistant host cells carrying vectors having inserts therein as described above. In addition, pGenBac1 and pGenBac2 contain the truncated lacZ gene described above as a copy number indicator.

A gene conferring resistance to chloramphenicol is used as a vector maintenance marker. In addition, pGenBac1 and pGenBac2 also contain hybridization sites for the oriLRd and oriLRr PCR primers described above to permit amplification of the insert DNA. Hybridization sites for the OS1 and OR1 sequencing primers are also included to allow the amplified insert to be sequenced.

Example 7 describes the construction of pGenBac1 and pGenBac2.

EXAMPLE 7

The HpaI-SalI fragment extending from nucleotide 646 to nucleotide 6995 of pBeloBac11 (GenBank accession number U51113, the disclosure of which is incorporated herein by reference) was modified by site directed mutagenesis at positions 1207–1213 of pBeloBac11 to remove the EcoRI site. This modification changed the sequence GAATTCC between bases 1207 and 1213 of pBeloBac to the sequence TAATC. The modified HpaI-SalI fragment was then joined to the strA gene to generate an intermediate construct. Thereafter the truncated lacZ gene and a NotI AvrII RsrI NotI polylinker were inserted into the intermediate construct adjacent to the strA gene.

The pUC19 origin of replication was modified by site directed mutagenesis to create origins having an EcoRI site (pGenBac1 ) or a BamHI site (pGenBac2) therein. The sequences of these modified origins are provided in the accompanying Sequence Listing and are identified as SEQ ID NO: 18 and SEQ ID NO: 19. These modified origins of replication replicate at approximately the same copy number as the unmodified origin.

The modified origins were amplified and inserted between the AvrII and RsrI sites of the polylinker. The resulting constructs are shown in FIGS. 13 and 14.

Cloning of an insert into the EcoRI site of pGenBac1 or the BamHI site of pGenBac2 inactivates the high copy number pUC19 origin of replication. However, plasmids carrying inserts are maintained at low copy number through the activity of oriS and its associated regulatory genes. Vectors carrying inserts therein are chloramphenicol resitant, streptomycin resistant, and light blue on IPTG/Xgal.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents and GenBank accession numbers cited herein are incorporated herein by reference in their entirety.

What is claimed is:

1. A method for identifying vectors containing a DNA insert, comprising the steps of:
    subjecting a plurality of vectors to insertion conditions under which an insert is placed in at least some of said vectors, wherein said vectors have a first copy number if no insert occurs and a second copy number if an insert occurs; and
    identifying at least some vectors containing an insert by screening said vectors for said second copy number.

2. The method of claim 1, wherein said vectors comprise hybridization sites for insert sequencing primers, said hybridization sites for insert sequencing primers being positioned so as to allow the sequencing of said DNA insert.

3. The method of claim 1, wherein said vectors comprise hybridization sites for insert amplifying primers, said hybridization sites for insert amplifying primers being positioned so as to allow the amplification of said DNA insert.

4. The method of claim 1, wherein said vectors comprise a single stranded origin of replication, said single stranded origin of replication permitting the isolation of said vector in a single stranded form.

5. The method of claim 1, wherein said vectors containing a DNA insert are present at a low copy number.

6. The method of claim 1, wherein said first copy number is a high copy number and said second copy number is a low copy number.

7. The method of claim 1, wherein said vectors comprise at least one copy number indicator for indicating the copy number of said vectors in cells.

8. The method of claim 7, wherein said copy number indicator comprises a selectable marker.

9. The method of claim 1, wherein said screening step comprises determining the copy number of a vector.

10. A method to determine the copy number of a vector comprising a truncated lacZ gene, said method comprising the steps of:
    introducing said vector into a host cell, wherein said truncated lacZ gene, when present at a high copy number in said host cells, confers dark blue coloration to said host cells grown on a medium containing Xgal and IPTG, and wherein said truncated lacZ gene, when present at a low copy number in said host cells, confers light blue coloration to said host cells grown on said medium; and
    determining the color of the host cells when the host cells are grown on said medium.

11. A method to determine the copy number of a vector comprising the strA+ gene, said method comprising the steps of:
    introducing said vector into a streptomycin resistant host cell, wherein said host cells are unable to grow in the presence of streptomycin when the strA gene is present at a high copy number and wherein said host cells are able to grow in the presence of streptomycin when the strA gene is present at a low copy number; and
    determining the ability of said host cells to grow on a medium containing streptomycin.

12. The method according to claim 11, wherein said vector further comprises a high copy number origin of replication and a low copy number origin of replication.

13. The method according to claim 12, wherein said high copy number origin of replication contains one or more cloning sites.

14. The method according to claim 11, wherein said vector comprises additional selectable markers.

15. The method according to claim 10, wherein said truncated LacZ gene comprises SEQ ID NO: 7.

16. The method according to claim 15, wherein said truncated LacZ gene comprises nucleotides 1–292 of SEQ ID NO: 7.

17. The method according to claim 10, wherein said truncated LacZ gene comprises nucleotides 1–392 of the LacZ gene sequence.

* * * * *